US010653698B2

(12) United States Patent
Yeager et al.

(10) Patent No.: US 10,653,698 B2
(45) Date of Patent: *May 19, 2020

(54) METHODS OF IMPROVING MYOCARDIAL PERFORMANCE IN FONTAN PATIENTS USING UDENAFIL COMPOSITIONS

(71) Applicants: Mezzion Pharma Co., Ltd., Seoul (KR); Children's Hospital of Philadelphia, Philadelphia, PA (US)

(72) Inventors: James L. Yeager, Lake Forest, IL (US); David J. Goldberg, Philadelphia, PA (US); Stephen M. Paridon, Strafford, PA (US)

(73) Assignees: Mezzion Pharma Co., Ltd., Seoul (KR); The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,523

(22) Filed: Feb. 2, 2018

(65) Prior Publication Data

US 2018/0169103 A1 Jun. 21, 2018

Related U.S. Application Data

(63) Continuation of application No. 14/788,211, filed on Jun. 30, 2015, now Pat. No. 10,137,128.

(60) Provisional application No. 62/186,132, filed on Jun. 29, 2015, provisional application No. 62/036,506, filed on Aug. 12, 2014.

(51) Int. Cl.
*A61P 9/00* (2006.01)
*A61K 31/522* (2006.01)
*A61K 31/519* (2006.01)
*C07D 487/04* (2006.01)
*A61K 31/00* (2006.01)

(52) U.S. Cl.
CPC ............ *A61K 31/522* (2013.01); *A61K 31/00* (2013.01); *A61K 31/519* (2013.01); *A61P 9/00* (2018.01); *C07D 487/04* (2013.01)

(58) Field of Classification Search
None
See application file for complete search history.

(56) References Cited

U.S. PATENT DOCUMENTS

| 10,137,128 | B2 | 11/2018 | Yeager et al. |
| 2005/0272741 | A1 | 12/2005 | Rychik et al. |
| 2011/0250279 | A1 | 10/2011 | Yoo et al. |
| 2019/0030037 | A1 | 1/2019 | Yeager et al. |
| 2019/0030038 | A1 | 1/2019 | Yeager et al. |

FOREIGN PATENT DOCUMENTS

| AU | 2015302271 B2 | 6/2019 |
| EC | SP088311 A | 6/2008 |
| EC | SP088441 A | 6/2008 |
| JP | 2010-532319 A | 10/2010 |
| JP | 2012-197274 A | 10/2012 |
| JP | 2013-514995 A | 5/2013 |
| JP | 2013-523809 A | 6/2013 |
| KR | 20070099363 A | 10/2007 |
| KR | 100792126 B1 | 1/2008 |
| KR | 20130086771 A | 8/2013 |
| KR | 101383430 B1 | 4/2014 |
| RU | 2420289 C1 | 6/2011 |
| WO | 00/27848 A1 | 5/2000 |
| WO | WO 2014078459 A1 | 5/2014 |

OTHER PUBLICATIONS

Further Examination Report for New Zealand Patent Application No. 727653, dated Aug. 10, 2018 (3 pages).
ClinicalTrials.gov—Effect of Tadalafil on Exercise Capacity in Pediatric Fontan Patients, NCT01291069. Feb. 4, 2011. <https://clinicaltrials.gov/ct2/show/NCT01291069>.
ClinicalTrials.gov—Pharmacokinetic/Pharmacodynamic Study of Udenafil in Adolescents, NCT02201342. Jul. 24, 2014. <https://clinicaltrials.gov/ct2/show/NCT02201342?term=udenafil+and+fontan&rank=2>.
Ellis, S. Mezzion's PDE5 inhibitor enters U.S. trials for Fontan patients. BioWorld. Jan. 22, 2014. <http://www.bioworld.com/content/mezzion%E2%80%99s-pde5-inhibitor-enters-us-trials-fontan-patients>.
Fontan circulation: success or failure? Congenital Heart Defect Research Blog. Mar. 13, 2013. <http://bendantzer.wordpress.com/2013/03/13/fontan-circulation-success-or-failure/>.
Mezzion Pharma Announces Collaboration With New England Research Institutes to Evaluate Udenafil in Adolescents With Single Ventricle Heart Defects. PR Newswire. Jan. 10, 2014. <http://www.prnewswire.com/news-releases/mezzion-pharma-announces-collaboration-with-new-england-research-institutes-to-evaluate-udenafil-in-adolescents-with-single-ventricle-heart-defects-239603121.html>.
Mezzion Pharma Initiates Clinical Development Program to Evaluate Udenafil in Adolescents With Single Ventricle Heart Defects. MedIndia. Jul. 23, 2014. <http://www.medindia.net/health-press-release/Mezzion-Pharma-Initiates-Clinical-Development-Program-To-Evaluate-Udenafil-In-Adolescents-With-Single-Ventricle-Heart-Defects-216437-1.htm>.
Mezzion Pharma Initiates Clinical Development Program to Evaluate Udenafil in Adolescents With Single Ventricle Heart Defects. PR Newswire. Jul. 23, 2014. <http://www.prnewswire.com/news-releases/mezzion-pharma-initiates-clinical-development-program-to-evaluate-udenafil-in-adolescents-with-single-ventricle-heart-defects-268268072.html>.
Mezzion. Global C&D business to post tanglible results. 2013.

(Continued)

*Primary Examiner* — H. Sarah Park
(74) *Attorney, Agent, or Firm* — Peter J. Manso; David G. Conlin; Joohee Lee

(57) ABSTRACT

The present invention relates generally to the field of using udenafil or a pharmaceutically acceptable salt thereof in patients who have undergone the Fontan operation.

22 Claims, 34 Drawing Sheets

(56) References Cited

OTHER PUBLICATIONS

Rychik, J. Forty years of the Fontan operation: a failed strategy. Semin Thorac Cardiovasc Surg Pediatr Card Surg Annu. 2010;13(1):96-100.
Trials will evaluate udenafil for heart defects in adolescents. Healio Cardiology Today. Feb. 1, 2014. <http://www.healio.com/cardiology/pediatric-cardiology/news/online/%7Bda00eddc-5a3e-4a27-80d6-05b12bb3acc4%7D/trials-will-evaluate-udenafil-for-heart-defects-in-adolescents>.
Wasserman, E. Mezzion Pharma Appoints Jefferson Gregory to Board of Directors. Fierce Biotech. Oct. 9, 2014. <http://www.fiercebiotech.com/biotech/mezzion-pharma-appoints-jefferson-gregory-to-board-of-directors>.
Bialkowski et al., [Successful chronic treatment with sildenafil in a patient with end-stage heart failure following Fontan procedure]. Kardiol Pol. 2011;69(3):302-4. Polish. [English Abstract].
Ciliberti et al., Impact of oral chronic administration of sildenafil in children and young adults after the Fontan operation. Future Cardiol. Sep. 2011;7(5):609-12.
Giardini et al., Effect of sildenafil on haemodynamic response to exercise and exercise capacity in Fontan patients. Eur Heart J. Jul. 2008;29(13):1681-7.
Giordano et al., First experience with sildenafil after Fontan operation: short-term outcomes. J Cardiovasc Med (Hagerstown). Aug. 2015;16(8):552-5.
Goldberg et al., Impact of sildenafil on echocardiographic indices of myocardial performance after the Fontan operation. Pediatr Cardiol. Jun. 2012;33(5):689-96.
Reinhardt et al., Sildenafil in the management of the failing Fontan circulation. Cardiol Young. Oct. 2010;20(5):522-5.
Colombian Office Action for Application No. NC2017/0000271.
Exhibit a-1: Email from ClinicalTrials.gov to James L. Yeager confirming receipt of Mezzion's Protocol Record PHN-Udenafil-01, Pharmacokinetic/Pharmacodynamic Study of Udenafil in Adolescents submitted by James L. Yeager on behalf of Mezzion. (Jul. 25, 2014).
Exhibit b-1: Press release entitled "Mezzion Pharma Announces Collaboration with New England Research Institutes to Evaluate Udenafil in Adolescents with Single Ventricle Heart Defects" (Jan. 10, 2014).
Exhibit b-2: Email from PR Newswire to James L. Yeager, dated Jan. 9, 2014.
Exhibit b-3: Email from PR Newswire to James L. Yeager, dated Jan. 10, 2014.
Exhibit c-1: Email from Youn-Taek Song (IR Team / Manager for Mezzion Pharma) to Minha Choi of Korean Investment regarding Exhibit c-2, the "Company Report, Mezzion (140410)" (Aug. 13, 2013).
Exhibit c-2: Mezzion report entitled "Company Report, Mezzion (140410)" (Aug. 13, 2013. ).
Exhibit c-3: Mezzion report entitled "Mezzion Investor Relations" (Jul. 2013).
Exhibit c-4: Mezzion report entitled "Mezzion Investor Relations" (Jun. 2014), [English translation of Exhibit c-3].
Exhibit h-1: Email from PR Newswire confirming receipt of the content of Exhibit h-2 submitted by James L Yeager, on behalf of Mezzion. (Oct. 9, 2014).
Exhibit i-1: Email from Youn-Taek Song (IR Team / Manager for Mezzion Pharma) to Sae-Bom Lee of Maeil Business Newspaper. Exhibit i-1 was submitted with four attachments, i.e., (1) Exhibit i-2, Jan. 9, 2014, (2) Exhibit i-3, Jan. 2012, (3) Exhibit i-4, Jul. 23, 2012, and (4) Exhibit i-5, May 16, 2012, attached thereto. Exhibit i-1 is provided in Korean with English translation. (Jan. 10, 2014).
Exhibit i-2: Press release entitled "Zydena in the United States acquired the patent applications for the enlarged Benign prostatic hyperplasia treatment effect" (Jan. 9, 2014).
Exhibit i-3: Mezzion report entitled "Dong-A Pharmtech IR report" (Jan. 2012).

Exhibit i-4: Press release entitled "Zydena, Approved by the Ethics Committee in Mexico" (Jul. 23, 2012).
Exhibit i-5: Press release entitled "Dong-A Pharmtech, Russia Market Second development export after 2007" (May 16, 2012).
Exhibit j-1: Email from Youn-Taek Song (IR Team / Manager for Mezzion Pharma) to reporter Dong In Lee of Maeil Business Newspaper. Attached to Exhibit j-1 is Exhibit j-2, a press release. (Mar. 31, 2015).
Exhibit j-2: Press release entitled "Mezzion, return exclusive rights (develop and marketing) to erectile dysfunction and Benign prostatic hyperplasia in the Americas", Mar. 31, 2015.
Exhibit k-1: Email from Youn-Taek Song (IR Team / Manager for Mezzion Pharma) to reporter YooJin Jo of Asia Business Daily. Attached to Exhibit k-1 are Exhibits k-2, K-3 and K-4. (Jun. 30, 2015).
Exhibit k-2: Press release entitled Mezzion completes to ½ Clinical Trials of Udenafil in Fontan patients. (Mar. 16, 2015).
Exhibit k-3: Press release entitled "Mezzion Pharma Announces Collaboration with New England Research Institutes to Evaluate Udenafil in Adolescents with Fontan Surgery" (Jan. 10, 2014).
Exhibit k-4: Press release entitled "Mezzion, submit uses patent application for Fontan Operation" (Jun. 29, 2015).
Exhibit I: Email from Youn-Taek Song (IR Team / Manager for Mezzion Pharma) to reporter Hyoung-Su Park of Edaily. (Mar. 26, 2014).
Exhibit m: Email from Youn-Taek Song (IR Team / Manager for Mezzion Pharma) to Tai-gi Ha of SK Securities, Chi-hyun Kim of Kiwoom Securities, Mi-hyun Kim of Yuanta Securities Korea, Al-eum Lee of Hana Financial Investment, Bora Chung of Dongbu Securities, and Seun-min Kim of Mirae Asset Daewoo. (Jun. 6, 2014).
Goldberg et al., Results of a phase I/II multi-center investigation of udenafil in adolescents after fontan; palliation. Am Heart J. Jun. 2017;188:42-52.
New Zealand Office Action for Application No. 727653 dated Aug. 24, 2017.
Tunks et al., Sildenafil exposure and hemodynamic effect after Fontan surgery. ; Pediatr Crit Care Med. Jan. 2014;15(1):28-34.
Van De Bruaene et al., Sildenafil improves exercise hemodynamics in Fontan patients. Circ Cardiovasc Imaging. Mar. 2014;7(2):265-73.
S.C. Menon et al., "Effect of Tadalafil on Exercise Parameters in Young Fontan Patients", Circulation, 128:A16024 (2013)—Abstract.
Mession Company Report (140410) dated Apr. 23, 2013, available at http://cfile30:uf.tistory.com/attach/273A264E517619D80E3D0D, accessed on May 27, 2016.
Machine translation of "Mezzion Company Report (140410)", dated Apr. 23, 2013, available at http://cfile30.uf.tistory.com/attach/273A264E517619D80E3D0D, accessed on May 27, 2016.
J. Rychik, "Relentless Effects of the Fontan Paradox", Seminars in Thoracic and Cardiovascular Surgery, 19(1), pp. 37-43 (2016).
D. Goldberg et al., "Fontan Circulation, The Search for Targeted Therapy", Circulation, 130:1999-2001 (2014).
ClinicalTrials.gov—A Service of the U.S. National INstitutes of Health, Pharmacokinetic/Pharmacodynamic Study of Udenafil in Adolescents, Jul. 21, 2016, 4 pages.
Colombian Office Action dated Mar. 5, 2018, for Colombian Patent Application No. NC2017/0000271, 4 pages.
English Translation of Colombian Office Action dated Mar. 5, 2018, for Colombian Patent Application No. NC2017/0000271, 4 pages.
Japanese Notification of Reasons for Refusal dated Mar. 6, 2018, for Japanese Patent Application No. 2017-504434, 4 pages.
English Translation of Japanese Notification of Reasons for Refusal dated Mar. 6, 2018, for Japanese Patent Application No. 2017-504434, 4 pages.
Mori, H. et al. (Nov. 26, 2013). Abstract 16117 "Sildenafil Reduces Pulmonary Vascular Resistance in Patients with Single Ventricular Physiology," *Circulation* 128(Suppl 22):A16117.
Canadian Office Action for Application No. 2,954,183 dated Apr. 27, 2018 (Apr. 27, 2018). 4 pages.
Chilean Office Action for Application No. 201700329 dated May 17, 2018. 8 pages. [Original].

(56) References Cited

OTHER PUBLICATIONS

Chilean Office Action for Application No. 201700329 dated May 17, 2018. 8 pages. [English Translation].
Eurasian Office Action for Application No. 201692518/28 dated May 4, 2018. 2 pages. [English Translation].
Eurasian Office Action for Application No. 201692518/28 dated May 4, 2018. 2 pages. [Original].
Exhibit A to Jun. 22, 2018 Response: Karkowsky, Abraham. "Summary Review: NDA 203109 Sildenafil Citrate Powder for Reconstitution." *Drugs@FDA: FDA Approved Drug Products*, US Food & Drug Administration, Reference ID: 3131055. May 15, 2012, 20 pages. www.accessdata.fda.gov/drugsatfda_docs/nda/2012/203109Orig1s000SumR.pdf.
Exhibit B to Jun. 22, 2018 Response: "Labeling-Package Insert: NDA 203109 Sildenafil Citrate Powder for Reconstitution." *Drugs@FDA: FDA Approved Drug Products*, US Food & Drug Administration, Reference ID: 3471998. Mar. 11, 2014, 31 pages. www.accessdata.fda.gov/drugsatfda_docs/label/2014/021845s011,022473s004,0203109s002lbl.pdf.
Exhibit C to Jun. 22, 2018 Response: Sung, Hyun Hwan, and Sung Won Lee. "Chronic Low Dosing of Phosphodiesterase Type 5 Inhibitor for Erectile Dysfunction." *Korean Journal of Urology*, vol. 53, No. 6, 2012, pp. 377-385, doi:10.4111/kju.2012.53.6.377.
Exhibit D to Jun. 22, 2018 Response: Anderson, Page A. W., et al. "The Fontan Patient: Inconsistencies in Medication Therapy Across Seven Pediatric Heart Network Centers." *Pediatric Cardiology*, vol. 31, No. 8, 2010, pp. 1219-1228. doi:10.1007/s00246-010-9807-5.
Gewillig, Marc, and David J. Goldberg. "Failure of the Fontan Circulation." *Heart Failure Clinics*, vol. 10, No. 1, 2014, pp. 105-116. doi:10.1016/j.hfc.2013.09.010.
Hebert, A., et al. "Bosentan Improves Exercise Capacity in Adolescents and Adults After Fontan Operation: The TEMPO (Treatment With Endothelin Receptor Antagonist in Fontan Patients, a Randomized, Placebo-Controlled, Double-Blind Study Measuring Peak Oxygen Consumption) Study." *Circulation*, vol. 130, No. 23, 2014, pp. 2021-2030. doi:10.1161/circulationaha.113.008441.
Kouvelas, D., et al. "PDE5 Inhibitors: In Vitro and In Vivo Pharmacological Profile." *Current Pharmaceutical Design*, vol. 15, No. 30, 2009, pp. 3464-3475. doi:10.2174/138161209789206971.
New Zealand Further Examination Report for Application No. 727653 dated Apr. 24, 2018. 7 pages.
Rhodes, Jonathan, et al. "Effect of inhaled Iloprost on the exercise function of Fontan patients: A demonstration of concept." *International Journal of Cardiology*, vol. 168, No. 3, 2013, pp. 2435-2440. doi:10.1016/j.ijcard.2013.03.014.
Rogers, Lindsay S., et al. "18 Years of the Fontan Operation at a Single Institution." *Journal of the American College of Cardiology*, vol. 60, No. 11, 2012, pp. 1018-1025., doi:10.1016/j.jacc.2012.05.010.
Schuuring, Mark J., et al. "Impact of bosentan on exercise capacity in adults after the Fontan procedure: a randomized controlled trial." *European Journal of Heart Failure*, vol. 15, No. 6, 2013, pp. 690-698., doi:10.1093/eurjhf/hft017.
Shon, Ji-Hong, et al. "The disposition of three phosphodiesterase type 5 Inhibitors, vardenafil, sildenafil, and udenafil, is differently influenced by the CYP3A5 genotype." *Pharmacogenetics and Genomics*, vol. 21, No. 12, 2011, pp. 820-828., doi:10.1097/fpc.0b013e32834b79e6.
Singapore Search Report and Written Opinion for Application No. 11201700060W dated Feb. 26, 2018. 9 pages.
Exhibit i-3 to Declaration: "Dona-A Pharmatech IR report" (Jan. 2012). [English Translation].
Australian Notice of Acceptance for Patent Application No. 2015302271 dated Feb. 19, 2019 (4 pages).
Canadian Office Action for Patent Application No. 2,954,183 dated Feb. 4, 2019 (3 pages).
Chinese Office Action for Patent Application No. 201580040518.0 dated Feb. 19, 2019 (10 pages). [Original].
Chinese Office Action for Patent Application No. 201580040518.0 dated Feb. 19, 2019 (15 pages). [English Translation].
Zou et al., "Status and Analysis of Worldwide New Drugs," Second Military Medical University Press, first edition, first print, p. 250.
Zou et al., "Status and Analysis of Worldwide New Drugs," Second Military Medical University Press, first edition, first print, p. 250. [English Translation].
Colombian Office Action for Patent Application No. NC2017/0000271 (dated Oct. 4, 2018) (6 pages). [Original].
Colombian Office Action for Patent Application No. NC2017/0000271 (dated Oct. 4, 2018) (6 pages). [English Translation].
Dominican Republic Office Action for Patent Application No. P2017-0014 dated Jan. 23, 2019 (3 pages). [Original].
Dominican Republic Office Action for Patent Application No. P2017-0014 dated Jan. 23, 2019 (3 pages). [English Translation].
Ecuador Opposition Notice for Patent Application No. IEPI 2017-15154 dated Nov. 30, 2018 (12 pages). [Original].
Ecuador Opposition Notice for Patent Application No. IEPI 2017-15154 dated Nov. 30, 2018 (12 pages). [English Translation].
Indian First Examination Report for Patent Application No. 201617043929 dated Feb. 22, 2019 (6 pages).
Japanese Decision of Final Refusal for Patent Application No. 2017-504434, dated Oct. 2, 2018 (7 pages). [Original].
Japanese Decision of Final Refusal for Patent Application No. 2017-504434, dated Oct. 2, 2018 (7 pages). [English translation].
ClinicalTrials.gov archive—View of NCT02201342 on Jul. 25, 2014, available at https://clinicaltrials.gov/archive/NCT02201342/2014_07_25, accessed on Feb. 19, 2018.
Zarin et al., "The ClinicalTrials.gov Results Database—Update and Key Issues," The New England Journal of Medicine 2011, 364;9, pp. 852-860.
ClinicalTrials.gov archive—History of Changes for Study: NCT02201342, available at https://clinicaltrials.gov/ct2/history/NCT02201342?A=1&B=2&C=merged#StudyPageTop, accessed on Sep. 14, 2018.
ClinicalTrials.gov—Key Record Dates, available at https://clinicaltrials.gov/ct2/keydates/NCT02201342, accessed on Sep. 14, 2018.
Korean Office Action for Patent Application No. 10-2017-7006695 dated Sep. 18, 2018 (3 pages). [Original].
Korean Office Action for Patent Application No. 10-2017-7006695 dated Sep. 18, 2018 (3 pages). [English Translation].
Panamanian Report on the State of the Art Edict No. 563 for Patent Application No. 91474-01 dated Oct. 18, 2018 (5 pages). [Original].
Panamanian Report on the State of the Art Edict No. 563 for Patent Application No. 91474-01 dated Oct. 18, 2018 (6 pages). [English Translation].
Saudi Arabia Examination Report Notification Regarding Form for Patent Application No. 517380879 dated Jan. 2, 2019 (2 pages). [Original].
Saudi Arabia Examination Report Notification Regarding Form for Patent Application No. 517380879 dated Jan. 2, 2019 (2 pages). [English Translation].
Singapore Written Opinion for Patent Application No. 11201700060W dated Jan. 7, 2019 (7 pages).
Trojnarska et al., Challenges of management and therapy in patients with a functionally single ventricle after Fontan operation. Cardiol J. 2011;18(2):119-27.
Tunisian Office Action for Application No. TN2017/0029 dated Sep. 27, 2017. [English Translation].
Tunisian Office Action for Application No. TN2017/0029 dated Sep. 27, 2017. [Original].
Uzun et al., Resolution of protein-losing enteropathy and normalization of mesenteric Doppler flow with sildenafil after Fontan. Ann Thorac Surg. Dec. 2006;82(6):e39-40.
Park et al., Udenafil improves exercise capacity in patients with chronic obstructive pulmonary disease: a prospective study. COPD Aug. 2012; 9(5): 499-504.
Exhibit m to Declaration: Correspondence regarding company presentation submitted to analysts by Youn-Tek Song (IR Team/Manager for Mezzion Pharma) on behalf of Mezzion by e-mail on Mar. 26, 2014 for the purpose of an Analyst Conference Call [Korean Original followed by English Translation].
Fernandes et al., Serial cardiopulmonary exercise testing in patients with previous Fontan surgery. Pediatr Cardiol. Feb. 2010;31(2):175-80.

(56) References Cited

OTHER PUBLICATIONS

Fontan et al., Surgical repair of tricuspid atresia. Thorax. May 1971;26(3):240-8.
Frommelt et al., Doppler assessment of pulmonary artery flow patterns and ventricular function after the Fontan operation. Am J Cardiol. Nov. 1, 1991;68(11)1211-5.
Galie et al., Sildenafil citrate therapy for pulmonary arterial hypertension. N Engl J Med. Nov. 17, 2005;353(20):2148-57.
Galie et al., Tadalafil therapy for pulmonary arterial hypertension. Circulation. Jun. 9, 2009;119(22):2894-903.
Gewillig et al., The Fontan circulation: who controls cardiac output? Interact Cardiovasc Thorac Surg. Mar. 2010;10(3):428-33.
Giardini et al., Natural history of exercise capacity after the Fontan operation: a longitudinal study. Ann Thorac Surg. Mar. 2008;85(3):818-21.
Giardini et al., Usefulness of cardiopulmonary exercise to predict long-term prognosis in adults with repaired tetralogy of Fallot. Am J Cardiol. May 15, 2007;99(10):1462-7.
Goldberg et al., Abstract 2161: Sildenafil Improves Ventricular Performance in Children and Young Adults After the Fontan Operation. Circulation. 2009;120:S603.
Goldstein et al., Relation of systemic venous return, pulmonary vascular resistance, and diastolic dysfunction to exercise capacity in patients with single ventricle receiving fontan palliation. Am J; Cardiol. Apr. 15, 2010;105(8):1169-75.
Goldstein et al., Usefulness of peripheral vascular function to predict functional health status in patients with Fontan circulation. Am J Cardiol. Aug. 1, 2011;108(3):428-34.
Guazzi et al., PDE5 inhibition with sildenafil improves left ventricular diastolic function, cardiac geometry, and clinical status in patients with stable systolic heart failure: results of a 1-year, prospective, randomized, placebo-controlled study. Circ Heart Fail. Jan. 2011;4(1):8-17.
Guazzi et al., Pulmonary hypertension in heart failure with preserved ejection fraction: a target of phosphodiesterase-5 inhibition in a 1-year study. Circulation. Jul. 12, 2011;124(2):164-74.
Haseyama et al., Pulmonary vasodilation therapy with sildenafil citrate in a patient with plastic bronchitis after the Fontan procedure for hypoplastic left heart syndrome. J Thorac Cardiovasc Surg. Nov. 2006;132(5):1232-3.
Hosein et al., Factors influencing early and late outcome following the Fontan procedure in the current era. The 'Two Commandments'? Eur J Cardiothorac Surg. Mar. 2007;31(3):344-52.
Huddleston et al., Sildenafil for the treatment of pulmonary hypertension in pediatric patients. Pediatr Cardiol. Oct. 2009;30(7):871-82.
Humpl et al., Beneficial effect of oral sildenafil therapy on childhood pulmonary arterial hypertension: twelve-month clinical trial of a single-drug, open-label, pilot study. Circulation. Jun. 21, 2005;111(24):3274-80.
Inai et al., Skeletal muscle hemodynamics and endothelial function in patients after Fontan operation. Am J Cardiol. Mar. 15, 2004;93(6):792-7.
Jenkins et al., Decreased exercise performance with age in children with hypoplastic left heart syndrome. J Pediatr. Apr. 2008;152(4):507-12.
Jin et al., Impaired vascular function in patients with Fontan circulation. Int J Cardiol. Aug. 21, 2007;120(2):221-6.
Kaneko et al., Single right ventricles have impaired systolic and diastolic function compared to those of left ventricular morphology. J Am Soc Echocardiogr. Nov. 2012;25(11):1222-30.
Keteyian et al., Reproducibility of peak oxygen uptake and other cardiopulmonary exercise parameters: implications for clinical trials and clinical practice. Chest. Oct. 2010;138(4):950-5.
Kim et al., DA-8159: Erectogenic. Drugs of the Future. 2005;30(7):678-82.
Kim et al., ULTIMATE-SHF trial (UdenafiL Therapy to Improve symptoMAtology, exercise Tolerance and hEmodynamics in patients with chronic systolic heart failure): study protocol for a randomized, placebo-controlled, double-blind trial. Trials. Jun. 22, 2013;14:188.
Kruger et al., Protein kinase G modulates human myocardial passive stiffness by phosphorylation of the titin springs. Circ Res. Jan. 2, 2009;104(1):87-94.
La Gerche et al., What Limits Cardiac Performance during Exercise in Normal Subjects and in Healthy Fontan Patients? Int J Pediatr. 2010;2010.
Mahle et al., Endothelial function following the Fontan operation. Am J Cardiol. May 15, 2003;91(10):1286-8.
Manlhiot et al., Functional health status of adolescents after the Fontan procedure—comparison with their siblings. Can J Cardiol. Sep. 2009;25(9):e294-300.
McCrindle et al., Laboratory measures of exercise capacity and ventricular characteristics and function are weakly associated with functional health status after Fontan procedure. Circulation. Jan. 5, 2010;121(1):34-42.
McCrindle et al., Relationship of patient and medical characteristics to health status in children and adolescents after the Fontan procedure. Circulation. Feb. 28, 2006;113(8):1123-9.
Moroccan Office Action for Application No. 40095 dated Aug. 9, 2017 [English Translation].
Moroccan Office Action for Application No. 40095 dated Aug. 9, 2017 [Original].
Mourani et al., Effects of long-term sildenafil treatment for pulmonary hypertension in infants with chronic lung disease. J Pediatr. Mar. 2009;154(3):379-84, 384.e1-2.
Nagayama et al., Sildenafil stops progressive chamber, cellular, and molecular remodeling and improves calcium handling and function in hearts with pre-existing advanced hypertrophy caused by pressure overload. J Am Coll Cardiol. Jan. 13, 2009;53(2)207-15.
Ono et al., Clinical outcome of patients 20 years after Fontan operation—effect of fenestration on late morbidity. Eur J Cardiothorac Surg. Dec. 2006;30(6):923-9.
Panamanian Office Action for Application No. 91474 dated Apr. 20, 2017. [English Translation].
Panamanian Office Action for Application No. 91474 dated Apr. 20, 2017. [Original].
Pardon et al., A cross-sectional study of exercise performance during the first 2 decades of life after the Fontan operation. J Am Coll Cardiol. Jul. 8, 2008;52(2):99-107.
Pundi et al., 40-Year Follow-Up After the Fontan Operation: Long-Term Outcomes of 1,052 Patients. J Am Coll Cardiol. Oct. 13, 2015;66(15):1700-10.
Rhodes et al., Non-geometric echocardiographic indices of ventricular function in patients with a Fontan circulation. J Am Soc Echocardiogr. Nov. 2011;24(11):1213-9.
Sanghavi et al., Determinants of exercise function following univentricular versus biventricular repair for; pulmonary atresia/intact ventricular septum. Am J Cardiol. Jun. 1, 2006;97(11):1638-43.
Sano et al., Assessment of ventricular contractile state and function in patients with univentricular heart. Circulation. Jun. 1989;79(6):1247-56.
Santos et al., Tadalafil-induced improvement in left ventricular diastolic function in resistant hypertension. Eur J Clin Pharmacol. Feb. 2014;70(2):147-54.
Schilling et al., The Fontan epidemic: Population projections from the Australia and New Zealand Fontan Registry. Int J Cardiol. Sep. 15, 2016;219:14-9.
Snarr et al., Pulmonary vasodilator therapy in the failing Fontan circulation: rationale and efficacy. Cardiol Young. Dec. 2015;25(8):1489-92.
Stickland et al., Does fitness level modulate the cardiovascular hemodynamic response to exercise? J Appl Physiol (1985). Jun. 2006;100(6):1895-901.
Takimoto et al., Chronic inhibition of cyclic GMP phosphodiesterase 5A prevents and reverses cardiac hypertrophy. Nat Med. Feb. 2005;11(2):214-22.
Takimoto et al., Compartmentalization of cardiac beta-adrenergic inotropy modulation by phosphodiesterase type 5. Circulation. Apr. 24, 2007;115(16):2159-67.
Thacker et al., Use of oral budesonide in the management of protein-losing enteropathy after the Fontan operation. Ann Thorac Surg. Mar. 2010;89(3):837-42.

(56) References Cited

OTHER PUBLICATIONS

ClinicalTrials.gov—A Service of the U.S. National Institutes of Health, Fontan Udenafil Exercise Longitudinal Assessment Trial (FUEL), Jul. 21, 2016, 4 pages.
ClinicalTrials.gov—A Service of the U.S. National Institutes of Health, Pharmacokinetic/Pharmacodynamic Study of Udenafil in Adolescent, Apr. 10, 2015, 4 pages.
ClinicalTrials.gov—A Service of the U.S. National Institutes of Health, Changes to NCT02201342 o Apr. 26, 2015, 3 pages.
Kim et al., "Mezzion Pharma Announces Collaboration with New England Research Institutes to evaluate Udenafil in Adolescents with Single Ventricle Heart Defects", Jan. 10, 2014, 2 pages.
W.M. Gersony, "Fontan Operation After 3 Decades, What We Have Learned", Circulation, vol. 117, pp. 13-15 (2008).
J. Rychik, "Forty Years of the Fontan Operatiton: A Failed Strategy", Pediatric Cardiac Surgery Annual, pp. 96-100 (2010).
Goldberg et al., "Impact of Oral Sildenafil on Exercise Performance in Children and Young Adults After the Fontan Operation", Circulation, vol. 123, pp. 1185-1193 (2011).
Shabanian et al., "Sildenafil and ventriculo-arterial coupling in Fontan-palliated patients: a noninvasive echocardiographic assessment", Pediatr. Cardiol, 34(1), pp. 129-134 (2013—Abstract.
Menon et al., "Single-Ventricle Cardiology: Palliation, Care and Resource Utilization", Circulation, 128:A16024, 2 pages (2013)—Abstract.
Sabri et al., "Comparison of the therapeutic and side effects of tadalafil and sildenafil in childrent and adolescents with pulmonary arterial hypertension", Pediatr. Cardiol., 35(4), pp. 699-704 (2014)—Abstract.
Boolell et all., "Sildenafil: an orally active type 5 cyclic GMP-specific phosphodiesterase inhibitor for the treatment of penile erectile dysfunction", Int'l J. Impot. Res., 8:47 (1996)—Abstract.
Martin et al., "The Challenge of Patient Adherence", Ther. Clin. Risk Manag., 1(3), pp. 189-199 (2005).
Gu Kang et al., "Udenafil: efficacy and tolerability in the management of erectile dysfunction", Ther. Adv. Urol., 5(2), pp. 101-110 (2013).
Sabri et al., "Effect of Tadalafil on Myocardial and Endothelial Function and Excerise Performance After Modified Fontan Operation", Pediatr. Cardiol., vol. 37, pp. 55-61 (2016).
Written Opinion issued in related International Patent Application No. PCT/US2015/038638, dated Sep. 22, 2015.
Zhao et al., "Efficacy and safety of once-daily dosing of udenafil in the treatment of erectile dysfunction: results of a multicenter, randomized, double-blind, placebo-controlled trial", Eur. J. of Urology, 60:380-387 (2011)—Abstract.
Akagi et al., Influence of ventricular morphology on diastolic filling performance in double-inlet ventricle after the Fontan procedure. J Am Coll Cardiol. Dec. 1993;22(7):1948-52.
Andersen et al., Sildenafil and diastolic dysfunction after acute myocardial infarction trial: rationale and design. Clin Cardiol. Apr. 2013;36(4):179-83.
Anderson et al., Contemporary outcomes after the Fontan procedure: a Pediatric Heart Network multicenter study. J Am Coll Cardiol. Jul. 8, 2008;52(2):85-98.
Argiento et al., Exercise stress echocardiography for the study of the pulmonary circulation. Eur Respir J. Jun. 2010;35(6):1273-8.
Attina et al., Phosphodiesterase type 5 inhibition reverses impaired forearm exercise-induced vasodilatation in hypertensive patients. J Hypertens. Mar. 2008;26(3):501-7.
Avitabile et al., A multifaceted approach to the management of plastic bronchitis after cavopulmonary palliation. Ann Thorac Surg. Aug. 2014;98(2):634-40.
Barst et al., STARTS-2 Investigators. STARTS-2: long-term survival with oral sildenafil monotherapy in treatment-naive pediatric pulmonary arterial hypertension. Circulation. May 13, 2014;129(19):1914-23.

Behling et al., Effects of 5'-phosphodiesterase four-week long inhibition with sildenafil in patients with; chronic heart failure: a double-blind, placebo-controlled clinical trial. J Card Fail. Apr. 2008;14(3):189-97.
Binotto et al., Altered endothelial function following the Fontan procedure. Cardiol Young. Feb. 2008;18(1):70-4.
Blum, A. Treating heart failure with sildenafil. Congest Heart Fail. Jul.-Aug. 2009;15(4):181-5.
Canter et al., Indications for heart transplantation in pediatric heart disease: a scientific statement from the American Heart Association Council on Cardiovascular Disease in the Young; the Councils on Clinical Cardiology, Cardiovascular Nursing, and Cardiovascular Surgery and Anesthesia; and the Quality of Care and Outcomes Research Interdisciplinary Working Group. Circulation. Feb. 6, 2007;115(5):658-76.
Cheung et al., Serial assessment of left ventricular diastolic function after Fontan procedure. Heart. Apr. 2000;83(4):420-4.
Ciliberti et al., Modulation of pulmonary vascular resistance as a target for therapeutic interventions in Fontan patients: focus on phosphodiesterase inhibitors. Future Cardiol. Mar. 2012;8(2):271-84.
Colombian Office Action for Application No. NC2017/0000271 [English Translation].
Colombian Office Action for Application No. NC2017/0000271 [Original].
Deal et al., Management of the failing Fontan circulation. Heart. Jul. 2012;98(14):1098-104.
Diller et al., Exercise intolerance in adult congenital heart disease: comparative severity, correlates, and prognostic implication. Circulation. Aug. 9, 2005;112(6):828-35.
Diller et al., Predictors of morbidity and mortality in contemporary Fontan patients: results from a multicenter study including cardiopulmonary exercise testing in 321 patients. Eur Heart J. Dec. 2010;31(24):3073-83.
d'Udekem et al., How good is a good Fontan? Quality of life and exercise capacity of Fontans without arrhythmias. Ann Thorac Surg. Dec. 2009;88(6):1961-9.
Eurasian Office Action and Search Report for Application No. 201692518 dated Jul. 20, 2017 [English Translation].
Eurasian Office Action and Search Report for Application No. 201692518 dated Jul. 20, 2017 [Original].
Exhibit b-1 to Declaration of James L. Yeager and Won Geun Kim Under 37 CFR § 1.130, dated Jul. 30, 2017 (referred to herein as "Declaration"): Press release entitled "Mezzion Pharma Announces Collaboration with New England Research Institutes to Evaluate Udenafil in Adolescents with Single Ventricle Heart Defects" (Jan. 10, 2014).
Exhibit c-2 to Declaration: Mezzion report entitled "Company Report, Mezzion (140410)" (Aug. 13, 2013).
Exhibit c-3 to Declaration: Mezzion report entitled "Mezzion Investor Relations" (Jul. 2013).
Exhibit c-4 to Declaration: Mezzion report entitled "Mezzion Investor Relations" (Jun. 2014), [English translation of Exhibit c-3 in part].
Exhibit i-2 to Declaration: Press release entitled "Zydena in the United States acquired the patent applications for the enlarged Benign prostatic hyperplasia treatment effect" (Jan. 9, 2014).
Exhibit i-3 to Declaration: Mezzion report entitled "Dong-A Pharmtech IR report" (Jan. 2012).
Exhibit i-4 to Declaration: Press release entitled "Zydena, Approved by the Ethics Committee in Mexico" (Jul. 23, 2012).
Exhibit i-5 to Declaration: Press release entitled "Dong-A Pharmtech, Russia Market Second development export after 2007" (May 16, 2012).
Exhibit j-2 to Declaration: Press release entitled "Mezzion, return exclusive rights (develop and marketing) to erectile dysfunction and Benign prostatic hyperplasia in the Americas" (Mar. 31, 2015).
Exhibit k-2 to Declaration: Press release entitled Mezzion, completes to ½ Clinical Trials of Udenafil in Fontan patients (Mar. 16, 2015).

(56) References Cited

OTHER PUBLICATIONS

Exhibit k-3 to Declaration: Press release entitled "Mezzion Pharma Announces Collaboration with New England Research Institutes to Evaluate Udenafil in Adolescents with Fontan Surgery" (Jan. 10, 2014).
Exhibit k-4 to Declaration: Press release entitled "Mezzion, submit uses patent application for Fontan Operation" (Jun. 29, 2015).
Exhibit I to Declaration: Correspondence to reporter Hyoung-Su Park of Edaily by Youn-Tack Song (IR Team/Manager for Mezzion Pharma) on behalf of Mezzion by e-mail on Mar. 26, 2014 for the purpose of an analyst report [Korean Original followed by English Translation].
Australian Examination Report dated Feb. 21, 2018, for Australian Patent Application No. 2015302271, 4 pages.
Ukrainian Office Action dated Jan. 16, 2018, for Ukrainian Patent Application No. 2016 13574, 4 pages.
English Translation of the Ukrainian Office Action dated Jan. 16, 2018, for Ukrainian Patent Application No. 2016 13574, 4 pages.
European Search Report dated Jan. 4, 2018, for European Patent Application No. 15831606.7, filed Jun. 30, 2015, 12 pages.
Exhibit c-3 to Declaration: Mezzion report entitled "Mezzion Investor Relations" (Jul. 2013) [English Translation].
Kim, K-H et al. (Apr. 1, 2014). "Udenafil Improves Exercise Capacity and Left Ventricular Remodeling in Patients with Systolic Heart Failure," *Journal of the American College of Cardiology* 63(12), 1 page.
Kim, H-L. et al. (Sep. 2015, e-published Apr. 2, 2015). "Therapeutic Effects of Udenafil on Pressure-Overload Cardiac Hypertrophy," *Hypertens Res* 38(9):597-604.
Kim, K. et al. (Apr. 1, 2015). PDE 5 Inhibition with Udenafil Improves Left Venticular Systolic/Diastolic Function and Exercise Capacity in Patients with Chronic Systolic Heart Failure: A 12-Week, Randomized, Double-Blind, Placebo-Controlled Trial (Udenafil Therapy to Improve Symptomatology, Exercise Tolerance and Hemodynamics in Patients with Chronic Systolic Heart Failure), *The Journal of Heart and Lung Transplanation* 34(4):S156.
Morchi et al., Sildenafil Increases Systemic Saturation and Reduces Pulmonary Artery Pressure in Patients with Failing Fontan Physiology. Congenit Heart Dis. Apr. 2009; 4(2):107-111.
Shabanian, R. et al. (Jan. 2013, e-published Aug. 5, 2012). "Sildenafil and ventriculo-arterial coupling in Fontan-palliated patients: a noninvasive echocardiographic assessment," *Pediatr Cardiol* 34(1):129-134.
Goldberg et al., "Results of the Fontan Udenafil Exercise Longitudinal (FUEL) Trial," Circulation. (https://doi.org/10.1161/CIRCULATIONAHA.119.044352), Jan. 2020.
Canadian Office Action for Patent Application No. 2954183 dated Nov. 18, 2019 (3 pages).
Chinese Office Action for Patent Application No. 201580040518.0 dated Nov. 25, 2019 (3 pages). [Original].
Chinese Office Action for Patent Application No. 201580040518.0 dated Nov. 25, 2019 (6 pages). [English Translation].
Colombian Office Action for Patent Application No. NC2017/0000271 dated Apr. 4, 2019 (6 pages). [Original].
Colombian Office Action for Patent Application No. NC2017/0000271 dated Apr. 4, 2019 (6 pages). [English Translation].
Japanese Office Action for Patent Application No. 2019-017645 dated Jan. 14, 2020 (4 pages). [Original].
Japanese Office Action for Patent Application No. 2019-017645 dated Jan. 14, 2020 (5 pages). [English Translation].
Pim Parts and Ceramics Debinding Process & Supercritical CO2 Equipment, Separex, Aug. 30, 2011, p. 1 and 2, URL: http://www.separex.fr/download/category/8-applications.html?download=2:ceramics-debinding-applications [as cited in Cite. No. 7 above; URL apparently inactive].
Taiwanese Office Action and Search Report for Patent Application No. 108138688 dated Jan. 3, 2020 (4 pages). [Original].
Taiwanese Office Action and Search Report for Patent Application No. 108138688 dated Jan. 3, 2020 (6 pages). [English Translation].
Australian Certificate of Grant for Patent Application No. 2015302271 dated Jun. 13, 2019 (1 page).
Chilean Office Action for Patent Application No. 201700329 dated May 27, 2019 (10 pages). [Original].
Chilean Office Action for Patent Application No. 201700329 dated May 27, 2019 (10 pages). [English Translation].
Colombian Office Action for Patent Application No. NC2017/0000271 dated Sep. 4, 2019 (4 pages). [Original].
Colombian Office Action for Patent Application No. NC2017/0000271 dated Sep. 4, 2019 (4 pages). [English Translation].
European Office Action for Patent Application No. 15831606.7 dated Apr. 26, 2019 (6 pages).
Israeli Office Action for Patent Application No. 250547 dated Jul. 30, 2019 (4 pages). [Original].
Israeli Office Action for Patent Application No. 250547 dated Jul. 30, 2019 (4 pages). [English Translation].
Japanese Office Action for Patent Application No. 2017-504434 dated Jul. 23, 2019 (14 pages). [Original].
Japanese Office Action for Patent Application No. 2017-504434 dated Jul. 23, 2019 (13 pages). [English Translation].
Korean Office Action for Patent Application No. 10-2017-7006695 dated Jul. 22, 2019 (7 pages). [Original].
Korean Office Action for Patent Application No. 10-2017-7006695 dated Jul. 22, 2019 (5 pages). [English Translation].
ClinicalTrials.gov Search Results Jul. 1, 2019: NCT02201342, Pharmacokinetic/Pharmacodynamic Study of Udenafil in Adolescents.
Taiwanese Office Action and Search Report for Patent Application No. 104121758 dated Apr. 8, 2019 (5 pages). [Original].
Taiwanese Office Action and Search Report for Patent Application No. 104121758 dated Apr. 8, 2019 (7 pages). [English Translation].
Kim et al., "Safety, tolerability and pharmacokinetics of udenafil, a novel PDE-5 inhibitor, in healthy young Korean subjects," Br. J. Clin. Pharmacol. 65:6, pp. 848-854, (2008).
Ukrainian Notice of Decision to Grant for Patent Application No. a201613574 dated Feb. 15, 2019 (7 pages). [Original].
Ukrainian Notice of Decision to Grant for Patent Application No. a201613574 dated Feb. 15, 2019 (6 pages). [English Translation].

Note: data are presented as mean (range). Concentration unit is ng/mL

| Time (hr) | 37.5 mg q24h | 37.5 mg q12h | 87.5 mg q24h | 87.5 mg q12h | 125 mg q24h |
|---|---|---|---|---|---|
| 0 | 10.7 (6.07 – 15.5) | 59.4 (19 – 95.7) | 33.4 (18.7 – 52.2) | 172.2 (117 – 302) | 43.0 (23.4 – 84.4) |
| 0.25 | 13.3 (6.68 – 28.2) | 60.6 (20.7 – 100) | 31.0 (17.6 – 45.2) | 160.8 (118 – 200) | 51.8 (21.6 – 115) |
| 0.5 | 19.8 (6.39 – 42) | 93.9 (32.9 – 152) | 50.3 (24.8 – 102) | 252.7 (125 – 439) | 147.5 (24.7 – 486) |
| 1 | 55.5 (20.6 – 88.8) | 129.6 (67.6 – 189) | 129.6 (41.9 – 298) | 384.2 (239 – 623) | 266.3 (32.8 – 450) |
| 1.5 | 65.5 (40.4 – 95.7) | 136.3 (87.8 – 200) | 207.6 (51.4 – 427) | 453.2 (250 – 837) | 348.8 (90.8 – 721) |
| 2 | 64.1 (49.5 – 109) | 126.8 (82.4 – 173) | 213.5 (90.2 – 401) | 390.6 (293 – 605) | 385.7 (226 – 738) |
| 3 | 81.7 (36.6 – 174) | 124.0 (82.3 – 180) | 226.7 (140 – 382) | 394.2 (308 – 650) | 308.7 (206 – 572) |
| 4 | 59.7 (33.4 – 111) | 106.4 (64.4 – 152) | 184.7 (144 – 298) | 342.0 (283 – 479) | 270.3 (198 – 481) |
| 6 | 57.4 (26.9 – 127) | 86.2 (47.7 – 144) | 133.3 (109 – 185) | 270.3 (226 – 367) | 200.0 (141 – 370) |
| 8 | 40.6 (23.5 – 68.6) | 67.3 (42 – 104) | 105.9 (76 – 147) | 227.5 (180 – 277) | 153.9 (99.3 – 318) |
| 12 | 28.8 (16.7 – 50.3) | 53.7 (29.5 – 97.6) | 69.3 (49.1 – 92.5) | 142.0 (118 – 188) | 101.4 (56.3 – 199) |
| 24 | 12.4 (7.04 – 21.5) | 27.6 (16.1 – 48.8) | 32.9 (20.8 – 45.3) | 65.3 (46.9 – 92) | 47.2 (21.8 – 111) |
| 48 | 4.0 (2.4 – 5.56) | 8.4 (5.33 – 15) | 9.8 (6.46 – 12.3) | 14.7 (9.71 – 22.4) | 14.8 (3.36 – 27) |

Figure 28

| Parameters | 37.5 mg q24h | 37.5 mg q12h | 87.5 mg q24h | 87.5 mg q12h | 125 mg q24h |
|---|---|---|---|---|---|
| $C_{max}$ (ng/mL) | 95 ± 46 | 152 ± 46 | 277 ± 107 | 506 ± 188 | 438 ± 173 |
| $T_{max}$ (hr) | 2.3 ± 0.9 | 1.5 ± 0.8 | 2.1 ± 0.7 | 1.3 ± 0.3 | 1.6 ± 0.7 |
| $AUC_\tau$ (ng·hr/mL) | 835 ± 404 | 1053 ± 387 | 2199 ± 457 | 3350 ± 796 | 3249 ± 1729 |
| $AUC_{0-24}$ (ng·hr/mL) | 835 ± 404 | 2107 ± 774 | 2199 ± 457 | 6701 ± 1591 | 3249 ± 1729 |
| CL/F (L/hr) | 53.2 ± 21.2 | 39.8 ± 14.3 | 41.1 ± 7.7 | 27.1 ± 5.4 | 45.3 ± 16.3 |
| V/F (L) | 1027 ± 508 | 770 ± 297 | 751 ± 168 | 411 ± 101 | 617 ± 188 |
| $k_e$ ($hr^{-1}$) | 0.056 ± 0.012 | 0.053 ± 0.006 | 0.055 ± 0.004 | 0.067 ± 0.008 | 0.076 ± 0.029 |
| $T_{1/2}$ (hr) | 12.9 ± 3.1 | 13.3 ± 1.5 | 12.6 ± 0.9 | 10.4 ± 1.2 | 10.2 ± 3.4 |

The calculations for CL/F or V/F have been adjusted according to the equations below:

$CL/F = Dose / AUC\tau$ $V/F = CL/F / k_e$

Figure 29

METHODS OF IMPROVING MYOCARDIAL PERFORMANCE IN FONTAN PATIENTS USING UDENAFIL COMPOSITIONS

CROSS REFERENCE TO RELATED APPLICATION

The present application is a continuation application of the U.S. patent application Ser. No. 14/788,211 filed Jun. 30, 2015, which claims priority to U.S. Provisional Patent Application No. 62/036,506, filed Aug. 12, 2014, and U.S. Provisional Patent Application No. 62/186,132, filed Jun. 29, 2015, the disclosures of which are specifically incorporated herein by reference in their entireties.

STATEMENT OF GOVERNMENT INTERESTS

This work was funded, at least in part, by grants from the National Heart, Lung, and Blood Institute (NHLBI) of the US National Institutes of Health. The principal grant support was through NHLBI grant U24 HL135691 and/or U01 HL068270 to the New England Research Institutes, Inc. Grants to the Pediatric Heart Network clinical sites (UG1 HL135685, UG1 HL135680, UG1 HL135683, UG1 HL135689, UG1 HL135682, UG1 HL135665, UG1 HL135646, UG1 HL135678, UG1 HL135666) supported a small percentage of the trial activities at the sites. The government may have certain rights in the data and inventions disclosed herein.

FIELD OF THE INVENTION

The present invention relates generally to the field of using phosphodiesterase E5 (PDE5) inhibitors in patients who have undergone the Fontan operation. In particular, the PDE5 inhibitor is udenafil or a pharmaceutically acceptable salt thereof.

BACKGROUND OF THE INVENTION

I. Background Regarding the Fontan Procedure

The Fontan procedure, or Fontan/Kreutzer procedure, is a palliative surgical procedure for children born with functional single ventricle congenital heart disease. The Fontan operation was designed to provide blood flow in series to the pulmonary and systemic circulation without the requirement for a right ventricular pumping chamber. The operation allows systemic venous blood to flow directly into the pulmonary circulation on the basis of a single ventricular impetus through the arteries, capillaries, and systemic venous system. This arrangement has improved life expectancy for patients with single-ventricle and pulmonary-outflow obstruction compared with previous arterial shunts.

The operation, which creates a total cavopulmonary connection, separates the systemic and pulmonary circuits and eliminates both hypoxemia and ventricular volume overload. However, following the Fontan operation there is no ventricular pump to propel blood into the pulmonary arteries. Instead, blood returns to the lungs via passive flow from the systemic veins. This results in a circulation characterized by elevated central venous pressure, abnormal pulmonary vascular resistance, and a chronically low cardiac output. Over time, these inherent characteristics of Fontan physiology result in a predictable, persistent deterioration of cardiovascular efficiency, as marked by a progressive decline in exercise performance that begins after puberty. This decline in exercise capacity correlates with an increase in symptoms from cardiovascular dysfunction and may result in the need for hospitalization, escalation of heart failure management, or transplant.

Those with the Fontan circulation do not have 'normal' heart physiology or functioning. Two major complications that might have many "downstream" effects are the following effects on increasing ("hypertension") and decreasing ("hypotension") blood pressure depending upon its location (veins or arteries). First, with Fontan circulation, there is "systemic venous hypertension", which means that the blood pressure in the veins (blood going back to the heart) in the body is higher than in individuals with normal heart function (not Fontan circulation). There are many negative consequences that may be caused by systemic venous hypertension (congestive heart failure, edema or swelling, dysfunction of the liver, potentially protein-losing enteropathy) that are basically related to the distribution of fluids in the body. A second complication is "pulmonary arterial hypotension" where the blood pressure in arteries going towards or in the lungs (hence pulmonary) is lower than in individuals with normal heart function. There are also a number of negative consequences associated with pulmonary arterial hypotension such as cyanosis (blue lips) or lack of exercise capacity. Many of the subsequent medical conditions and deaths that follow the Fontan procedure (either in the short- or long-term) are thought to originate from this change in systemic and pulmonary blood pressure.

The long-term effects of marked single-ventricle preload and inefficient oxygenation via an arterial shunt rarely allow survival beyond the second or third decade of life. Uniformly lethal four decades ago, the newborn with single ventricle type congenital heart disease in 2010 is now not only likely—but expected—to survive. However, as these children have grown into adolescence and adulthood, it is clear that there are significant limitations to this strategy. While lifesaving, the Fontan/Kreutzer operation results in profound physiological disturbances with very serious consequences. Pervasive abnormalities of multiple organ systems are affected as time goes on. Realistically, it is unlikely that patients will survive into their third or fourth decades of life untouched by some potentially life-threatening complication. Thus, there is a clear need to identify treatments that may ameliorate the dysfunctional state of the Fontan operation. This is particularly true given the increase in the prevalence of the Fontan procedures: remarkably, the Fontan operation has become the most common procedure performed for congenital heart disease after the age of 2 years. W. M. Gersony, *Circulation*, 117: 13-15 (2008).

Multiple studies looking at the results of the Fontan operation demonstrate a decrease in survival beyond 15 years after surgery. An ongoing significant risk of death with continuous attrition is present, regardless of surgical type of cavo-pulmonary connection. In another study looking at morphologically single left ventricle after Fontan surgery, results showed that odds are 1 out 4 that a child after Fontan will be dead by the time he or she reaches their late 20s. J. Rychik, "Forty Years of the Fontan Operation: A Failed Strategy," *Pediatric Cardiac Surgery Annual*, 96-100(2010).

Given the increased life span for Fontan patients, researchers have sought out medical therapies to address the side effects of the Fontan surgery. In particular, children and young adults with single-ventricle physiology have abnormal exercise capacity after the Fontan operation. Strategies targeted toward improving cardiac output and reducing central venous pressure will improve their overall well-being and mitigate against the impact of this deleterious physiology.

In one study, the PDE5 inhibitor sildenafil was found to significantly improve ventilatory efficiency during peak and submaximal exercise. There was also a suggestion of improved oxygen consumption at the anaerobic threshold in 2 subgroups. These findings suggest that sildenafil may be an important agent for improving exercise performance in children and young adults with single-ventricle physiology after the Fontan operation. Goldberg et al., *Circulation*, 123: 1185-1193 (2011).

Later studies verified that sildenafil increased ventricular systolic elastance and improved ventriculo-arterial coupling in patients palliated with Fontan circulation. Short-term sildenafil was well tolerated in most of the patients with only minor side effects. Shabanian et al., *Pediatr. Cardiol.*, 34(1): 129-34 (2013). The structure of sildenafil is shown below:

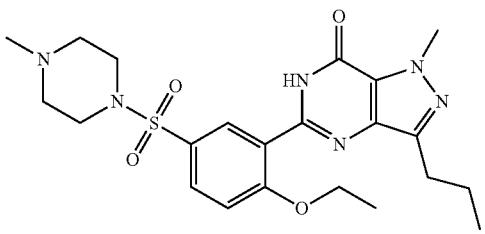 [SMILES: CCCc1nn(C)c2c(=O)[nH]c(-c3cc(S(=O)(=O)N4CCN(C)CC4)ccc3OCC)nc12]

In addition, a preliminary study assessed the short-term effects of the PDE5 inhibitor tadalafil on the hemodynamic response to exercise and exercise capacity in patients with Fontan circulation. See http://clinicaltrials.gov/ct2/show/record/NCT01291069. Short term therapy with once daily dosing of tadalafil improved ventilatory efficiency and oxygen saturation, but exercise capacity was unchanged in young Fontan subjects, similar to published sildenafil results. Menon et al., Circulation, 128: A16024 (2013). The chemical structure of tadalafil is shown below:

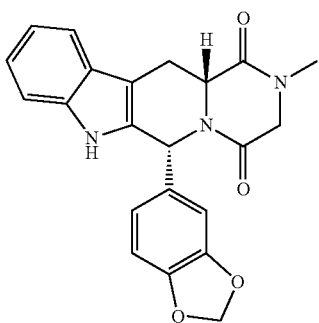 [SMILES: CN1CC(=O)N2[C@H](c3ccc4c(c3)OCO4)c3[nH]c4ccccc4c3C[C@@H]2C1=O]

For optimal effectiveness, the PDE5 inhibitors sildenafil or tadalafil would need to be given long term to Fontan patients to delay or prevent the onset of failing Fontan circulation. Fontan surgery produces chronic conditions; short term treatment is unlikely to address mortality associated with children having a Fontan surgery when they are an adolescent or adult. This is particularly true as when Fontan failure sets in, there is an inexorable hemodynamic and functional decline in the patients leading to death or cardiac transplantation. The early experience with transplantation in patients with Fontan circulation was of high operative mortality and morbidity. The assumption that if a patient survives with a Fontan circulation, then the PVR is low enough for the right ventricle of the graft after cardiac transplantation was found to be incorrect in the early experience of Fontan transplants.

While both sildenafil and tadalafil are known to have undesirable side effects, pulmonary arterial hypertension (PAH) patients switched from sildenafil to tadalafil were found to show significantly different oxygen saturation, significantly different oxygen saturation after a 6-minute walk test, and significantly different distances walked, thus showing that PDE5 inhibitors are not interchangeable when used to treat heart or cardiovascular conditions. Sabri et al., *Pediatr Cardiol.*, 35(4):699-704 (2014).

II. Background Regarding PDE5 Inhibitors and Udenafil

PDE5 is a cyclic guanosine-3',5'-monophosphate (cGMP)-specific phosphodiesterase belonging to a class of phosphodiesterases which regulate various cell functions by catalyzing the hydrolysis of the second messenger molecules cyclic (cGMP) and cyclic adenosine-3',5'-monophosphate (cAMP). Boolell et al., *Int'l J. Impot. Res.*, 8:47 (1996). Because PDE5 is present in the arterial wall smooth muscle within the lungs, PDE5 inhibitors have been explored for the treatment of pulmonary hypertension, a disease in which blood vessels in the lungs become overloaded with fluid, usually as a result of failure of the right ventricle of the heart.

Udenafil is a drug used in urology to treat erectile dysfunction. It belongs to a class of drugs called PDE5 inhibitors, which also includes sildenafil, tadalafil, and vardenafil. Typical doses are 100 and 200 mg. Udenafil is available in Korea, Russia, and Philippines; in the United States, it is not approved for use by the U.S. Food and Drug Administration.

The Fontan procedure is palliative, not curative. But in many cases it can result in normal or near-normal growth, development, exercise tolerance, and good quality of life. In 20/30% cases, patients will eventually require heart transplantation.

Modifications in the Fontan operative model was one of the early steps in improving outcome. Use of fenestration, staging of Fontan completion and better perioperative management have led to a significant drop in mortality rates in the current era. Despite this, there is late attrition of patients with complications such as arrhythmias, ventricular dysfunction, and unusual clinical syndromes of protein-losing enteropathy (PLE) and plastic bronchitis. Management of failing Fontan includes a detailed hemodynamic and imaging assessment to treat any correctable lesions such as obstruction within the Fontan circuit, early control of arrhythmia and maintenance of sinus rhythm, symptomatic treatment for PLE and plastic bronchitis, manipulation of systemic and pulmonary vascular resistance, and Fontan conversion of less favorable atriopulmonary connection to extra-cardiac total cavopulmonary connection with arrythmia surgery. Cardiac transplantation remains the only successful definitive palliation in the failing Fontan patients. However, cardiac transplantation is not a perfect solution because the Fontan circulation has already wreaked havoc in the body such as negatively affecting hepatic or kidney function, thus patients with Fontan circulation may still be in poor shape even after a heart transplant.

There is a need in the art for improved therapies relating to complications or side effects of the Fontan procedure with the goal of increasing the life span of Fontan patients, and avoiding or delaying the need for cardiac transplantation.

There is also a need in the art for improved therapies to delay the onset of cardiac failure or to improve the quality of life for patients who have had the Fontan procedure. The present invention satisfies this need.

SUMMARY OF THE INVENTION

In one embodiment, the invention is directed to methods of treating, preventing, or minimizing conditions, symptoms, or side effects associated with a subject who has previously had a Fontan procedure. In particular, the methods of the invention are directed the use of udenafil or a pharmaceutically acceptable salt thereof in single ventricle adolescent patients that have undergone the Fontan procedure for the amelioration of associated acute symptoms and chronic symptom development. The method comprises administering a therapeutically effective amount of a PDE5 inhibitor to the patient, where the PDE5 inhibitor is udenafil or a pharmaceutically acceptable salt thereof.

In one embodiment, the invention is directed to a method of improving cardiac output in a patient who has had a Fontan procedure. The method comprises administering a therapeutically effective amount of a PDE5 inhibitor to the patient, where the PDE5 inhibitor is udenafil or a pharmaceutically acceptable salt thereof.

In another embodiment, the invention is directed to a method of decreasing pulmonary vascular resistance in a patient who has had a Fontan procedure. The method comprises administering a therapeutically effective amount of a PDE5 inhibitor to the patient, where the PDE5 inhibitor is udenafil or a pharmaceutically acceptable salt thereof.

In yet another embodiment, the invention is directed to a method of improving exercise capacity in a patient who has had a Fontan procedure. The method comprises administering a therapeutically effective amount of a PDE5 inhibitor to the patient, where the PDE5 inhibitor is udenafil or a pharmaceutically acceptable salt thereof.

In one embodiment, the invention is directed to a method of improving myocardial performance in a patient who has had a Fontan procedure. The method comprises administering a therapeutically effective amount of a PDE5 inhibitor to the patient, where the PDE5 inhibitor is udenafil or a pharmaceutically acceptable salt thereof.

In an exemplary embodiment, the methods of the invention comprise administering a therapeutically effective dose of udenafil, or a pharmaceutically acceptable salt thereof, once a day to a patient.

In another embodiment, the methods of the invention comprise administering a therapeutically effective dose of udenafil, or a pharmaceutically acceptable salt thereof, twice a day to a patient.

In another embodiment, the patient is a pediatric patient of about 2 to about 18 years of age. Treatment of adult patients are also encompassed by the methods of the invention.

In yet another embodiment, the invention is directed to improved methods for treating a patient who has had a Fontan procedure, wherein the methods show an improvement in patient compliance with a dosing schedule of udenafil or a pharmaceutically acceptable salt thereof, as compared to patients prescribed a non-udenafil drug.

In one embodiment, the invention is directed to improved methods for treating a patient who has had a Fontan procedure, wherein the methods of the invention result in fewer or less severe adverse events as compared to conventional, methods of treating such patients. In another embodiment, the methods of the invention result in few, if any, serious adverse events, moderate adverse events, or mild adverse events.

In another embodiment, the methods of the invention result in improved VO2 at the patient's maximal effort as compared to VO2 at maximal effort in the absence of the methods of the invention (e.g., in the absence of udenafil administration). For example, the improvement can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to VO2 at maximal effort in the absence of the methods of the invention (e.g., in the absence of udenafil administration).

In another embodiment, the methods of the invention result in improved VO2 at the patient's anaerobic threshold as compared to VO2 at anaerobic threshold in the absence of the methods of the invention (e.g., in the absence of udenafil administration). For example, the improvement can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to VO2 at maximal effort in the absence of the methods of the invention (e.g., in the absence of udenafil administration).

In another embodiment, the methods of the invention result in the patient's blood pool MPI, or other disclosed measures of ventricular performance, improving as compared to blood pool MPI, or other disclosed measures of ventricular performance in the absence of the methods of the invention (e.g., in the absence of udenafil administration). For example, the improvement can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to blood pool MPI, or other disclosed measures of ventricular performance in the absence of the methods of the invention (e.g., in the absence of udenafil administration).

In another embodiment, the methods of the invention result in the patient's log of reactive hyperemia index, or another disclosed measure of vascular function, improving as compared to log of reactive hyperemia index, or another disclosed measure of vascular function, in the absence of the methods of the invention (e.g., in the absence of udenafil administration). For example, the improvement can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30% or greater as compared to log of reactive hyperemia index, or another disclosed measure of vascular function, in the absence of the methods of the invention (e.g., in the absence of udenafil administration).

Finally, in yet another embodiment, the methods of the invention may result in a characteristic pharmacokinetic profile. The pharmacokinetic profile can comprises a $C_{max}$ between 300 and 700 ng/ml, or more specifically, about 500 ng/ml; a $T_{max}$ between 1 and 1.6 hr, or more specifically, about 1.3 hr; an AUCτ between 2550 and 4150 ng·hr/ml, or more specifically, about 3350 ng·hr/ml; and an $AUC_{0-24}$ between 5110 and 8290 ng·hr/ml, or more specifically, about 6701 ng·hr/ml.

The foregoing general description and following detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 28 shows a summary of average plasma concentration per time point from pharmacokinetic studies of udenafil in Fontan's patients. Data are shown as mean+/−standard deviation.

FIG. 29 shows non-compartmental analysis of udenafil in Fonatn's patients stratified by dosing regimens. Data are shown as mean+/−standard deviation.

DETAILED DESCRIPTION OF THE PREFERRED EMBODIMENTS

I. Fontan Physiology

Figure 34:
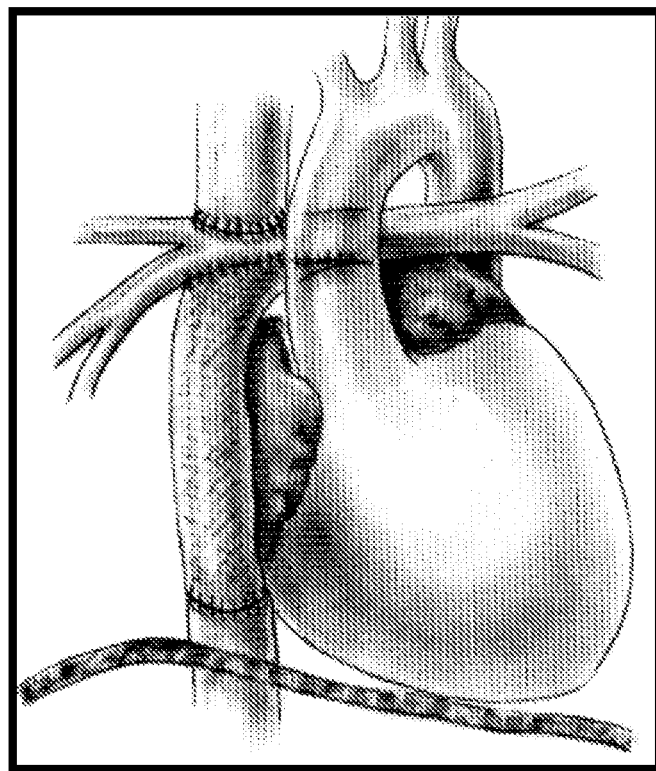
FIG. 34 shows characteristic Fontan physiology.

The Fontan physiology is the definitive palliation for those classes of congenital heart defects that share the common feature of a functional single ventricle. They include defects that result in hypoplastic left or right ventricles. Usually through a series of 2 or 3 operations, the systemic and pulmonary circulations are separated to eliminate the mixing of oxygenated and un-oxygenated blood. This is accomplished by directly attaching the superior and inferior vena cavae to the pulmonary arteries. This results in a physiology that works as follows: (1) the single systemic ventricle pumps oxygenated blood out the aorta to the body's systemic vascular bed. (2) Next, the systemic venous blood then returns by the vena cavae and flows passively through the pulmonary vascular bed without the aid of a sub-pulmonary ventricle. (3) Finally, oxygenated blood returns to the common systemic atrium and the cycle is repeated. This anatomy is illustrated in FIG. 34.

The Fontan operation, which creates a total cavopulmonary connection, separates the systemic and pulmonary circuits and eliminates both hypoxemia and ventricular volume overload. However, following the Fontan operation there is no ventricular pump to propel blood into the pulmonary arteries. Instead blood returns to the lungs via passive flow from the systemic veins. Thus, the major physiologic consequence of this type of palliation is that pulmonary blood flow is completely dependent upon the pressure gradient from the systemic venous bed to the atrium. The normal circulation flow through the pulmonary bed is augmented by the increased pressure generated by the right ventricle. In a healthy adolescent, this results in an increase of about 20 to 25 mm Hg in the pressure present in the pulmonary arteries at rest, which may double with exercise. With the Fontan physiology, there is no sub-pulmonary ventricle and thus no augmentation of pressure as the blood enters the pulmonary arteries. At rest, the pressure gradient across the pulmonary vascular bed is significantly less. The ability to increase this pressure gradient with exercise is extremely limited by the body's ability to tolerate increasingly elevated central venous pressures.

As a unique consequence of being entirely dependent upon the passive drop in venous pressure to drive pulmonary blood flow, the Fontan physiology is exquisitely sensitive to changes in pulmonary vascular resistance. Even increases that are well within the normal range for pulmonary resistance in normal physiology will have detrimental effects on the Fontan physiology. Likewise any decrease in resistance, even if this value is already normal, has the potential to augment pulmonary blood flow. For this reason, the use of udenafil offers a potential therapy that is unique to this class of palliated congenital heart defects. Unlike other uses for PDE-5 inhibitors, this therapy would be to lower resistance in a population without elevated pulmonary resistances or pressures. This is a distinctly different use of this class of agents as compared to patients with either structurally normal hearts and pulmonary vascular disease or the very rare patient with congenital heart disease palliated with a two ventricle repair (and thus having a sub-pulmonary ventricle) and associated pulmonary vascular disease.

II. Clinical Measurements Relevant to Fontan Patients

For children born with functional single ventricle congenital heart disease, the Fontan procedure is the current standard of care. The Fontan procedure is palliative, rather than curative, and while it has greatly increased the survival of pediatric subjects with functional single ventricle congenital heart disease, the procedure also results in a series of side effects and complications that can lead to late attrition of patients, with complications such as arrhythmias, ventricular dysfunction, and unusual clinical syndromes of protein-losing enteropathy (PLE) and plastic bronchitis, as well as hepatic and kidney complications.

In certain embodiments, the disclosed invention relates to improving or preventing the decline of specific clinically relevant measurements that are indicative of a patient's health following a Fontan procedure. Such measurements include, but are not limited to, exercise testing, vascular function testing, and echocardiographic assessment of ventricular performance.

Exercise Testing

Exercise testing can include assessment of VO2 values during maximal effort or at anaerobic threshold. VO2 max, or maximal oxygen consumption, refers to the maximum amount of oxygen that an individual can utilize during intense exercise. This measurement is generally considered a reliable indicator of cardiovascular fitness and aerobic endurance. Theoretically, the more oxygen a person can use during high level exercise, the more energy that person can produce. This test is the gold standard for cardiorespiratory fitness because muscles need oxygen for prolonged (aerobic) exercise; blood carries oxygen to the muscles and the heart must pump adequate amounts of blood to meet the demands of aerobic exercise.

VO2 is often measured by putting a mask on a subject, and measuring the volume and gas concentrations of inhaled and expired air. This measurement is often used in both clinical settings and research and is considered the most accurate. Testing commonly involves either exercising on a treadmill or riding a bike at increasing intensity until exhaustion, and is designed to provide readings at a maximal effort of the subject and/or at the subject's anaerobic threshold.

Patients that have previously undergone a Fontan procedure will generally see a decline in VO2 measurements over time. Treating a patient with a method according to the invention such that the patient's VO2 measurement are either maintained at a similar level, demonstrating that there has been no further decline in VO2 function, or improve with therapy indicates that the treatment is clinically beneficial and may improve or prevent decline in cardiovascular function.

In one embodiment, the invention is directed to a method of improving or maintaining VO2 measurements of a subject who has previously had a Fontan procedure. The method comprises administering a therapeutically effective amount of a PDE5 inhibitor to the patient, where the PDE5 inhibitor is udenafil or a pharmaceutically acceptable salt thereof. In some embodiments, VO2 is measured at maximal effort, while in other embodiments, VO2 is measured at the subject's anaerobic threshold.

In some embodiments, the disclosed methods and compositions are administered to a Fontan patient and result in no decrease, or a minimal decrease, in exercise capacity over time. More specifically, the disclosed methods and compositions may result in a decrease in exercise capacity of less than about 40, less than about 35, less than about 30, less than about 35, less than about 20, less than about 15, less than about 10, or less than about 5% over time. The time period between a first and second measurement used to calculate the decrease in exercise capacity can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions may be administered to a Fontan patient and result in an improvement of exercise capacity. More specifically, the disclosed methods and compositions may result in a 1, 2, 5, 10, 15, 20, 25, 30, 35, 40, 45, or 50% or more improvement in VO2 at maximal effort. Alternatively, the disclosed methods and compositions may result in a 1, 2, 5, 10, 15, 20, 25, 30, 35, 40, 45, or 50% or more improvement in VO2 at the patient's anaerobic threshold.

Vascular Function Testing

Vascular endothelial dysfunction is an important outcome for assessing vascular health in intervention studies. It is now well established that vascular endothelial dysfunction is positively associated with traditional cardiovascular disease (CVD) risk factors, and independently predicts cardiovascular events over intervals of 1 to 6 years.

Pulse amplitude tonometry (PAT), a FDA-approved method for assessing vascular function, is increasingly being used as an alternative measure of endothelium-dependent dilation in response to reactive hyperemia and flow-mediated dilation (FMD). The PAT device records digital pulse wave amplitude (PWA) using fingertip plethysmography. PWA can be measured continuously during three phases: a quiet baseline period, 5-min forearm occlusion, and reactive hyperemia following cuff release. Unlike FMD, PAT testing is not dependent upon a highly skilled technician and post-test analysis is largely automated. Most importantly, at least one longitudinal study has shown that PAT measures of endothelial function predict CVD events over a 6-year follow-up period. These significant advantages may make PAT testing suitable for clinical practice if prognostic significance and reliability can be verified.

Patients that have previously undergone a Fontan procedure will generally see a decline in vascular function over time. Treating a patient such that the patient's vascular function increases or preventing further decline in vascular function would indicate that the treatment is clinically beneficial and may improve patient quality of life or prevent decline in cardiovascular function.

In one embodiment, the invention is directed to a method of improving or maintaining vascular function of a subject who has previously had a Fontan procedure. The method comprises administering a therapeutically effective amount of a PDE5 inhibitor to the patient, where the PDE5 inhibitor is udenafil or a pharmaceutically acceptable salt thereof. In some embodiments, vascular function is measured using a PAT index.

In some embodiments, the disclosed methods and compositions are administered to a Fontan patient and result in no decrease, or a minimal decrease, in vascular function over time. Vascular function can be measured using any conventional known technique, including but not limited to pulse amplitude tonometry measurements, the natural log of reactive hyperemia index, Reactive Hyperemia Index, Framingham RHI, area under the curve to max-occlusion/control, average up to max-occlusion/control, and other known EndoPAT indices. In some embodiments, vascular function is measured using a PAT index. More specifically, the disclosed methods and compositions may result in a decrease in vascular function of less than about 40, less than about 35, less than about 30, less than about 35, less than about 20, less than about 15, less than about 10, or less than about 5% over time. The time period between a first and second measurement used to calculate the decrease in vascular function can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions may be administered to a Fontan patient and result in an improvement of vascular function. Vascular function can be measured using any conventional known technique, including but not limited to pulse amplitude tonometry measurements, the natural log of reactive hyperemia index, Reactive Hyperemia Index, Framingham RHI, area under the curve to max-occlusion/control, average up to max-occlusion/control, and other known EndoPAT indices. In some embodiments, vascular function is measured using a PAT index. More specifically, the disclosed methods and compositions may result in about a 1, about 2, about 5, about 10, about 15, about 20, about 25, about 30, about 35, about 40, about 45, or about 50% or more improvement in one or more measurements of vascular function, including but not limited to pulse amplitude tonometry measurement, the natural log of reactive hyperemia index, Reactive Hyperemia Index, Framingham RHI, area under the curve to max-occlusion/control, average up to max-occlusion/control, and other known EndoPAT indices.

Echocardiographic Assessment of Ventricular Performance

Ventricular performance and cardiac contractility are important measurements that can reveal impairment of cardiovascular health before overt heart failure is present. Ventricular performance can be assessed using echocardiographic methods and quantified via a myocardial performance index or MPI. MPI is an index that combines systolic and diastolic function. Specifically, MPI is defined as the sum of isovolumic contraction time and isovolumic relaxation time divided by the ejection time.

Various versions of MPI are known in the art, and each version of MPI may be used to assess ventricular performance. For instance, MPI indices may include but are not limited to blood pool MPI, tissue doppler MPI, average isovolumetric contraction, and average isovolumetric relaxation.

Patients that have previously undergone a Fontan procedure will generally see a decline in ventricular performance over time. Treating a patient such that the patient's ventricular performance is maintained, exhibits minimal decrease over time, or increases indicates that the treatment is clinically beneficial and may improve patient quality of life or prevent decline in cardiovascular function.

In one embodiment, the invention is directed to a method of maintaining, producing a minimal decrease in, or increasing ventricular performance of a subject who has previously had a Fontan procedure. The method comprises administering a therapeutically effective amount of a PDE5 inhibitor to the patient, where the PDE5 inhibitor is udenafil or a pharmaceutically acceptable salt thereof. In some embodiments, ventricular performance is measured using a myocardial performance index (MPI). In some embodiments, the MPI may be a blood pool MPI, while in otherembodiments the MPI may be a tissue doppler MPI.

In some embodiments, the disclosed methods and compositions may be administered to a Fontan patient and result in minimal or no decrease in ventricular performance over time. Ventricular performance can be measured using any conventional known technique, including but not limited to myocardial performance index (MPI), blood pool MPI, tissue doppler MPI, average isovolumetric contraction and relaxation, and other known ventricular performance indices. More specifically, the disclosed methods and compositions may result in a decrease in ventricular performance of less than about 40, less than about 35, less than about 30, less than about 35, less than about 20, less than about 15, less than about 10, or less than about 5% over time. The time period between a first and second measurement used to calculate the decrease in ventricular performance can be, for example, about 1, about 2, about 3, about 4, about 5, about 6, about 7, about 8, about 9, about 10, about 11, or about 12 months; about 1, about 2, about 3, about 4, about 5, about 6, about 7, about 8, about 9, about 10, about 11, about 12, about 13, about 14, or about 15 years, or any combination thereof, e.g., 1 year, 3 months; 4 years, 7 months, etc.

In some embodiments, the disclosed methods and compositions may be administered to a Fontan patient and result in an improvement of ventricular performance over time. Ventricular performance can be measured using any conventional known technique, including but not limited to myocardial performance index (MPI), blood pool MPI, tissue doppler MPI, average isovolumetric contraction and relaxation, and other known ventricular performance indices. For example, the disclosed methods and compositions may result in about a 1, about 2, about 5, about 10, about 15, about 20, about 25, about 30, about 35, about 40, about 45, or about 50% or more improvement in ventricular performance, as measured by any known technique, including but not limited to myocardial performance index (MPI), blood pool MPI, tissue doppler MPI, average isovolumetric contraction and relaxation, and other known ventricular performance indices.

III. Methods According to the Invention

In one embodiment, the invention is directed to methods of treating, preventing, or minimizing conditions, symptoms, or side effects associated with a subject who has previously had a Fontan procedure. The method comprises administering a therapeutically effective amount of a PDE5 inhibitor to the patient, where the PDE5 inhibitor is udenafil or a pharmaceutically acceptable salt thereof.

In the Fontan circulation, pulmonary blood flow is passive, driven by the pressure difference between the systemic venous circulation and the ventricular end-diastolic pressure. A medication capable of allowing for more efficient transit of blood through the pulmonary vascular bed can allow for improvement in cardiac preload, and therefore improve cardiac output.

PDE5 inhibitors are a class of medications that reduce pulmonary vascular resistance and improve ventricular performance in patients with pulmonary hypertension and myocardial dysfunction.

Some studies have evaluated the single-use or longer-term use of sildenafil in children and young adults who have had the Fontan procedure. However, sildenafil has a short half-life, and is typically administered three to four times per day. Such an administration schedule is not convenient and is likely to reduce patient compliance. In addition, the administration of a short half-life drug results in greater fluctuations of therapeutic levels of drug, increasing the risk that the blood level of the PDE5 inhibitor will drop below the therapeutically effective level for parts of the day. The present inventors hypothesize that administration of a PDE5 inhibitor having a longer half-life to patients who have had the Fontan procedure will prevent or ameliorate the decline in aerobic exercise performance in patients following the Fontan procedure.

Patient compliance is critical for optimal therapeutic efficacy, particularly for a drug that is to be taken daily for an extended period of time, such as for several years or more. This is particularly true for Fontan patients. In particular, individuals that had the Fontan procedure most often die from heart failure, stroke (thrombosis), or some unexplained sudden death. Of note is the fact that the risk of death from heart failure is quite low within 10 years of the Fontan procedure but increases with time after 10 years post-Fontan. http://bendantzer.wordpress.com/2013/03/13/fontan-circulation-success-or-failure/.

Not surprisingly, as time passes from the date of the Fontan procedure, the risk of death or need from a heart transplant increases. This could be from some sudden death or heart failure, but it could also be from a gradual decline in heart function. As the years tick by after the Fontan procedure, heart function gets worse, which is reflected in the decline in the ability to do aerobic exercise. For example, for patients that had the Fontan early in life, they may have exercise capacity that is highly reduced (44%) compared to normal patients and this capacity to do exercise tends to decline in a linear fashion each year (declines 2.6% each year). At thirty years of age, patients with Fontan circulation have much reduced exercise capacity (55% less than normal) and the number of health problems and hospitalization rates increase dramatically. This is probably not surprising since, again, one ventricle is doing the work of two. Thus, methods according to the invention which can diminish or significantly decrease decline in heart function over time, are highly desirable for Fontan patients. Key to the success of such methods is patient compliance with a preferred dosing schedule.

Patient compliance, or lack thereof, to a prescribed dosing schedule is known to be a critical factor in the success of any therapy. In particular, quality healthcare outcomes depend upon patients' adherence to recommended treatment regimens. Patient nonadherence can be a pervasive threat to health and wellbeing and carry an appreciable economic burden as well. In some disease conditions, more than 40% of patients sustain significant risks by misunderstanding, forgetting, or ignoring healthcare advice. Moreover, when preventive or treatment regimens are very complex and/or require lifestyle changes and the modification of existing habits, nonadherence can be as high as 70%. Martin et al., *Ther. Clin. Risk Manag.*, 1(3): 189-199 (2005) ("A significant barrier to effective medical treatment, however, is the patient's failure to follow the recommendations of his or her physician or other healthcare provider."). Thus, a therapy that can produce the desired results (e.g., improved cardiac output, decreased pulmonary vascular resistance, improved exercise capacity, improved myocardial performance, preventing or ameliorating the decline in aerobic exercise performance), with a preferred once or twice a day dosage, as compared to multiple daily dosages—e.g., 3 to 6× daily—required to be taken at least 4 to 6 hours apart, such as with sildenafil, is highly desirable. Such a more simplistic dosing regimen is likely to lead to a significant increase in patient compliance, and concomitant improved therapeutic results.

In one embodiment, the invention is directed to a method of improving cardiac output in a patient who has had the Fontan procedure, the method comprising administering a therapeutically effective amount of the PDE5 inhibitor udenafil, or a pharmaceutically acceptable salt thereof, to the patient. For example, the method of the invention can result in an improvement in cardiac output, as compared to a subject who is not administered udenafil, of about 5%, about 8%, about 10%, about 15%, about 20%, about 25%, about 30%, about 35%, about 40%, about 45%, or about 50%.

In another embodiment, the invention is directed to a method of decreasing pulmonary vascular resistance in a patient who has had the Fontan procedure, the method comprising administering a therapeutically effective amount of the PDE5 inhibitor udenafil, or a pharmaceutically acceptable salt thereof, to the patient. For example, the method of the invention can result in an decreased pulmonary vascular resistance, as compared to a subject who is not administered udenafil, of about 5%, about 8%, about 10%, about 15%, about 20%, about 25%, about 30%, about 35%, about 40%, about 45%, or about 50%.

In yet another embodiment, the invention is directed to a method of improving exercise capacity in a patient who has had the Fontan procedure, the method comprising administering a therapeutically effective amount of the PDE5 inhibitor udenafil, or a pharmaceutically acceptable salt thereof, to the patient. For example, the method of the invention can result in an increase in exercise capacity measured by maximal VO2, as compared to a subject who is not administered udenafil, of about 5%, about 8%, about 10%, about 15%, about 20%, about 25%, about 30%, about 35%, about 40%, about 45%, or about 50%.

In one embodiment, the invention is directed to a method of improving myocardial performance in a patient who has had the Fontan procedure, the method comprising administering a therapeutically effective amount of a PDE5 inhibitor to the patient. For example, the method of the invention can result in an improvement in myocardial performance, as compared to a subject who is not administered udenafil, of about 5%, about 8%, about 10%, about 15%, about 20%, about 25%, about 30%, about 35%, about 40%, about 45%, or about 50%.

In one embodiment, the invention is directed to a method of preventing or ameliorating the decline in aerobic exercise performance in a patient who has had the Fontan procedure, the method comprising administering a therapeutically effective amount of the PDE5 inhibitor udenafil, or a pharmaceutically acceptable salt thereof, to the patient. For example, the method of the invention can result in an amelioration of the decline in aerobic exercise performance measured by maximal VO2, as compared to a subject who is not administered udenafil, of about 5%, about 8%, about 10%, about 15%, about 20%, about 25%, about 30%, about 35%, about 40%, about 45%, or about 50%.

In yet another embodiment, the invention is directed to improved methods for treating a patient who has had a Fontan procedure, wherein the methods show an improvement in patient compliance with a dosing schedule of udenafil or a pharmaceutically acceptable salt thereof, as compared to patients prescribed a non-udenafil drug.

Udenafil has a half-life of 7.3-12.1 hours, and is believed to possibly have a much better safety profile as compared to sildenafil or tadalafil. Udenafil has unique properties, with a $T_{max}$ of 1.0-1.5 h and a $T_{1/2}$ of 11-13 h (a relatively rapid onset and a long duration of action). Therefore, both on-demand and once-daily use of udenafil have been reported. Udenafil's efficacy and tolerability have been evaluated in several studies, and recent and continuing studies have demonstrated udenafil's promise in both dosing regimens. Presently, tadalafil is the only FDA-approved drug for daily dosing, but udenafil can be used as a once-daily dose for erectile dysfunction patients who cannot tolerate tadalafil due to phosphodiesterase subtype selectivity. Gu Kang et al., *Ther. Adv. Urol.*, 5(2): 101-110 (2013). Once-daily dosing of udenafil was evaluated for the treatment of erectile dysfunction (ED), and the results showed that udenafil significantly improved erectile function among ED patients when administered in doses of 50 mg or 75 mg once daily for 12 wk. Zhao et al., *Eur. J. of Urology*, 60: 380-387 (2011). While these reports suggest that udenafil may be useful as a once a day therapy for various conditions, other reports show that PDE5 inhibitors show varying efficacy in treating symptoms associated with the Fontan operation. Sabri et al., *Pediatr. Cardiol.*, 35(4):699-704 (2014).

Thus, it was surprising that the present invention, directed to methods of treating, minimizing, and/or preventing symptoms associated with the Fontan operation comprising administering udenafil or a pharmaceutically acceptable salt thereof, shows desirable results, preferably with a once or twice a day dosage. "Desirable results" include, but are not limited to, improved cardiac output, decreased pulmonary vascular resistance, improved exercise capacity, improved myocardial performance, preventing or ameliorating the decline in aerobic exercise performance, and/or an improvement in patient compliance.

In one embodiment of the invention, once a day administration of a therapeutically effective dosage of uldenafil, or a pharmaceutically acceptable salt thereof, results in therapeutic levels of uldenafil, present in the patient's blood stream, for up to about 8 hours. In other embodiments of the invention, once a day administration of a therapeutically effective dosage of uldenafil, or a pharmaceutically acceptable salt thereof, results in therapeutic levels of uldenafil, present in the patient's blood stream, for up to about 10, about 11, about 12, about 13, about 14, about 15, about 16, about 17, about 18, about 19, about 20, about 21, about 22, about 23, or about 24 hours.

In one embodiment of the invention, twice a day administration of a therapeutically effective dosage of udenafil, or a pharmaceutically acceptable salt thereof, results in therapeutic levels of udenafil for at least about 16 hours in a 24 hour dosing period. In other embodiments, twice a day administration of a therapeutically effective dosage of udenafil, or a pharmaceutically acceptable salt thereof, results in therapeutic levels of udenafil for at least about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours, in a 24 hour dosing period.

In another embodiment, it was surprising that that the methods of the invention show improved results as compared to prior art treatments using a non-udenafil PDE5 inhibitor, such as sildenafil or tadalafil. In yet another embodiment, it was surprising that the methods of the invention show fewer side effects, and/or less severe side effects, as compared to prior art treatments using a non-udenafil PDE5 inhibitor, such as sildenafil or tadalafil.

In one embodiment, it is surprising that the administration of twice a day udenafil or a pharmaceutically acceptable salt thereof results in fewer side effects than the administration of once a day udenafil or a pharmaceutically acceptable salt thereof. In another embodiment, it is surprising that twice a day administration of udenafil or a pharmaceutically acceptable salt thereof can achieve therapeutically effective levels of udenafil at a lower total daily dosage than a once a day administration.

In one embodiment, the patient who has had the Fontan procedure is a human patient. In one embodiment, the patient is an adult human patient over about 18 years of age. In another embodiment, the patient is a pediatric patient of about 2 to about 18 years of age. In another embodiment, the patient is a pediatric patient of about 12 to about 18 years of age, or from about 12 to about 16 years of age.

IV. Pediatric Patients

Treatment of pediatric patients presents particular challenges, as pediatric physiology is not just a miniature version of an adult. Physical size is just one of the many differences. Children's body surface area, organ and system maturity and function, as well as cognitive and emotional development can result in differences in response to illness, diagnosis, treatment, and medications. Even illnesses that are seen in adults can act differently in children because of their unique anatomy and physiology. Moreover, pediatric patients process drugs differently than adults, and therefore the effects as well as the dosages of drugs may vary widely from those observed with adults. Since children differ from adults in many ways beyond size, simply adjusting the dose of a drug for a smaller size person will not necessarily produce the same response and can lead to adverse drug reactions. Thus, the effectiveness of a drug used in treating an adult condition does not with certainty predict success of treating a pediatric patient with the same drug.

Thus, the invention is also directed to the surprising discovery that pediatric Fontan patients can be successfully treated with the methods of the invention. The methods comprise administering a therapeutically effective amount of a PDE5 inhibitor to the pediatric patient, where the PDE5 inhibitor is udenafil or a pharmaceutically acceptable salt thereof.

The structure of udenafil is shown below:

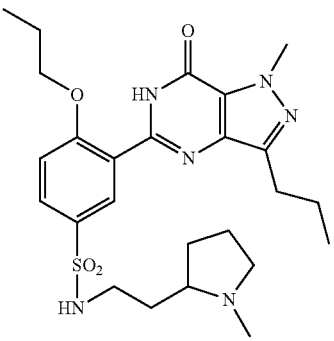 [SMILES: CCCOc1ccc(S(=O)(=O)NCCC2CCCN2C)cc1-c1nc2c(CCC)nn(C)c2c(=O)[nH]1]

V. Doses and Dosage Forms

In one embodiment, the udenafil or a pharmaceutically acceptable salt thereof is administered at total daily dosage amounts of about 0.01 to about 150 mg/kg. In another embodiment, the udenafil or a pharmaceutically acceptable salt thereof is administered at total daily doses of about 0.01 mg/kg up to about 30 mg/kg. In another embodiment, the udenafil or a pharmaceutically acceptable salt thereof is administered at total daily doses of about 5 mg, about 10 mg, about 15 mg, about 20 mg, about 25 mg, about 27.5 mg, about 30 mg, about 32.5, about 35 mg, about 37.5 mg, about 40 mg, about 42.5 mg, about 45 mg, about 47.5 mg, about 50 mg, about 55 mg, about 60 mg, about 65 mg, about 70 mg, about 75 mg, about 80 mg, about 85 mg, about 87.5 mg, about 90 mg, about 95 mg, about 100 mg, about 125 mg, about 150 mg, about 175 mg, about 200 mg, about 225 mg, about 250 mg, or about 275 mg. In one embodiment, the udenafil or a pharmaceutically acceptable salt thereof is administered in total daily doses of about 25 mg, about 37.5 mg, about 50 mg, about 75 mg, about 87.5 mg, 125 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, or about 700 mg. In another particular embodiment, udenafil or a pharmaceutically acceptable salt thereof is administered at a total daily dose of about 37.5 mg, about 75 mg, about 87.5 mg, 125 mg, or about 175 mg.

In one embodiment, the udenafil or a pharmaceutically acceptable salt thereof is administered once a day.

In another embodiment, the udenafil or a pharmaceutically acceptable salt thereof is administered twice a day. In one embodiment, the udenafil or a pharmaceutically acceptable salt thereof is administered twice a day such that therapeutically effective blood levels are maintained for at least about 18, about 19, about 20, about 21, about 22, about 23 or about 24 hours of a 24 hour dosing period. In some embodiments, the total daily dosage amount of udenafil or a pharmaceutically acceptable salt administered twice a day is less than the total daily dosage amount of udenafil or a pharmaceutically acceptable salt thereof administered once a day. In some embodiments, the total daily dosage amount of udenafil or a pharmaceutically acceptable salt thereof administered twice a day, maintains therapeutically effective blood levels for the same number of hours in a 24 hour period as a higher dosage of udenafil or a pharmaceutically acceptable salt thereof when administered once a day. In other embodiments, the total daily dosage amount of udenafil or a pharmaceutically acceptable salt thereof administered twice a day, maintains therapeutically effective blood levels for a higher number of hours in a 24 hour period as the same dosage of udenafil or a pharmaceutically acceptable salt thereof when administered once a day.

In some embodiments, the udenafil or a pharmaceutically acceptable salt thereof administered twice a day produces a greater reduction in the conditions, symptoms, or side effects associated with a subject who has previously had a Fontan procedure, when compared to udenafil or a pharmaceutically acceptable salt thereof administered once a day.

In some embodiments, the pharmaceutically acceptable salt of udenafil is an acid addition salt. In one embodiment, the acid addition salt of udenafil is an inorganic acid addition salt such as, hydrochloric, hydrobromic, sulfuric, or phosphoric acid addition salt. In another embodiment, the acid addition salt is an organic acid addition salt such as citrate, tartarate, acetate, lactate, maleate, fumarate, gluconate, methanesulfonate (mesylate), glycolate, succinate, p-toluenesulfonate (tosylate), galacturonate, embonate, glutamate, aspartate, oxalate, benzensulfonate, camphorsulfonate, cinnamate, adipate, or cyclamate. In a particular embodiment, the pharmaceutically acceptable salt of udenafil is an oxalate, benzensulfonate, camphorsulfonate, cinnamate, adipate, or cyclamate salt.

In one embodiment the udenafil or a pharmaceutically acceptable salt thereof is administered as a pharmaceutical composition. In one embodiment, the pharmaceutical composition comprising udenafil or a pharmaceutically acceptable salt thereof can be formulated in a wide variety of oral or parenteral dosage forms on clinical application. Each of the dosage forms can contain various disintegrating agents, surfactants, fillers, thickeners, binders, diluents such as wetting agents or other pharmaceutically acceptable excipients.

The udenafil composition can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

Further, the udenafil composition can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising udenafil or a pharmaceutically acceptable salt thereof can be formulated in a solid dosage form for oral administration, and the solid dosage form can be powders, granules, capsules, tablets or pills. In yet another embodiment, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising udenafil or a pharmaceutically acceptable salt thereof can be formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising udenafil or a pharmaceutically acceptable salt thereof can be formulated as a nasal dosage form. Such dosage forms of the present invention comprise solution, suspension, and gel compositions for nasal delivery.

In one embodiment, the pharmaceutical composition can be formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising udenafil or a pharmaceutically acceptable salt thereof can be formulated to be suitable for administration to a pediatric patient.

In one embodiment, the pharmaceutical composition can be formulated in a dosage form for parenteral administration, such as sterile aqueous solutions, suspensions, emulsions, non-aqueous solutions or suppositories. In other embodiments, the non-aqueous solutions or suspensions can include propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

VI. Adverse Events

Adverse events are an important consideration, particularly when treating a susceptible population such as pediatric patients with Fontan physiology. PDE-5 inhibitors may produce adverse events including eye and/or hearing issues. Therefore, developing methods in which PDE-5 inhibitors such as udenafil or a pharmaceutically acceptable salt thereof can safely be administered to pediatric patients is one aspect of the invention.

In some embodiments, a pediatric patient with Fontan physiology may be administered a PDE-5 inhibitor to treat, minimize, and/or prevent the deleterious effects of Fontan physiology. In some embodiments, administering the PDE-5 inhibitor, specifically udenafil or a pharmaceutically acceptable salt thereof, results in minimal if any serious adverse events. In other embodiments, administering the PDE-5 inhibitor, specifically udenafil or a pharmaceutically acceptable salt thereof, results in minimal if any unexpected adverse events.

In some embodiments, a pediatric patient with Fontan physiology being administered udenafil or a pharmaceutically acceptable salt thereof may experience only mild adverse events related to the medication, and in other embodiments, the patient may experience only moderate adverse events related to the medication. In some embodiments, a pediatric patient with Fontan physiology being administered udenafil or a pharmaceutically acceptable salt thereof may experience fewer, less frequent, or less severe adverse events compared to a Fontan patient receiving another PDE-5 inhibitor.

VII. Pharmacokinetic Parameters

Pharmacokinetics refers to the absorption, distribution, metabolism, and excretion of a drug once it has been administered to a subject. The kinetics of a drug have an impact on the drug's efficacy and toxicity. A given drug's kinetic profile can depend not only on the compound itself, but also on the size of the dose and the dosing regimen as well as how the drug is formulated and administered. Pharmacokinetic parameters that may be useful in determining clinical utility include but are not limited to plasma concentration, plasma concentration over time, maximum plasma concentration ($C_{max}$), time to reach maximum concentration ($T_{max}$), area under concentration time curve within the dosing interval (AUCτ), daily area under concentration time curve at steady state ($AUC_{0-24}$); CL/F, apparent clearance; V/F, apparent volume of distribution; ke, elimination rate constant; T½, terminal half-life.

In some embodiments, the disclosed invention is directed to methods of administering udenafil or a pharmaceutically acceptable salt thereof to a patient with Fontan physiology, wherein the administration results in a unique pharmacokinetic profile. For instance, in some embodiments the disclosed methods can produce plasma concentrations of udenafil ranging from about 10 to about 700 ng/ml, about 50 to about 650 ng/ml, about 100 to about 600 ng/ml, about 150 to about 550 ng/ml, or about 200 to about 500 ng/ml. In other words, dosing regimens of the disclosed methods may result in sustained plasma concentrations of udenafil above 25, 50, 75, 100, 125, 150, 175, 200, 225, 250, 275, 300, 325, 350, 375, 400, 425, 450, 475, 500, 525, 550, 575, 600, 625, 650, 675, or 700 ng/ml. In some embodiments, the plasma concentration is maintained above about 140 ng/ml.

In some embodiments, the disclosed methods include a characteristic pharmacokinetic profile in which the $C_{max}$ is about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, or about 700 ng/ml. In some embodiments, the $C_{max}$ is about 506.

In some embodiments, the disclosed methods include a characteristic pharmacokinetic profile in which the $T_{max}$ is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 hours (hr). In some embodiments, the $T_{max}$ is about 1.3 hr.

In some embodiments, the disclosed methods include a characteristic pharmacokinetic profile in which the area under the curve (AUC) is unique to a therapeutically effective dose of udenafil in a Fontan's patient. For instance AUCτ is between 750 and 4500 ng·hr/ml, 800-4000 ng·hr/ml, or 850-3500 ng·hr/ml. More specifically AUCτ is about 750, about 800, about 850, about 900, about 950, about 1000, about 1050, about 1100, about 1150, about 1200, about 1250, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, or about 4500 ng·hr/ml. In some embodiments, the AUCτ is about 3350.

In some embodiments, $AUC_{0-24}$ is between 750 and 8500 ng·hr/ml, 800-8000 ng·hr/ml, or 850-7500 ng·hr/ml. More specifically $AUC_{0-24}$ is about 750, about 800, about 850, about 900, about 950, about 1000, about 1050, about 1100, about 1150, about 1200, about 1250, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, or about 8500 ng·hr/ml. In some embodiments, the $AUC_{0-24}$ is about 6700.

In some embodiments, the pharmacodynamics results of administering udenafil to a patient with Fontan's physiology can be attributed to the characteristic pharmacokinetic profile of the drug administration or regimen.

VIII. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The terms "administration of or "administering" an active agent should be understood to mean providing an active agent of the invention to the subject in need of treatment in a form that can be introduced into that individual's body in a therapeutically useful form and therapeutically effective amount.

The term "therapeutically effective amount" refers to a sufficient quantity of the active agents of the present invention, in a suitable composition, and in a suitable dosage form to treat or prevent the symptoms, progression, or onset of the complications seen in patients who have had the Fontan procedure. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

The terms "individual," "host," "subject," and "patient" are used interchangeably herein.

As used herein, "improving cardiac output" means an increase in the volume of blood pumped by the heart. The cardiac output is commonly measured as a function of the oxygen consumption.

As used herein, the term "exercise capacity" refers to the maximum amount of physical exertion that a patient can sustain. Exercise capacity can be measured by a number of different clinical methods, including by interview or by direct measurement. The present methods include different methods of measuring exercise capacity, including but not limited to, riding a cycle ergometer or walking on a treadmill. Thus, the term "improving exercise capacity" means increasing the ability of the patient to perform any level of physical exertion or exercise.

As used herein, the term "decreasing pulmonary vascular resistance" refers to decreasing or reducing the resistance offered by lung vasculature to blood flow.

As used herein, "improving myocardial performance" refers to an increase or decrease, as the case can be, in specific heart function measurements, including but not limited to, specific electrocardiographic readings, echocardiographic readings, cardiac output measures, heart rate, systolic or diastolic pressure, forced vital capacity, oxygen saturation, and respiratory rate.

As used herein, "aerobic exercise performance" refers to the ability of a patient to perform a specified aerobic exercise.

As used herein, "pediatric" refers to a population of subjects ranging between a newborn and about 18 years of age. A pediatric subject can include a subject that begins a course of treatment with the disclosed compositions or according to the disclosed methods prior to turning about 18 years of age, even if the subject continues treatment beyond 18 years of age. More specifically, within the population of "pediatric" subjects, neonates may be defined as 1 week to 1 month in age, infants may be 1 to less than 2 years of age, toddlers may be 2 to less than 6 years of age, and school age may refer to subjects 6-18 years of age.

The following examples are given to illustrate the present invention. It should be understood, however, that the invention is not to be limited to the specific conditions or details described in these examples. All printed publications referenced herein are specifically incorporated by reference.

EXAMPLES

Example 1

Phase I/II Pharmacokinetic and Pharmacodynamic Study

A Phase I/II dose escalation trial of Udenafil in adolescents with single ventricle physiology after Fontan palliation was conducted.

The trial was conducted over a 5 month period, with an additional 3 month follow-up period for adverse events (AE). The 36 subjects enrolled in the trial were comprised of 6 cohorts, as described in Table 1.

TABLE 1

| Dose escalation design | | | | | | |
|---|---|---|---|---|---|---|
| | Cohort 1 | Cohort 2 | Cohort 3 | Cohort 4 | Cohort 5 | Cohort 6 |
| Dose | 37.5 mg daily | 37.5 mg twice daily | 87.5 mg daily | 87.5 mg twice daily | 125 mg daily | Control (no drug) |
| N | 6 | 6 | 6 | 6 | 6 | 6 |

The goals for this trial were to assess the safety of udenafil at multiple dose levels over a five-day period, the pharmacokinetic profile of udenafil in adolescents with Fontan physiology, and the short-term effect of udenafil on pharmacodynamic measures of exercise capacity, ventricular performance, and vascular function.

Multiple doses of udenafil or a pharmaceutically acceptable salt thereof were administered to male and female Fontan patients who are 14-18 years of age.

Inclusion Criteria for the trial were:
Males and females with Fontan physiology who are 14-18 years of age.
Willingness to return to center to complete blood draws and exercise tests as described in the study protocol.
Patients must agree to abstain from alcohol, caffeinated beverages, and grapefruit juice for the duration of the trial.

Informed assent from subject and informed consent from parent/legal guardian as appropriate.

Exclusion Criteria for the study include:
Non-cardiac medical, psychiatric, and/or social disorder that would prevent successful completion of planned study testing or would invalidate its results.
Height<132 cm (minimum height requirement for exercise stress testing).
Known Fontan baffle obstruction, branch pulmonary artery stenosis, or pulmonary vein stenosis resulting in a mean gradient of >4 mmHg between the regions proximal and distal to the obstruction.
Single lung physiology.
Severe ventricular dysfunction or valvular regurgitation (systemic atrioventricular or semilunar valve) determined from review of the echocardiogram performed in closest proximity to study enrollment.
Significant renal (serum creatinine>2.0), hepatic (serum AST and/or ALT>3 times upper limit of normal), gastrointestinal or biliary disorders that could impair absorption, metabolism or excretion of orally administered medications, based on laboratory assessment at the time of screening visit.
Hospitalization for acute decompensated heart failure within the 12 months preceding study screening.
A diagnosis of active protein-losing enteropathy or plastic bronchitis.
Active evaluation or listing for heart transplant.
History of use of a PDE5 inhibitor within three months of study screening.
Concurrent illness that, in the opinion of the investigator, precludes participation.
Current therapy with alpha-blockers or nitrates.
Pregnancy at the time of enrollment.
Latex allergy.

Table 2 presents baseline characteristics of 36 enrolled subjects—in aggregate (2nd column) and for each of the 6 individual cohorts. Median age of enrolled subjects is 16 years (with the range from 14 to 18 years), 58% were male, 78% were white and 6% were Hispanic. There were no significant differences in baseline characteristics among the cohorts (right column).

TABLE 2

| Baseline Characteristics for Enrolled Subjects | | | | | | | | |
|---|---|---|---|---|---|---|---|---|
| Characteristic | Overall (N = 36) | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) | P-value* |
| Age, year | 15.8 ± 1.3 | 15.5 ± 1.0 | 16.2 ± 0.8 | 15.0 ± 0.9 | 15.5 ± 1.8 | 16.5 ± 1.5 | 16.2 ± 1.2 | 0.319 |
| Median (Interquartile Range) | 16 (15, 17) | 16 (15, 16) | 16 (16, 17) | 15 (14, 16) | 15 (14, 17) | 17 (16, 18) | 16 (15, 17) | 0.309 |

TABLE 2-continued

Baseline Characteristics for Enrolled Subjects

| Characteristic | Overall (N = 36) | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) | P-value* |
|---|---|---|---|---|---|---|---|---|
| Range, Min-Max | 14-18 | 14-17 | 15-17 | 14-16 | 14-18 | 14-18 | 15-18 | |
| Male | 21 (58.3%) | 4 (66.7%) | 3 (50.0%) | 3 (50.0%) | 3 (50.0%) | 4 (66.7%) | 4 (66.7%) | 1.000 |
| Hispanic or Latino/Latina | 2 (5.7%) | 1 (16.7%) | 1 (16.7%) | 0 (0.0%) | 0 (0.0%) | 0 (0.0%) | 0 (0.0%) | 1.000 |
| Race | | | | | | | | 0.453 |
| White/Caucasian | 28 (77.8%) | 3 (50.0%) | 4 (66.7%) | 6 (100.0%) | 6 (100.0%) | 4 (66.7%) | 5 (83.3%) | |
| Black/African American | 3 (8.3%) | 2 (33.3%) | 1 (16.7%) | 0 (0.0%) | 0 (0.0%) | 0 (0.0%) | 0 (0.0%) | |
| Other/Unknown | 4 (11.1%) | 1 (16.7%) | 1 (16.7%) | 0 (0.0%) | 0 (0.0%) | 1 (16.7%) | 1 (16.7%) | |
| Height, cm | 165.7 ± 10.1 | 161.0 ± 12.9 | 164.9 ± 10.9 | 168.6 ± 7.8 | 164.7 ± 14.2 | 171.3 ± 7.8 | 163.6 ± 5.6 | 0.585 |
| Weight, kg | 62.4 ± 15.9 | 72.5 ± 27.1 | 56.3 ± 7.7 | 66.8 ± 11.0 | 62.0 ± 15.5 | 61.9 ± 9.0 | 54.9 ± 16.8 | 0.425 |
| Body mass index, kg/m² | 22.6 ± 5.0 | 27.2 ± 8.1 | 20.8 ± 3.2 | 23.4 ± 3.2 | 22.6 ± 4.8 | 21.0 ± 2.0 | 20.3 ± 4.8 | 0.157 |

*P-values for continuous variables were calculated by ANOVA for parametric analysis or Kruskal-Wallis test for non-parametric analysis.
P-values for categorical variables were calculated by Fisher's exact test.

Example 2

Safety and Adverse Events

The purpose of this example was to describe and evaluate the safety of the udenafil compositions administered in the study described in Example 1.

Tables 3-6 present numbers of subjects reporting at least one AE; data are presented by treatment group. The counts are presented by AE category (Table 3) and by preferred term (Table 6). Tables 3-6 report all AEs by category (Table 3), serious AEs (Table 4), non-serious AEs (Table 5), and all AEs by preferred term (Table 6). No serious AEs were reported.

TABLE 3

Adverse Events by Category

| AE Category | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Subjects Reporting at Least One Adverse Event | 5 (83%) | 6 (100%) | 6 (100%) | 5 (83%) | 6 (100%) | 1 (17%) |
| Allergy/Immunology | 1 (17%) | 0 (0%) | 1 (17%) | 0 (0%) | 0 (0%) | 0 (0%) |
| Auditory/ocular | 0 (0%) | 0 (0%) | 0 (0%) | 0 (0%) | 0 (0%) | 0 (0%) |
| Cardiovascular | 0 (0%) | 0 (0%) | 0 (0%) | 0 (0%) | 0 (0%) | 1 (17%) |
| Endocrine/metabolic | 0 (0%) | 0 (0%) | 0 (0%) | 0 (0%) | 1 (17%) | 0 (0%) |
| Gastrointestinal | 2 (33%) | 1 (17%) | 1 (17%) | 1 (17%) | 3 (50%) | 0 (0%) |
| Hematological | 0 (0%) | 1 (17%) | 0 (0%) | 0 (0%) | 1 (17%) | 0 (0%) |
| Hepatobiliary/pancreas | 0 (0%) | 0 (0%) | 0 (0%) | 0 (0%) | 0 (0%) | 0 (0%) |
| Infection | 0 (0%) | 0 (0%) | 0 (0%) | 1 (17%) | 0 (0%) | 0 (0%) |
| Musculoskeletal/skin | 1 (17%) | 1 (17%) | 1 (17%) | 2 (33%) | 2 (33%) | 0 (0%) |
| Neurological/psychiatric | 3 (50%) | 3 (50%) | 5 (83%) | 2 (33%) | 5 (83%) | 0 (0%) |
| Pulmonary/upper respiratory | 2 (33%) | 3 (50%) | 1 (17%) | 1 (17%) | 1 (17%) | 0 (0%) |
| Renal/genitourinary | 0 (0%) | 2 (33%) | 1 (17%) | 0 (0%) | 0 (0%) | 0 (0%) |
| Sexual/reproductive function | 0 (0%) | 0 (0%) | 0 (0%) | 5 (83%) | 2 (33%) | 0 (0%) |
| Vascular | 1 (17%) | 2 (33%) | 4 (67%) | 1 (17%) | 1 (17%) | 0 (0%) |
| Other | 0 (0%) | 2 (33%) | 4 (67%) | 3 (50%) | 2 (33%) | 0 (0%) |

At each level of summation, subjects reporting more than one adverse event are counted only once.
N = number of subjects in each cohort.
n (%) = number and percentage of subjects in category and cohort (n/N × 100)

TABLE 4

Serious Adverse Events

| AE Category | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Subjects Reporting at Least One Adverse Event | 0 (0%) | 0 (0%) | 0 (0%) | 0 (0%) | 0 (0%) | 0 (0%) |

Serious adverse events were not reported for this trial.
At each level of summation, subjects reporting more than one adverse event are counted only once.
N = number of subjects in each cohort.
n (%) = number and percentage of subjects in category and cohort (n/N × 100)

TABLE 5

Non-Serious Adverse Events

| AE Category | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Subjects Reporting at Least One Adverse Event | 5 (83%) | 6 (100%) | 6 (100%) | 5 (83%) | 6 (100%) | 1 (17%) |

At each level of summation, subjects reporting more than one adverse event are counted only once.
N = number of subjects in each cohort.
n (%) = number and percentage of subjects in category and cohort (n/N × 100)

TABLE 6

Adverse Events by Preferred Term

| Preferred Term | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Subjects Reporting at Least One Adverse Event | 5 (83%) | 6 (100%) | 6 (100%) | 5 (83%) | 6 (100%) | 1 (17%) |
| Abdominal discomfort | 1 (17%) | 0 (0%) | 0 (0%) | 1 (17%) | 1 (17%) | 0 (0%) |
| Abdominal pain upper | 0 (0%) | 0 (0%) | 0 (0%) | 0 (0%) | 1 (17%) | 0 (0%) |
| Back pain | 0 (0%) | 0 (0%) | 0 (0%) | 1 (17%) | 0 (0%) | 0 (0%) |
| Chest pain | 0 (0%) | 0 (0%) | 0 (0%) | 0 (0%) | 1 (17%) | 0 (0%) |
| Diarrhoea | 0 (0%) | 0 (0%) | 0 (0%) | 0 (0%) | 1 (17%) | 0 (0%) |
| Dizziness | 0 (0%) | 0 (0%) | 0 (0%) | 1 (17%) | 1 (17%) | 0 (0%) |
| Dry mouth | 0 (0%) | 0 (0%) | 1 (17%) | 0 (0%) | 0 (0%) | 0 (0%) |
| Dysmenorrhoea | 0 (0%) | 1 (17%) | 0 (0%) | 0 (0%) | 0 (0%) | 0 (0%) |
| Dyspnoea | 1 (17%) | 1 (17%) | 0 (0%) | 0 (0%) | 0 (0%) | 0 (0%) |
| Epistaxis | 0 (0%) | 1 (17%) | 0 (0%) | 0 (0%) | 2 (33%) | 0 (0%) |
| Face oedema | 0 (0%) | 0 (0%) | 0 (0%) | 0 (0%) | 1 (17%) | 0 (0%) |
| Fatigue | 0 (0%) | 1 (17%) | 0 (0%) | 1 (17%) | 0 (0%) | 0 (0%) |
| Flushing | 1 (17%) | 2 (33%) | 4 (67%) | 2 (33%) | 1 (17%) | 0 (0%) |
| Head injury | 0 (0%) | 0 (0%) | 1 (17%) | 0 (0%) | 0 (0%) | 0 (0%) |
| Headache | 3 (50%) | 4 (67%) | 4 (67%) | 4 (67%) | 5 (83%) | 0 (0%) |
| Injection site pain | 1 (17%) | 0 (0%) | 0 (0%) | 0 (0%) | 0 (0%) | 0 (0%) |
| Lacrimation increased | 0 (0%) | 0 (0%) | 1 (17%) | 0 (0%) | 0 (0%) | 0 (0%) |
| Migraine | 0 (0%) | 0 (0%) | 0 (0%) | 0 (0%) | 1 (17%) | 0 (0%) |
| Motion sickness | 0 (0%) | 0 (0%) | 1 (17%) | 0 (0%) | 0 (0%) | 0 (0%) |
| Myalgia | 0 (0%) | 1 (17%) | 0 (0%) | 0 (0%) | 0 (0%) | 0 (0%) |
| Nasal congestion | 3 (50%) | 2 (33%) | 2 (33%) | 1 (17%) | 1 (17%) | 0 (0%) |
| Nasopharyngitis | 0 (0%) | 1 (17%) | 0 (0%) | 0 (0%) | 0 (0%) | 0 (0%) |

At each level of summation, subjects reporting more than one adverse event are counted only once.
N = number of subjects in each cohort.
n (%) = number and percentage of subjects in category and cohort (n/N × 100)

Table 7 presents narratives for all adverse events (limited to non-serious at the moment of writing) classified by cohort, subject, AE term, and preferred term.

TABLE 7

| Cohort | Subject ID* | Adverse Event Term// Preferred Term | Onset Date | Resolution Date | Severity | Related to Study Drug | Outcome | Med.[1] | Disc.[2] |
|---|---|---|---|---|---|---|---|---|---|
| 37.5 mg daily | T12 | Nausea // Nausea | Aug. 5, 2014 | Aug. 5, 2014 | Moderate | Possibly | Resolved without sequelae | No | No |
| | | Nausea // Nausea | | | Mild | None | Resolved without sequelae | No | NA |
| | | Headache // Headache | Aug. 2, 2014 | Aug. 2, 2014 | Mild | Possibly | Resolved without sequelae | No | No |
| | | Headache // Headache | Aug. 5, 2014 | Aug. 5, 2014 | Moderate | Possibly | Resolved without sequelae | No | No |
| | | headache // Headache | Aug. 6, 2014 | Aug. 7, 2014 | Moderate | Possibly | Resolved without sequelae | No | NA |
| | | Headache // Headache | Aug. 4, 2014 | Aug. 4, 2014 | Moderate | Possibly | Resolved without sequelae | No | No |
| | | headache // Headache | Aug. 7, 2014 | Aug. 7, 2014 | Moderate | Possibly | Resolved without sequelae | No | NA |
| | | Stuffy nose // Nasal congestion | Aug. 22, 2014 | Aug. 29, 2014 | Mild | None | Resolved without sequelae | No | NA |
| | T13 | Stomach discomfort // Abdominal discomfort | Aug. 1, 2014 | Aug. 1, 2014 | Moderate | None | Resolved without sequelae | No | No |
| | | Headache // Headache | Aug. 2, 2014 | Aug. 5, 2014 | Moderate | Possibly | Resolved without sequelae | No | No |
| | | Headache // Headache | Aug. 7, 2014 | | Moderate | Possibly | Resolved without sequelae | No | No |
| | | Headaches // Headache | | | Mild | Possibly | Ongoing | Yes | NA |
| | | Shortness of breath // Dyspnoea | Aug. 1, 2014 | Aug. 1, 2014 | Severe | None | Resolved without sequelae | No | No |
| | | Congestion (Nose) // Nasal congestion | Aug. 5, 2014 | | Moderate | Possibly | Resolved without sequelae | No | No |
| | T14 | Flushing // Flushing | Aug. 1, 2014 | Aug. 1, 2014 | Mild | Probably | Resolved without sequelae | No | No |
| | | Flushing // Flushing | Aug. 2, 2014 | Aug. 3, 2014 | Mild | Probably | Resolved without sequelae | No | No |
| | | Headache // Headache | Aug. 1, 2014 | Aug. 1, 2014 | Moderate | Possibly | Resolved without sequelae | Yes | No |
| | T15 | Pain/other // Injection site pain | Aug. 5, 2014 | Aug. 8, 2014 | Moderate | None | Resolved without sequelae | Yes | No |
| | T16 | nasal congestion // Nasal congestion | Aug. 4, 2014 | Aug. 5, 2014 | Mild | None | Resolved without sequelae | No | No |
| 37.5 mg twice daily | T21 | Nose bleed // Epistaxis | | | Moderate | None | Resolved without sequelae | Yes | NA |
| 37.5 mg twice daily | T22 | Shortness of breath // Dyspnoea | Nov. 5, 2014 | Nov. 5, 2014 | Moderate | None | Resolved without sequelae | Yes | NA |
| | | upper respiratory infection // Upper respiratory tract infection | Nov. 2, 2014 | | Mild | None | Resolved without sequelae | No | NA |
| | | Facial flushing // Flushing | Aug. 9, 2014 | Aug. 9, 2014 | Mild | Possibly | Resolved without sequelae | No | No |
| | T23 | Headache // Headache | Aug. 8, 2014 | Aug. 9, 2014 | Mild | Possibly | Resolved without sequelae | No | No |
| | | congestion (stuffy nose) // Nasal congestion | Aug. 8, 2014 | Aug. 8, 2014 | Mild | Possibly | Resolved without sequelae | No | No |
| | | cold/congestion // Nasopharyngitis | Sep. 14, 2014 | Sep. 19, 2014 | Mild | None | Resolved without sequelae | No | NA |
| | | Menstrual Cramps // Dysmenorrhoea | Aug. 11, 2014 | Aug. 16, 2014 | Mild | None | Resolved without sequelae | Yes | No |
| | | Facial flushing // Flushing | Aug. 10, 2014 | Aug. 10, 2014 | Mild | Possibly | Resolved without sequelae | No | No |
| | T24 | Nausea // Nausea | Aug. 10, 2014 | Aug. 10, 2014 | Mild | Possibly | Resolved without sequelae | No | No |
| | | Nausea // Nausea | Aug. 11, 2014 | Aug. 11, 2014 | Mild | Possibly | Resolved without sequelae | No | No |
| | | Soreness in chest and arms // Myalgia | Aug. 10, 2014 | Aug. 11, 2014 | Mild | Possibly | Resolved without sequelae | No | No |
| | | Headache // Headache | Aug. 8, 2014 | Aug. 8, 2014 | Mild | Possibly | Resolved without sequelae | No | No |
| | | Headache // Headache | | | Mild | Possibly | Resolved without sequelae | Yes | NA |
| | | Congestion (stuffy nose) // Nasal congestion | Aug. 10, 2014 | Aug. 10, 2014 | Mild | Possibly | Resolved without sequelae | No | No |
| | | Sponatenous penile erection // Spontaneous penile erection | Aug. 11, 2014 | Aug. 11, 2014 | Mild | Possibly | Resolved without sequelae | No | No |

TABLE 7-continued

| Cohort | Subject ID* | Adverse Event Term// Preferred Term | Onset Date | Resolution Date | Severity | Related to Study Drug | Outcome | Med.[1] | Disc.[2] |
|---|---|---|---|---|---|---|---|---|---|
| | | Spontaneous penile erection // Spontaneous penile erection | Aug. 14, 2014 | Aug. 14, 2014 | Mild | Possibly | Resolved without sequelae | No | NA |
| | T25 | Headache // Headache | Aug. 8, 2014 | Aug. 8, 2014 | Mild | Possibly | Resolved without sequelae | No | No |
| | T26 | Headache // Headache | Aug. 9, 2014 | Aug. 9, 2014 | Mild | Possibly | Resolved without sequelae | Yes | No |
| | | Sinus pain // Sinus headache | Aug. 9, 2014 | Nov. 18, 2014 | Mild | Probably | Resolved without sequelae | No | No |
| | | Headache // Headache | Aug. 10, 2014 | Sep. 22, 2014 | Moderate | Probably | Resolved without sequelae | Yes | No |
| | | Fatigue // Fatigue | Aug. 9, 2014 | Aug. 10, 2014 | Mild | Possibly | Resolved without sequelae | No | No |
| 87.5 mg daily | T31 | headache // Headache | Aug. 15, 2014 | Aug. 15, 2014 | Mild | Probably | Resolved without sequelae | No | No |
| | | headache // Headache | Aug. 17, 2014 | Aug. 17, 2014 | Mild | Probably | Resolved without sequelae | No | No |
| | | headache // Headache | Aug. 18, 2014 | Aug. 18, 2014 | Moderate | Probably | Resolved without sequelae | No | No |
| | | congestion (stuffy nose) // Sinus congestion | Aug. 15, 2014 | Aug. 21, 2014 | Mild | Probably | Resolved without sequelae | No | No |
| | | Facial flushing // Flushing | Aug. 18, 2014 | Aug. 18, 2014 | Mild | Probably | Resolved without sequelae | No | No |
| | | spotty vision // Vision blurred | Aug. 15, 2014 | Aug. 15, 2014 | Mild | None | Resolved without sequelae | No | No |
| | T32 | motion sickness // Motion sickness | Aug. 15, 2014 | Aug. 15, 2014 | Mild | Possibly | Resolved without sequelae | No | No |
| | | headache // Headache | Aug. 15, 2014 | Aug. 15, 2014 | Mild | Probably | Resolved without sequelae | Yes | No |
| | | headache // Headache | Aug. 16, 2014 | Aug. 16, 2014 | Mild | Probably | Resolved without sequelae | No | No |
| | | headache // Headache | Aug. 17, 2014 | Aug. 17, 2014 | Mild | Probably | Resolved without sequelae | No | No |
| | | dry mouth // Dry mouth | Aug. 16, 2014 | Aug. 16, 2014 | Mild | Possibly | Resolved without sequelae | No | No |
| | T33 | Head Injury // Head injury | Aug. 21, 2014 | Aug. 22, 2014 | Mild | None | Resolved without sequelae | Yes | NA |
| | | facial flushing // Flushing | Aug. 16, 2014 | Aug. 22, 2014 | Mild | Probably | Resolved without sequelae | No | No |
| | | tearing // Lacrimation increased | Aug. 16, 2014 | Aug. 22, 2014 | Mild | None | Resolved without sequelae | No | No |
| | T34 | Sleepiness // Somnolence | Aug. 16, 2014 | Aug. 25, 2014 | Mild | Possibly | Resolved without sequelae | No | No |
| | | Spontaneous penile erection // Spontaneous penile erection | Aug. 20, 2014 | Aug. 20, 2014 | Mild | Possibly | Resolved without sequelae | No | No |
| | | Facial Flushing // Flushing | Aug. 16, 2014 | Aug. 21, 2014 | Mild | Possibly | Resolved with sequelae | No | No |
| | T35 | headache // Headache | Aug. 15, 2014 | Aug. 15, 2014 | Mild | Probably | Resolved without sequelae | No | No |
| 87.5 mg daily | | headache // Headache | Aug. 16, 2014 | Aug. 16, 2014 | Mild | Probably | Resolved without sequelae | No | No |
| | | stuffy nose // Nasal congestion | Sep. 20, 2014 | Sep. 23, 2014 | Moderate | None | Resolved without sequelae | No | NA |
| | T36 | Nasal congestion // Nasal congestion | Aug. 19, 2014 | Aug. 21, 2014 | Mild | Possibly | Resolved without sequelae | Yes | No |
| | | Flushing // Flushing | Aug. 15, 2014 | Aug. 15, 2014 | Mild | Probably | Resolved without sequelae | No | No |
| | | Headache // Headache | Aug. 15, 2014 | Aug. 15, 2014 | Mild | Possibly | Resolved without sequelae | No | No |
| 87.5 mg twice daily | T42 | Nausea/vomiting // Nausea | Aug. 26, 2014 | Aug. 26, 2014 | Mild | Possibly | Resolved without sequelae | No | No |
| | | Stomach discomfort // Abdominal discomfort | Aug. 22, 2014 | Aug. 22, 2014 | Mild | Possibly | Resolved with sequelae | No | No |
| | | Facial flushing // Flushing | Aug. 26, 2014 | Aug. 26, 2014 | Mild | Probably | Resolved without sequelae | No | No |
| | | Headache // Headache | Aug. 23, 2014 | Aug. 23, 2014 | Mild | Probably | Resolved without sequelae | No | No |
| | | Headache // Headache | Aug. 25, 2014 | Aug. 25, 2014 | Mild | Probably | Resolved without sequelae | No | No |
| | | Headache // Headache | Aug. 24, 2014 | Aug. 24, 2014 | Mild | Probably | Resolved without sequelae | No | No |
| | | Headache // Headache | Aug. 26, 2014 | Aug. 26, 2014 | Mild | Probably | Resolved without sequelae | No | No |
| | T43 | headache // Headache | Aug. 22, 2014 | Aug. 22, 2014 | Moderate | Possibly | Resolved without sequelae | No | No |

TABLE 7-continued

| Cohort | Subject ID* | Adverse Event Term// Preferred Term | Onset Date | Resolution Date | Severity | Related to Study Drug | Outcome | Med.[1] | Disc.[2] |
|---|---|---|---|---|---|---|---|---|---|
| | | headache // Headache | Aug. 23, 2014 | Aug. 23, 2014 | Mild | Possibly | Resolved without sequelae | No | No |
| | | headache // Headache | Aug. 24, 2014 | Aug. 24, 2014 | Mild | Possibly | Resolved without sequelae | No | No |
| | T44 | Stuffy nose // Nasal congestion | Aug. 22, 2014 | Aug. 22, 2014 | Mild | Possibly | Resolved without sequelae | No | No |
| | | Stuffy nose // Nasal congestion | Aug. 25, 2014 | Aug. 25, 2014 | Mild | Possibly | Resolved without sequelae | No | No |
| | | Stuffy nose // Nasal congestion | Aug. 25, 2014 | Aug. 25, 2014 | Mild | Possibly | Resolved without sequelae | No | No |
| | | spontaneous penile erection // Spontaneous penile erection | Aug. 21, 2014 | Aug. 21, 2014 | Mild | Possibly | Resolved without sequelae | No | No |
| 87.5 mg twice daily | | Spontaneous penile erection // Spontaneous penile erection | Aug. 21, 2014 | Aug. 21, 2014 | Mild | Possibly | Resolved without sequelae | No | No |
| | | Spontaneous penile erection // Spontaneous penile erection | Aug. 22, 2014 | Aug. 22, 2014 | Mild | Possibly | Resolved without sequelae | No | No |
| | | spontaneous penile erection // Spontaneous penile erection | Aug. 25, 2014 | Aug. 25, 2014 | Mild | Possibly | Resolved without sequelae | No | No |
| | | Spontaneous penile erection // Spontaneous penile erection | Aug. 26, 2014 | Aug. 26, 2014 | Mild | Possibly | Resolved without sequelae | No | No |
| | | Headache // Headache | Aug. 21, 2014 | Aug. 21, 2014 | Mild | Possibly | Resolved without sequelae | No | No |
| | | Headache // Headache | Aug. 22, 2014 | Aug. 22, 2014 | Mild | Possibly | Resolved without sequelae | No | No |
| | | headache // Headache | Aug. 23, 2014 | Aug. 23, 2014 | Mild | Possibly | Resolved without sequelae | No | No |
| | | headache // Headache | Aug. 24, 2014 | Aug. 24, 2014 | Mild | Possibly | Resolved without sequelae | No | No |
| | T45 | spontaneous penile erection // Spontaneous penile erection | Aug. 31, 2014 | Aug. 31, 2014 | Mild | Possibly | Resolved without sequelae | No | No |
| | T46 | sinusitis // Sinusitis | Aug. 26, 2014 | | Moderate | None | Ongoing | No | No |
| | | back pain // Back pain | Aug. 31, 2014 | Sep. 5, 2014 | Mild | Possibly | Resolved without sequelae | No | No |
| | | flushing // Flushing | Aug. 30, 2014 | Aug. 31, 2014 | Mild | Possibly | Resolved without sequelae | No | No |
| | | flushing // Flushing | Sep. 1, 2014 | Sep. 1, 2014 | Mild | Possibly | Resolved without sequelae | No | No |
| | | flushing // Flushing | Sep. 2, 2014 | Sep. 2, 2014 | Mild | Possibly | Resolved without sequelae | No | No |
| | | flushing // Flushing | Sep. 2, 2014 | Sep. 3, 2014 | Mild | Possibly | Resolved without sequelae | No | No |
| | | Headache // Headache | Aug. 29, 2014 | Sep. 5, 2014 | Mild | Possibly | Resolved without sequelae | Yes | No |
| | | Dizziness // Dizziness | Aug. 30, 2014 | Aug. 30, 2014 | Mild | Possibly | Resolved with sequelae | No | No |
| | | flushing // Flushing | Aug. 31, 2014 | Aug. 31, 2014 | Mild | Probably | Resolved without sequelae | No | No |
| 87.5 mg twice daily | | Fatigue // Fatigue | Aug. 30, 2014 | Sep. 1, 2014 | Mild | Possibly | Resolved without sequelae | No | No |
| | | edema // Oedema | Sep. 2, 2014 | | Mild | Possibly | Ongoing | No | No |
| 125 mg daily | T51 | headache // Headache | | Feb. 9, 2015 | Mild | None | Resolved without sequelae | Yes | NA |
| | T52 | Increased frequency of spontaneous penile erections // Spontaneous penile erection | Nov. 7, 2014 | Nov. 8, 2014 | Mild | Possibly | Resolved without sequelae | No | No |
| | T53 | Diarrhea // Diarrhoea | Dec. 6, 2014 | Dec. 6, 2014 | Mild | Possibly | Resolved without sequelae | No | No |
| | | Epistaxis // Epistaxis | Dec. 7, 2014 | Dec. 7, 2014 | Mild | None | Resolved without sequelae | No | No |
| | | Headache // Headache | Dec. 3, 2014 | Dec. 3, 2014 | Mild | Possibly | Resolved without sequelae | No | No |
| | | Spontaneous penile erection // Spontaneous penile erection | Dec. 4, 2014 | Dec. 4, 2014 | Mild | Possibly | Resolved without sequelae | No | No |
| | | Flushing // Flushing | Dec. 4, 2014 | Dec. 8, 2014 | Mild | Probably | Resolved without sequelae | No | No |
| | T54 | Headache // Headache | Oct. 10, 2014 | Oct. 10, 2014 | Moderate | Possibly | Resolved without sequelae | No | No |
| | | headache // Headache | Oct. 12, 2014 | Oct. 13, 2014 | Mild | Possibly | Resolved without sequelae | Yes | No |
| | | headaches // Headache | Oct. 13, 2014 | | Moderate | Possibly | Ongoing | Yes | No |
| | | Dizziness // Dizziness | Oct. 13, 2014 | Oct. 13, 2014 | Moderate | Possibly | Resolved without sequelae | Yes | No |
| | | Stuffy nose (congestion) // Nasal congestion | Oct. 11, 2014 | | Mild | Possibly | Ongoing | No | No |

TABLE 7-continued

| Cohort | Subject ID* | Adverse Event Term// Preferred Term | Onset Date | Resolution Date | Severity | Related to Study Drug | Outcome | Med.[1] | Disc.[2] |
|---|---|---|---|---|---|---|---|---|---|
| | | Nose bleed // Epistaxis | Oct. 13, 2014 | Oct. 13, 2014 | Mild | Possibly | Resolved without sequelae | No | No |
| | | itchy throat // Throat irritation | Oct. 30, 2014 | Oct. 30, 2014 | Moderate | None | Resolved without sequelae | Yes | NA |
| | T55 | Nausea // Nausea | Jan. 13, 2015 | Jan. 14, 2015 | Moderate | None | Resolved without sequelae | Yes | NA |
| | | Swollen/puffy cheeks // Face oedema | Nov. 29, 2014 | Nov. 29, 2014 | Mild | None | Resolved without sequelae | No | No |
| | | headache // Headache | Nov. 25, 2014 | Nov. 25, 2014 | Mild | Possibly | Resolved without sequelae | No | No |
| 125 mg daily | | Headache // Headache | Nov. 27, 2014 | Nov. 27, 2014 | Mild | Possibly | Resolved without sequelae | No | No |
| | | Headache // Headache | Nov. 28, 2014 | Nov. 28, 2014 | Mild | Possibly | Resolved without sequelae | No | No |
| | | Headache // Headache | Nov. 30, 2014 | Nov. 30, 2014 | Mild | Possibly | Resolved without sequelae | No | NA |
| | | Migraine Headache // Migraine | Jan. 12, 2015 | Jan. 14, 2015 | Moderate | None | Resolved without sequelae | Yes | NA |
| | T56 | Stomach discomfort // Abdominal discomfort | Sep. 8, 2014 | Sep. 8, 2014 | Mild | Possibly | Resolved without sequelae | No | No |
| | | Stomach discomfort // Abdominal pain upper | Sep. 6, 2014 | Sep. 10, 2014 | Mild | Possibly | Resolved with sequelae | No | No |
| | | Stomach discomfort // Abdominal discomfort | Sep. 7, 2014 | Sep. 7, 2014 | Mild | Possibly | Resolved without sequelae | No | No |
| | | Stomach discomfort // Abdominal discomfort | Sep. 9, 2014 | Sep. 9, 2014 | Mild | Possibly | Resolved without sequelae | No | No |
| | | Chest pain // Chest pain | Sep. 6, 2014 | Sep. 7, 2014 | Mild | Possibly | Resolved with sequelae | No | No |
| | | Rash // Rash | Sep. 7, 2014 | Sep. 10, 2014 | Mild | Possibly | Resolved without sequelae | No | No |
| | | Chest pain // Chest pain | Sep. 6, 2014 | Sep. 6, 2014 | Mild | None | Resolved without sequelae | No | No |
| | | Rash // Rash | Sep. 8, 2014 | Sep. 8, 2014 | Mild | None | Resolved without sequelae | No | No |
| | | Rash // Rash | Sep. 9, 2014 | Sep. 9, 2014 | Mild | None | Resolved without sequelae | No | No |
| | | Rash // Rash | Sep. 11, 2014 | Sep. 11, 2014 | Mild | None | Resolved without sequelae | No | No |
| | | Rash // Rash | Sep. 12, 2014 | Sep. 12, 2014 | Mild | None | Resolved without sequelae | No | No |
| | | Headache // Headache | Sep. 6, 2014 | Sep. 6, 2014 | Mild | Probably | Resolved with sequelae | Yes | No |
| | | Headache // Headache | Sep. 7, 2014 | Sep. 7, 2014 | Mild | Possibly | Resolved without sequelae | Yes | No |
| | | Headache // Headache | Sep. 8, 2014 | Sep. 8, 2014 | Mild | Possibly | Resolved without sequelae | No | No |
| | | Headache // Headache | Sep. 9, 2014 | Sep. 9, 2014 | Mild | Probably | Resolved without sequelae | Yes | No |
| | | Headache // Headache | Sep. 10, 2014 | Sep. 10, 2014 | Mild | Probably | Resolved without sequelae | Yes | No |
| Exercise testing only | C2 | Ventricular arrhythmia // Ventricular arrhythmia | Dec. 11, 2014 | Dec. 11, 2014 | Mild | None | Resolved without sequelae | No | NA |
| | | Ventricular Tachycardia // Ventricular tachycardia | Dec. 15, 2014 | Dec. 15, 2014 | Mild | None | Resolved without sequelae | No | NA |

Table 8 presents numbers of subjects with number of AEs≥n, where n=1, 2, . . . , 6, by treatment group.

TABLE 8

Adverse Events by Treatment Group

| N (%) of Subjects Reporting at Least: | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| 1 event | 5 (83%) | 6 (100%) | 6 (100%) | 5 (83%) | 6 (100%) | 1 (17%) |
| 2 events | 3 (50%) | 4 (67%) | 6 (100%) | 4 (67%) | 4 (67%) | 1 (17%) |
| 3 events | 3 (50%) | 4 (67%) | 6 (100%) | 4 (67%) | 4 (67%) | 0 (0%) |
| 4 events | 2 (33%) | 3 (50%) | 2 (33%) | 3 (50%) | 4 (67%) | 0 (0%) |

TABLE 8-continued

Adverse Events by Treatment Group

| N (%) of Subjects Reporting at Least: | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| 5 events | 2 (33%) | 2 (33%) | 2 (33%) | 3 (50%) | 4 (67%) | 0 (0%) |
| 6 events | 2 (33%) | 1 (17%) | 1 (17%) | 3 (50%) | 3 (50%) | 0 (0%) |

Tables 9-12 present AEs by preferred term (similar to Table 6), but additionally report the number of subjects with an AE and the number of AEs (Table 9), the number of AE events/subjects grouped by treatment group and by related (including possibly or probably) vs. not related to the study drug (Table 10), mild vs. moderate/severe (Table 11), and expected vs. unexpected AEs (Table 12).

TABLE 9

Adverse Events by Preferred Term

| Preferred Term, #Events (#Subjects) | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Abdominal discomfort | 1 (1) | 0 (0) | 0 (0) | 1 (1) | 3 (1) | 0 (0) |
| Abdominal pain upper | 0 (0) | 0 (0) | 0 (0) | 0 (0) | 1 (1) | 0 (0) |
| Back pain | 0 (0) | 0 (0) | 0 (0) | 1 (1) | 0 (0) | 0 (0) |
| Chest pain | 0 (0) | 0 (0) | 0 (0) | 0 (0) | 2 (1) | 0 (0) |
| Diarrhoea | 0 (0) | 0 (0) | 0 (0) | 0 (0) | 1 (1) | 0 (0) |
| Dizziness | 0 (0) | 0 (0) | 0 (0) | 1 (1) | 1 (1) | 0 (0) |
| Dry mouth | 0 (0) | 0 (0) | 1 (1) | 0 (0) | 0 (0) | 0 (0) |
| Dysmenorrhoea | 0 (0) | 1 (1) | 0 (0) | 0 (0) | 0 (0) | 0 (0) |
| Dyspnoea | 1 (1) | 1 (1) | 0 (0) | 0 (0) | 0 (0) | 0 (0) |
| Epistaxis | 0 (0) | 1 (1) | 0 (0) | 0 (0) | 2 (2) | 0 (0) |
| Face oedema | 0 (0) | 0 (0) | 0 (0) | 0 (0) | 1 (1) | 0 (0) |
| Fatigue | 0 (0) | 1 (1) | 0 (0) | 1 (1) | 0 (0) | 0 (0) |
| Flushing | 2 (1) | 2 (2) | 4 (4) | 6 (2) | 1 (1) | 0 (0) |
| Head injury | 0 (0) | 0 (0) | 1 (1) | 0 (0) | 0 (0) | 0 (0) |
| Headache | 9 (3) | 6 (4) | 9 (4) | 12 (4) | 14 (5) | 0 (0) |
| Injection site pain | 1 (1) | 0 (0) | 0 (0) | 0 (0) | 0 (0) | 0 (0) |
| Lacrimation increased | 0 (0) | 0 (0) | 1 (1) | 0 (0) | 0 (0) | 0 (0) |
| Migraine | 0 (0) | 0 (0) | 0 (0) | 0 (0) | 1 (1) | 0 (0) |

TABLE 9-continued

Adverse Events by Preferred Term

| Preferred Term, #Events (#Subjects) | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Motion sickness | 0 (0) | 0 (0) | 1 (1) | 0 (0) | 0 (0) | 0 (0) |
| Myalgia | 0 (0) | 1 (1) | 0 (0) | 0 (0) | 0 (0) | 0 (0) |
| Nasal congestion | 3 (3) | 2 (2) | 2 (2) | 3 (1) | 1 (1) | 0 (0) |
| Nasopharyngitis | 0 (0) | 1 (1) | 0 (0) | 0 (0) | 0 (0) | 0 (0) |
| Nausea | 2 (1) | 2 (1) | 0 (0) | 1 (1) | 1 (1) | 0 (0) |
| Oedema | 0 (0) | 0 (0) | 0 (0) | 1 (1) | 0 (0) | 0 (0) |
| Rash | 0 (0) | 0 (0) | 0 (0) | 0 (0) | 5 (1) | 0 (0) |
| Sinus congestion | 0 (0) | 0 (0) | 1 (1) | 0 (0) | 0 (0) | 0 (0) |
| Sinus headache | 0 (0) | 1 (1) | 0 (0) | 0 (0) | 0 (0) | 0 (0) |
| Sinusitis | 0 (0) | 0 (0) | 0 (0) | 1 (1) | 0 (0) | 0 (0) |
| Somnolence | 0 (0) | 0 (0) | 1 (1) | 0 (0) | 0 (0) | 0 (0) |
| Spontaneous penile erection | 0 (0) | 2 (1) | 1 (1) | 6 (2) | 2 (2) | 0 (0) |
| Throat irritation | 0 (0) | 0 (0) | 0 (0) | 0 (0) | 1 (1) | 0 (0) |
| Upper respiratory tract infection | 0 (0) | 1 (1) | 0 (0) | 0 (0) | 0 (0) | 0 (0) |
| Ventricular arrhythmia | 0 (0) | 0 (0) | 0 (0) | 0 (0) | 0 (0) | 1 (1) |
| Ventricular tachycardia | 0 (0) | 0 (0) | 0 (0) | 0 (0) | 0 (0) | 1 (1) |
| Vision blurred | 0 (0) | 0 (0) | 1 (1) | 0 (0) | 0 (0) | 0 (0) |

TABLE 10

Related and Unrelated AEs

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Drug related* | Not related | Drug related* | Not related | Drug related* | Not related | Drug related* | Not related | Drug related* | Not related | Drug related* | Not related |
| Abdominal discomfort | 0 (0) | 1 (1) | 0 (0) | 0 (0) | 0 (0) | 0 (0) | 1 (1) | 0 (0) | 3 (1) | 0 (0) | 0 (0) | 0 (0) |
| Abdominal pain upper | 0 (0) | 0 (0) | 0 (0) | 0 (0) | 0 (0) | 0 (0) | 0 (0) | 0 (0) | 1 (1) | 0 (0) | 0 (0) | 0 (0) |
| Back pain | 0 (0) | 0 (0) | 0 (0) | 0 (0) | 0 (0) | 0 (0) | 1 (1) | 0 (0) | 0 (0) | 0 (0) | 0 (0) | 0 (0) |
| Chest pain | 0 (0) | 0 (0) | 0 (0) | 0 (0) | 0 (0) | 0 (0) | 0 (0) | 0 (0) | 1 (1) | 1 (1) | 0 (0) | 0 (0) |
| Diarrhoea | 0 (0) | 0 (0) | 0 (0) | 0 (0) | 0 (0) | 0 (0) | 0 (0) | 0 (0) | 1 (1) | 0 (0) | 0 (0) | 0 (0) |
| Dizziness | 0 (0) | 0 (0) | 0 (0) | 0 (0) | 0 (0) | 0 (0) | 1 (1) | 0 (0) | 1 (1) | 0 (0) | 0 (0) | 0 (0) |
| Dry mouth | 0 (0) | 0 (0) | 0 (0) | 0 (0) | 1 (1) | 0 (0) | 0 (0) | 0 (0) | 0 (0) | 0 (0) | 0 (0) | 0 (0) |
| Dysmenorrhoea | 0 (0) | 0 (0) | 0 (0) | 1 (1) | 0 (0) | 0 (0) | 0 (0) | 0 (0) | 0 (0) | 0 (0) | 0 (0) | 0 (0) |
| Dyspnoea | 0 (0) | 1 (1) | 1 (1) | 0 (0) | 0 (0) | 0 (0) | 0 (0) | 0 (0) | 0 (0) | 0 (0) | 0 (0) | 0 (0) |
| Epistaxis | 0 (0) | 0 (0) | 0 (0) | 1 (1) | 0 (0) | 0 (0) | 0 (0) | 0 (0) | 1 (1) | 1 (1) | 0 (0) | 0 (0) |
| Face oedema | 0 (0) | 0 (0) | 0 (0) | 0 (0) | 0 (0) | 0 (0) | 0 (0) | 0 (0) | 1 (1) | 0 (0) | 0 (0) | 0 (0) |

TABLE 10-continued

Related and Unrelated AEs

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Drug related* | Not related | Drug related* | Not related | Drug related* | Not related | Drug related* | Not related | Drug related* | Not related | Drug related* | Not related |
| Fatigue | 0 (0) | 0 (0) | 1 (1) | 0 (0) | 0 (0) | 0 (0) | 1 (1) | 0 (0) | 0 (0) | 0 (0) | 0 (0) | 0 (0) |
| Flushing | 2 (1) | 0 (0) | 2 (2) | 0 (0) | 4 (4) | 0 (0) | 6 (2) | 0 (0) | 1 (1) | 0 (0) | 0 (0) | 0 (0) |
| Head injury | 0 (0) | 0 (0) | 0 (0) | 0 (0) | 0 (0) | 1 (1) | 0 (0) | 0 (0) | 0 (0) | 0 (0) | 0 (0) | 0 (0) |
| Headache | 9 (3) | 0 (0) | 6 (4) | 0 (0) | 9 (4) | 0 (0) | 12 (4) | 0 (0) | 13 (4) | 1 (1) | 0 (0) | 0 (0) |
| Injection site pain | 0 (0) | 1 (1) | 0 (0) | 0 (0) | 0 (0) | 0 (0) | 0 (0) | 0 (0) | 0 (0) | 0 (0) | 0 (0) | 0 (0) |
| Lacrimation increased | 0 (0) | 0 (0) | 0 (0) | 0 (0) | 0 (0) | 1 (1) | 0 (0) | 0 (0) | 0 (0) | 0 (0) | 0 (0) | 0 (0) |
| Migraine | 0 (0) | 0 (0) | 0 (0) | 0 (0) | 0 (0) | 0 (0) | 0 (0) | 0 (0) | 0 (0) | 1 (1) | 0 (0) | 0 (0) |
| Motion sickness | 0 (0) | 0 (0) | 0 (0) | 0 (0) | 1 (1) | 0 (0) | 0 (0) | 0 (0) | 0 (0) | 0 (0) | 0 (0) | 0 (0) |
| Myalgia | 0 (0) | 0 (0) | 1 (1) | 0 (0) | 0 (0) | 0 (0) | 0 (0) | 0 (0) | 0 (0) | 0 (0) | 0 (0) | 0 (0) |
| Nasal congestion | 1 (1) | 2 (2) | 2 (2) | 0 (0) | 1 (1) | 1 (1) | 3 (1) | 0 (0) | 1 (1) | 0 (0) | 0 (0) | 0 (0) |
| Nasopharyngitis | 0 (0) | 0 (0) | 0 (0) | 1 (1) | 0 (0) | 0 (0) | 0 (0) | 0 (0) | 0 (0) | 0 (0) | 0 (0) | 0 (0) |
| Nausea | 1 (1) | 1 (1) | 2 (1) | 0 (0) | 0 (0) | 0 (0) | 1 (1) | 0 (0) | 0 (0) | 1 (1) | 0 (0) | 0 (0) |
| Oedema | 0 (0) | 0 (0) | 0 (0) | 0 (0) | 0 (0) | 0 (0) | 1 (1) | 0 (0) | 0 (0) | 0 (0) | 0 (0) | 0 (0) |
| Rash | 0 (0) | 0 (0) | 0 (0) | 0 (0) | 0 (0) | 0 (0) | 0 (0) | 0 (0) | 1 (1) | 4 (1) | 0 (0) | 0 (0) |
| Sinus congestion | 0 (0) | 0 (0) | 0 (0) | 0 (0) | 1 (1) | 0 (0) | 0 (0) | 0 (0) | 0 (0) | 0 (0) | 0 (0) | 0 (0) |
| Sinus headache | 0 (0) | 0 (0) | 1 (1) | 0 (0) | 0 (0) | 0 (0) | 0 (0) | 0 (0) | 0 (0) | 0 (0) | 0 (0) | 0 (0) |
| Sinusitis | 0 (0) | 0 (0) | 0 (0) | 0 (0) | 0 (0) | 0 (0) | 0 (0) | 1 (1) | 0 (0) | 0 (0) | 0 (0) | 0 (0) |
| Somnolence | 0 (0) | 0 (0) | 0 (0) | 0 (0) | 1 (1) | 0 (0) | 0 (0) | 0 (0) | 0 (0) | 0 (0) | 0 (0) | 0 (0) |
| Spontaneous penile erection | 0 (0) | 0 (0) | 2 (1) | 0 (0) | 1 (1) | 0 (0) | 6 (2) | 0 (0) | 2 (2) | 0 (0) | 0 (0) | 0 (0) |
| Throat irritation | 0 (0) | 0 (0) | 0 (0) | 0 (0) | 0 (0) | 0 (0) | 0 (0) | 0 (0) | 0 (0) | 1 (1) | 0 (0) | 0 (0) |
| Upper respiratory tract infection | 0 (0) | 0 (0) | 0 (0) | 1 (1) | 0 (0) | 0 (0) | 0 (0) | 0 (0) | 0 (0) | 0 (0) | 0 (0) | 0 (0) |
| Ventricular arrhythmia | 0 (0) | 0 (0) | 0 (0) | 0 (0) | 0 (0) | 0 (0) | 0 (0) | 0 (0) | 0 (0) | 0 (0) | 0 (0) | 1 (1) |
| Ventricular tachycardia | 0 (0) | 0 (0) | 0 (0) | 0 (0) | 0 (0) | 0 (0) | 0 (0) | 0 (0) | 0 (0) | 0 (0) | 0 (0) | 1 (1) |
| Vision blurred | 0 (0) | 0 (0) | 0 (0) | 0 (0) | 0 (0) | 1 (1) | 0 (0) | 0 (0) | 0 (0) | 0 (0) | 0 (0) | 0 (0) |
| Total | 13 (3) | 6 (4) | 17 (5) | 5 (3) | 19 (6) | 4 (3) | 33 (5) | 1 (1) | 26 (5) | 11 (5) | 0 (0) | 2 (1) |

*Drug related = possibly related, probably related or related to study drug
Out of all 36 study subjects, none had adverse events related to the study drug, and 11, 21 and 17 subjects had adverse events that were probably related, possibly related and unrelated to the study drug, respectively.

TABLE 11

AEs by Severity

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Mild | Moderate/ severe | Mild | Moderate/ severe | Mild | Moderate/ severe | Mild | Moderate/ severe | Mild | Moderate/ severe | Mild | Moderate/ severe |
| Abdominal discomfort | 0 (0) | 1 (1) | 0 (0) | 0 (0) | 0 (0) | 0 (0) | 1 (1) | 0 (0) | 3 (1) | 0 (0) | 0 (0) | 0 (0) |
| Abdominal pain upper | 0 (0) | 0 (0) | 0 (0) | 0 (0) | 0 (0) | 0 (0) | 0 (0) | 0 (0) | 1 (1) | 0 (0) | 0 (0) | 0 (0) |
| Back pain | 0 (0) | 0 (0) | 0 (0) | 0 (0) | 0 (0) | 0 (0) | 1 (1) | 0 (0) | 0 (0) | 0 (0) | 0 (0) | 0 (0) |
| Chest pain | 0 (0) | 0 (0) | 0 (0) | 0 (0) | 0 (0) | 0 (0) | 0 (0) | 0 (0) | 2 (1) | 0 (0) | 0 (0) | 0 (0) |
| Diarrhoea | 0 (0) | 0 (0) | 0 (0) | 0 (0) | 0 (0) | 0 (0) | 0 (0) | 0 (0) | 1 (1) | 0 (0) | 0 (0) | 0 (0) |
| Dizziness | 0 (0) | 0 (0) | 0 (0) | 0 (0) | 0 (0) | 0 (0) | 1 (1) | 0 (0) | 0 (0) | 1 (1) | 0 (0) | 0 (0) |
| Dry mouth | 0 (0) | 0 (0) | 0 (0) | 0 (0) | 1 (1) | 0 (0) | 0 (0) | 0 (0) | 0 (0) | 0 (0) | 0 (0) | 0 (0) |
| Dysmenorrhoea | 0 (0) | 0 (0) | 1 (1) | 0 (0) | 0 (0) | 0 (0) | 0 (0) | 0 (0) | 0 (0) | 0 (0) | 0 (0) | 0 (0) |
| Dyspnoea | 0 (0) | 1 (1) | 0 (0) | 1 (1) | 0 (0) | 0 (0) | 0 (0) | 0 (0) | 0 (0) | 0 (0) | 0 (0) | 0 (0) |
| Epistaxis | 0 (0) | 0 (0) | 0 (0) | 1 (1) | 0 (0) | 0 (0) | 0 (0) | 0 (0) | 2 (2) | 0 (0) | 0 (0) | 0 (0) |
| Face oedema | 0 (0) | 0 (0) | 0 (0) | 0 (0) | 0 (0) | 0 (0) | 0 (0) | 0 (0) | 1 (1) | 0 (0) | 0 (0) | 0 (0) |

TABLE 11-continued

AEs by Severity

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Mild | Moderate/severe | Mild | Moderate/severe | Mild | Moderate/severe | Mild | Moderate/severe | Mild | Moderate/severe | Mild | Moderate/severe |
| Fatigue | 0 (0) | 0 (0) | 1 (1) | 0 (0) | 0 (0) | 0 (0) | 1 (1) | 0 (0) | 0 (0) | 0 (0) | 0 (0) | 0 (0) |
| Flushing | 2 (1) | 0 (0) | 2 (2) | 0 (0) | 4 (4) | 0 (0) | 6 (2) | 0 (0) | 1 (1) | 0 (0) | 0 (0) | 0 (0) |
| Head injury | 0 (0) | 0 (0) | 0 (0) | 0 (0) | 1 (1) | 0 (0) | 0 (0) | 0 (0) | 0 (0) | 0 (0) | 0 (0) | 0 (0) |
| Headache | 2 (2) | 7 (3) | 5 (4) | 1 (1) | 8 (4) | 1 (1) | 11 (4) | 1 (1) | 12 (5) | 2 (1) | 0 (0) | 0 (0) |
| Injection site pain | 0 (0) | 1 (1) | 0 (0) | 0 (0) | 0 (0) | 0 (0) | 0 (0) | 0 (0) | 0 (0) | 0 (0) | 0 (0) | 0 (0) |
| Lacrimation increased | 0 (0) | 0 (0) | 0 (0) | 0 (0) | 1 (1) | 0 (0) | 0 (0) | 0 (0) | 0 (0) | 0 (0) | 0 (0) | 0 (0) |
| Migraine | 0 (0) | 0 (0) | 0 (0) | 0 (0) | 0 (0) | 0 (0) | 0 (0) | 0 (0) | 1 (1) | 0 (0) | 0 (0) | 0 (0) |
| Motion sickness | 0 (0) | 0 (0) | 0 (0) | 0 (0) | 1 (1) | 0 (0) | 0 (0) | 0 (0) | 0 (0) | 0 (0) | 0 (0) | 0 (0) |
| Myalgia | 0 (0) | 0 (0) | 1 (1) | 0 (0) | 0 (0) | 0 (0) | 0 (0) | 0 (0) | 0 (0) | 0 (0) | 0 (0) | 0 (0) |
| Nasal congestion | 2 (2) | 1 (1) | 2 (2) | 0 (0) | 1 (1) | 1 (1) | 3 (1) | 0 (0) | 1 (1) | 0 (0) | 0 (0) | 0 (0) |
| Nasopharyngitis | 0 (0) | 0 (0) | 1 (1) | 0 (0) | 0 (0) | 0 (0) | 0 (0) | 0 (0) | 0 (0) | 0 (0) | 0 (0) | 0 (0) |
| Nausea | 1 (1) | 1 (1) | 2 (1) | 0 (0) | 0 (0) | 0 (0) | 1 (1) | 0 (0) | 0 (0) | 1 (1) | 0 (0) | 0 (0) |
| Oedema | 0 (0) | 0 (0) | 0 (0) | 0 (0) | 0 (0) | 0 (0) | 1 (1) | 0 (0) | 0 (0) | 0 (0) | 0 (0) | 0 (0) |
| Rash | 0 (0) | 0 (0) | 0 (0) | 0 (0) | 0 (0) | 0 (0) | 0 (0) | 0 (0) | 5 (1) | 0 (0) | 0 (0) | 0 (0) |
| Sinus congestion | 0 (0) | 0 (0) | 0 (0) | 0 (0) | 1 (1) | 0 (0) | 0 (0) | 0 (0) | 0 (0) | 0 (0) | 0 (0) | 0 (0) |
| Sinus headache | 0 (0) | 0 (0) | 1 (1) | 0 (0) | 0 (0) | 0 (0) | 0 (0) | 0 (0) | 0 (0) | 0 (0) | 0 (0) | 0 (0) |
| Sinusitis | 0 (0) | 0 (0) | 0 (0) | 0 (0) | 0 (0) | 0 (0) | 0 (0) | 1 (1) | 0 (0) | 0 (0) | 0 (0) | 0 (0) |
| Somnolence | 0 (0) | 0 (0) | 0 (0) | 0 (0) | 1 (1) | 0 (0) | 0 (0) | 0 (0) | 0 (0) | 0 (0) | 0 (0) | 0 (0) |
| Spontaneous penile erection | 0 (0) | 0 (0) | 2 (1) | 0 (0) | 1 (1) | 0 (0) | 6 (2) | 0 (0) | 2 (2) | 0 (0) | 0 (0) | 0 (0) |
| Throat irritation | 0 (0) | 0 (0) | 0 (0) | 0 (0) | 0 (0) | 0 (0) | 0 (0) | 0 (0) | 1 (1) | 0 (0) | 0 (0) | 0 (0) |
| Upper respiratory tract infection | 0 (0) | 0 (0) | 1 (1) | 0 (0) | 0 (0) | 0 (0) | 0 (0) | 0 (0) | 0 (0) | 0 (0) | 0 (0) | 0 (0) |
| Ventricular arrhythmia | 0 (0) | 0 (0) | 0 (0) | 0 (0) | 0 (0) | 0 (0) | 0 (0) | 0 (0) | 0 (0) | 0 (0) | 1 (1) | 0 (0) |
| Ventricular tachycardia | 0 (0) | 0 (0) | 0 (0) | 0 (0) | 0 (0) | 0 (0) | 0 (0) | 0 (0) | 0 (0) | 0 (0) | 1 (1) | 0 (0) |
| Vision blurred | 0 (0) | 0 (0) | 0 (0) | 0 (0) | 1 (1) | 0 (0) | 0 (0) | 0 (0) | 0 (0) | 0 (0) | 0 (0) | 0 (0) |
| Total | 7 (4) | 12 (4) | 19 (5) | 3 (3) | 21 (6) | 2 (2) | 32 (5) | 2 (2) | 31 (6) | 6 (2) | 2 (1) | 0 (0) |

Out of all 36 study subjects, 27 had mild adverse events, 13 had moderate and 1 subject had a severe adverse event.

TABLE 12

AEs by Expectedness

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Expected | Not Expected | Expected | Not Expected | Expected | Not Expected | Expected | Not Expected | Expected | Not Expected | Expected | Not Expected |
| Abdominal discomfort | 0 (0) | 1 (1) | 0 (0) | 0 (0) | 0 (0) | 0 (0) | 1 (1) | 0 (0) | 3 (1) | 0 (0) | 0 (0) | 0 (0) |
| Abdominal pain upper | 0 (0) | 0 (0) | 0 (0) | 0 (0) | 0 (0) | 0 (0) | 0 (0) | 0 (0) | 1 (1) | 0 (0) | 0 (0) | 0 (0) |
| Back pain | 0 (0) | 0 (0) | 0 (0) | 0 (0) | 0 (0) | 0 (0) | 1 (1) | 0 (0) | 0 (0) | 0 (0) | 0 (0) | 0 (0) |
| Chest pain | 0 (0) | 0 (0) | 0 (0) | 0 (0) | 0 (0) | 0 (0) | 0 (0) | 0 (0) | 0 (0) | 2 (1) | 0 (0) | 0 (0) |
| Diarrhoea | 0 (0) | 0 (0) | 0 (0) | 0 (0) | 0 (0) | 0 (0) | 0 (0) | 0 (0) | 1 (1) | 0 (0) | 0 (0) | 0 (0) |
| Dizziness | 0 (0) | 0 (0) | 0 (0) | 0 (0) | 0 (0) | 0 (0) | 0 (0) | 1 (1) | 0 (0) | 1 (1) | 0 (0) | 0 (0) |
| Dry mouth | 0 (0) | 0 (0) | 0 (0) | 0 (0) | 0 (0) | 1 (1) | 0 (0) | 0 (0) | 0 (0) | 0 (0) | 0 (0) | 0 (0) |
| Dysmenorrhoea | 0 (0) | 0 (0) | 0 (0) | 1 (1) | 0 (0) | 0 (0) | 0 (0) | 0 (0) | 0 (0) | 0 (0) | 0 (0) | 0 (0) |
| Dyspnoea | 0 (0) | 1 (1) | 0 (0) | 1 (1) | 0 (0) | 0 (0) | 0 (0) | 0 (0) | 0 (0) | 0 (0) | 0 (0) | 0 (0) |
| Epistaxis | 0 (0) | 0 (0) | 0 (0) | 1 (1) | 0 (0) | 0 (0) | 0 (0) | 0 (0) | 0 (0) | 2 (2) | 0 (0) | 0 (0) |
| Face oedema | 0 (0) | 0 (0) | 0 (0) | 0 (0) | 0 (0) | 0 (0) | 0 (0) | 0 (0) | 0 (0) | 1 (1) | 0 (0) | 0 (0) |
| Fatigue | 0 (0) | 0 (0) | 0 (0) | 1 (1) | 0 (0) | 0 (0) | 0 (0) | 1 (1) | 0 (0) | 0 (0) | 0 (0) | 0 (0) |

TABLE 12-continued

AEs by Expectedness

| Preferred Term, #Events (#Subjects) | 37.5 mg daily (N = 6) | | 37.5 mg twice daily (N = 6) | | 87.5 mg daily (N = 6) | | 87.5 mg twice daily (N = 6) | | 125 mg daily (N = 6) | | Exercise only (N = 6) | |
|---|---|---|---|---|---|---|---|---|---|---|---|---|
| | Expected | Not Expected | Expected | Not Expected | Expected | Not Expected | Expected | Not Expected | Expected | Not Expected | Expected | Not Expected |
| Flushing | 2 (1) | 0 (0) | 2 (2) | 0 (0) | 4 (4) | 0 (0) | 5 (2) | 1 (1) | 1 (1) | 0 (0) | 0 (0) | 0 (0) |
| Head injury | 0 (0) | 0 (0) | 0 (0) | 0 (0) | 0 (0) | 1 (1) | 0 (0) | 0 (0) | 0 (0) | 0 (0) | 0 (0) | 0 (0) |
| Headache | 8 (3) | 1 (1) | 5 (4) | 1 (1) | 9 (4) | 0 (0) | 11 (3) | 1 (1) | 13 (5) | 1 (1) | 0 (0) | 0 (0) |
| Injection site pain | 0 (0) | 1 (1) | 0 (0) | 0 (0) | 0 (0) | 0 (0) | 0 (0) | 0 (0) | 0 (0) | 0 (0) | 0 (0) | 0 (0) |
| Lacrimation increased | 0 (0) | 0 (0) | 0 (0) | 0 (0) | 0 (0) | 1 (1) | 0 (0) | 0 (0) | 0 (0) | 0 (0) | 0 (0) | 0 (0) |
| Migraine | 0 (0) | 0 (0) | 0 (0) | 0 (0) | 0 (0) | 0 (0) | 0 (0) | 0 (0) | 0 (0) | 1 (1) | 0 (0) | 0 (0) |
| Motion sickness | 0 (0) | 0 (0) | 0 (0) | 0 (0) | 1 (1) | 0 (0) | 0 (0) | 0 (0) | 0 (0) | 0 (0) | 0 (0) | 0 (0) |
| Myalgia | 0 (0) | 0 (0) | 0 (0) | 1 (1) | 0 (0) | 0 (0) | 0 (0) | 0 (0) | 0 (0) | 0 (0) | 0 (0) | 0 (0) |
| Nasal congestion | 2 (2) | 1 (1) | 2 (2) | 0 (0) | 2 (2) | 0 (0) | 3 (1) | 0 (0) | 1 (1) | 0 (0) | 0 (0) | 0 (0) |
| Nasopharyngitis | 0 (0) | 0 (0) | 1 (1) | 0 (0) | 0 (0) | 0 (0) | 0 (0) | 0 (0) | 0 (0) | 0 (0) | 0 (0) | 0 (0) |
| Nausea | 2 (1) | 0 (0) | 2 (1) | 0 (0) | 0 (0) | 0 (0) | 0 (0) | 1 (1) | 0 (0) | 1 (1) | 0 (0) | 0 (0) |
| Oedema | 0 (0) | 0 (0) | 0 (0) | 0 (0) | 0 (0) | 0 (0) | 0 (0) | 1 (1) | 0 (0) | 0 (0) | 0 (0) | 0 (0) |
| Rash | 0 (0) | 0 (0) | 0 (0) | 0 (0) | 0 (0) | 0 (0) | 0 (0) | 0 (0) | 0 (0) | 5 (1) | 0 (0) | 0 (0) |
| Sinus congestion | 0 (0) | 0 (0) | 0 (0) | 0 (0) | 1 (1) | 0 (0) | 0 (0) | 0 (0) | 0 (0) | 0 (0) | 0 (0) | 0 (0) |
| Sinus headache | 0 (0) | 0 (0) | 1 (1) | 0 (0) | 0 (0) | 0 (0) | 0 (0) | 0 (0) | 0 (0) | 0 (0) | 0 (0) | 0 (0) |
| Sinusitis | 0 (0) | 0 (0) | 0 (0) | 0 (0) | 0 (0) | 0 (0) | 0 (0) | 1 (1) | 0 (0) | 0 (0) | 0 (0) | 0 (0) |
| Somnolence | 0 (0) | 0 (0) | 0 (0) | 0 (0) | 1 (1) | 0 (0) | 0 (0) | 0 (0) | 0 (0) | 0 (0) | 0 (0) | 0 (0) |
| Spontaneous penile erection | 0 (0) | 0 (0) | 2 (1) | 0 (0) | 1 (1) | 0 (0) | 6 (2) | 0 (0) | 2 (2) | 0 (0) | 0 (0) | 0 (0) |
| Throat irritation | 0 (0) | 0 (0) | 0 (0) | 0 (0) | 0 (0) | 0 (0) | 0 (0) | 0 (0) | 0 (0) | 1 (1) | 0 (0) | 0 (0) |
| Upper respiratory tract infection | 0 (0) | 0 (0) | 0 (0) | 1 (1) | 0 (0) | 0 (0) | 0 (0) | 0 (0) | 0 (0) | 0 (0) | 0 (0) | 0 (0) |
| Ventricular arrhythmia | 0 (0) | 0 (0) | 0 (0) | 0 (0) | 0 (0) | 0 (0) | 0 (0) | 0 (0) | 0 (0) | 0 (0) | 1 (1) | 0 (0) |
| Ventricular tachycardia | 0 (0) | 0 (0) | 0 (0) | 0 (0) | 0 (0) | 0 (0) | 0 (0) | 0 (0) | 0 (0) | 0 (0) | 1 (1) | 0 (0) |
| Vision blurred | 0 (0) | 0 (0) | 0 (0) | 0 (0) | 1 (1) | 0 (0) | 0 (0) | 0 (0) | 0 (0) | 0 (0) | 0 (0) | 0 (0) |
| Total | 14 (4) | 5 (3) | 15 (5) | 7 (5) | 18 (6) | 5 (4) | 26 (5) | 8 (2) | 22 (6) | 15 (4) | 2 (1) | 0 (0) |

Out of all 36 study subjects, 27 subjects had expected and 18 had unexpected adverse events.

Table 13 focuses on a subset of Table 7 limited to preferred terms for which AEs happened more than once (either ≥2 AEs for one subject, or ≥2 subjects with at least one AE) in at least one cohort.

TABLE 13

Events That Occurred More Than Once in One Subject or In More Than One Subject

| Preferred Term, #Events (#Subjects) | 37.5 mg daily (N = 6) | 37.5 mg twice daily (N = 6) | 87.5 mg daily (N = 6) | 87.5 mg twice daily (N = 6) | 125 mg daily (N = 6) | Exercise testing only (N = 6) |
|---|---|---|---|---|---|---|
| Abdominal discomfort | 1 (1) | 0 (0) | 0 (0) | 1 (1) | 3 (1) | 0 (0) |
| Chest pain | 0 (0) | 0 (0) | 0 (0) | 0 (0) | 2 (1) | 0 (0) |
| Epistaxis | 0 (0) | 1 (1) | 0 (0) | 0 (0) | 2 (2) | 0 (0) |
| Flushing | 2 (1) | 2 (2) | 4 (4) | 6 (2) | 1 (1) | 0 (0) |
| Headache | 9 (3) | 6 (4) | 9 (4) | 12 (4) | 14 (5) | 0 (0) |
| Nasal congestion | 3 (3) | 2 (2) | 2 (2) | 3 (1) | 1 (1) | 0 (0) |
| Nausea | 2 (1) | 2 (1) | 0 (0) | 1 (1) | 1 (1) | 0 (0) |
| Rash | 0 (0) | 0 (0) | 0 (0) | 0 (0) | 5 (1) | 0 (0) |
| Spontaneous penile erection | 0 (0) | 2 (1) | 1 (1) | 6 (2) | 2 (2) | 0 (0) |

Figure 1:
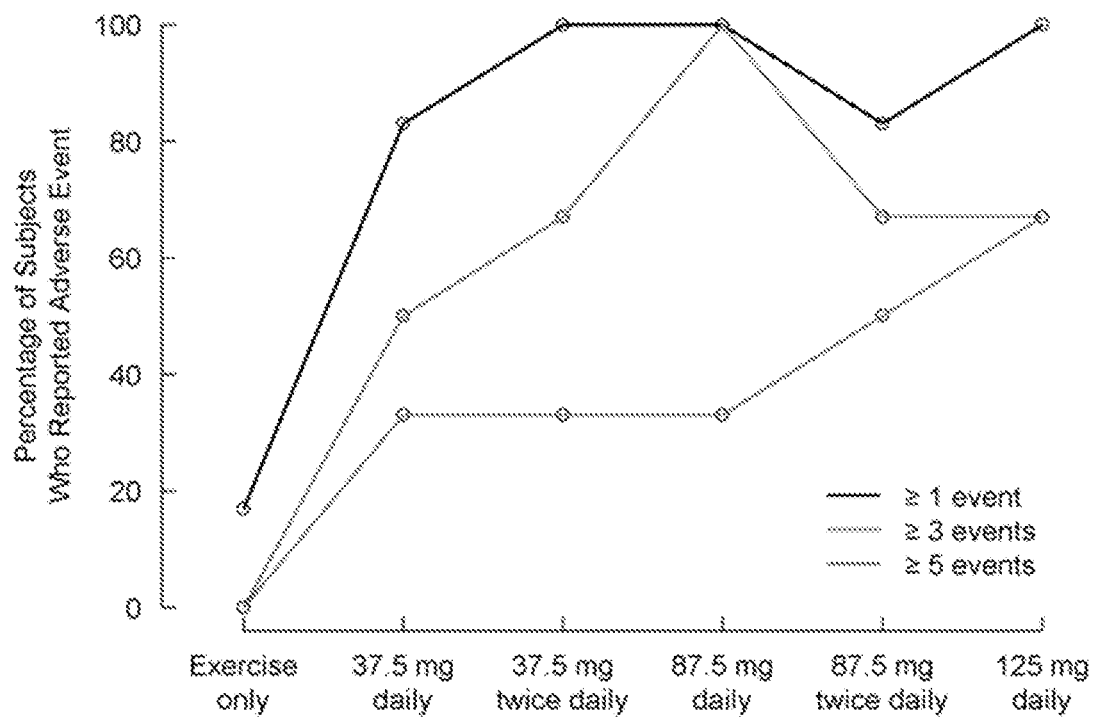
FIG. 1 shows the percentage of subjects who reported at least one, three, or five adverse events by treatment group.

FIG. 1 displays the percent of subjects reporting at least one, three or five adverse events by treatment group (the numbers are taken from Table 6). The cohorts at horizontal axis are sorted from the lowest daily dose at the left (exercise only group; zero dose, though not a placebo) to the highest one-time dose (125 mg) at the right. The percentages vary from 100% to 0% (exercise only group). As expected, the exercise only group features the lowest percentage. The plot doesn't suggest a clear association between the dose and percent of subjects reporting AEs.

Example 3

Exercise Testing

The purpose of this example was to evaluate the efficacy of the treatment protocol described in Example 1 using various exercise testing parameters.

The primary outcome of this arm of the study was maximal VO2 as determined by exercise testing. Table 14 summarizes results for the key outcome from the exercise testing—peak VO2 (limited to the subjects who achieved maximum effort) by treatment group. Out of the 36 subjects enrolled in the trial, 33 reached max effort in the exercise testing at each of the time points, and 31 subjects at both time points. The first two lines present data for baseline and follow-up measurements, while the third line presents differences between the two measurements (change scores, the outcome for this aim). Analysis of variances suggests lack of differences between the change scores (p=0.85).

TABLE 14

Peak VO2 at Maximum Effort, ml/kg/min

| | N | All subjects | N | 37.5 mg daily | N | 37.5 mg twice daily | N | 87.5 mg daily | N | 87.5 mg twice daily | N | 125 mg daily | N | Exercise only | P-value |
|---|---|---|---|---|---|---|---|---|---|---|---|---|---|---|---|
| Baseline measurement | 34 | 28.5 ± 5.8 | 6 | 24.6 ± 6.9 | 6 | 30.4 ± 6.2 | 6 | 28.4 ± 6.2 | 5 | 28.0 ± 5.2 | 5 | 28.6 ± 3.0 | 6 | 30.6 ± 6.2 | 0.542 |
| Follow-up measurement | 33 | 28.2 ± 5.8 | 5 | 24.7 ± 6.7 | 6 | 28.8 ± 8.1 | 6 | 27.1 ± 5.0 | 5 | 28.2 ± 6.0 | 6 | 28.6 ± 3.8 | 5 | 31.8 ± 5.0 | 0.570 |
| Difference, FU – BL | 32 | −0.6 ± 3.3 | 5 | −0.8 ± 1.7 | 6 | −1.6 ± 5.1 | 6 | −1.4 ± 2.5 | 5 | 0.2 ± 5.0 | 5 | 0.9 ± 2.6 | 5 | −0.3 ± 1.8 | 0.851 |

P-values were calculated by ANOVA.
The maximum effort was achieved when the respiratory quotient at peak ≥ 1.1.

Figure 2:
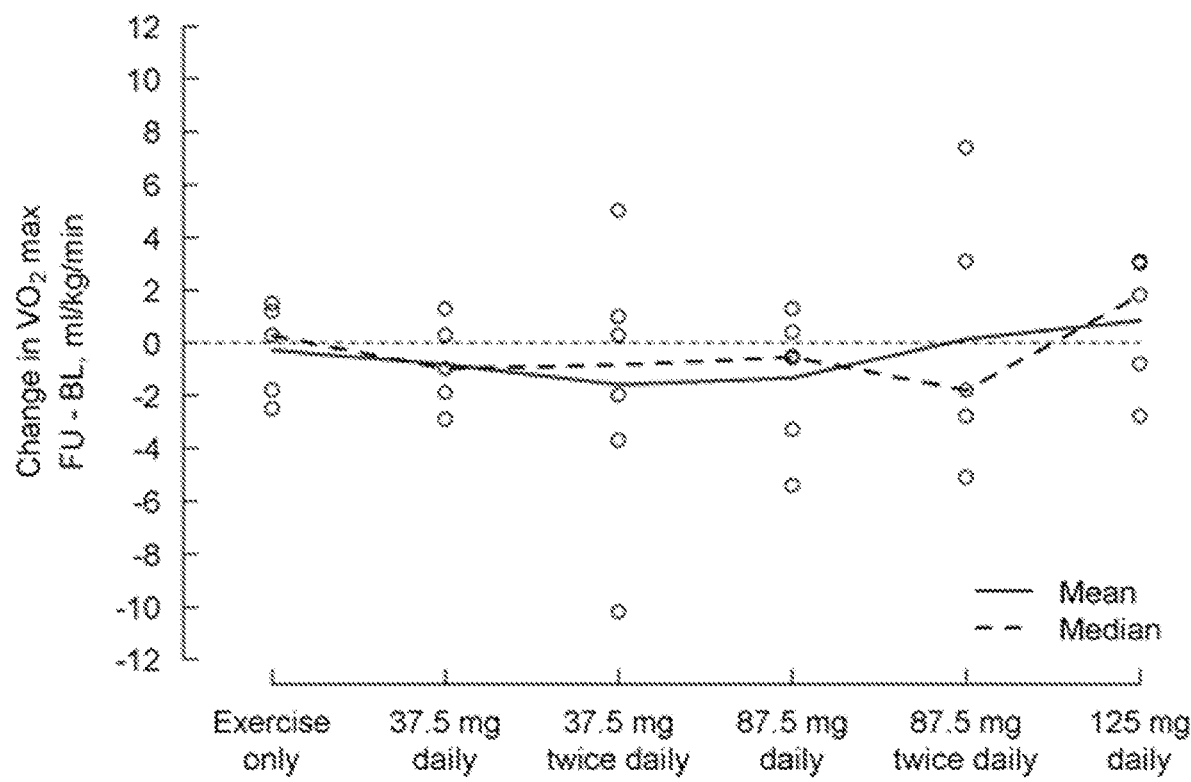
FIG. 2 shows change in peak VO2 (ml/kg/min) at the maximum effort from baseline (day 1) to the last visit (post-medication, day 5) by treatment group, where a positive change indicates an improvement.
Figure 3:
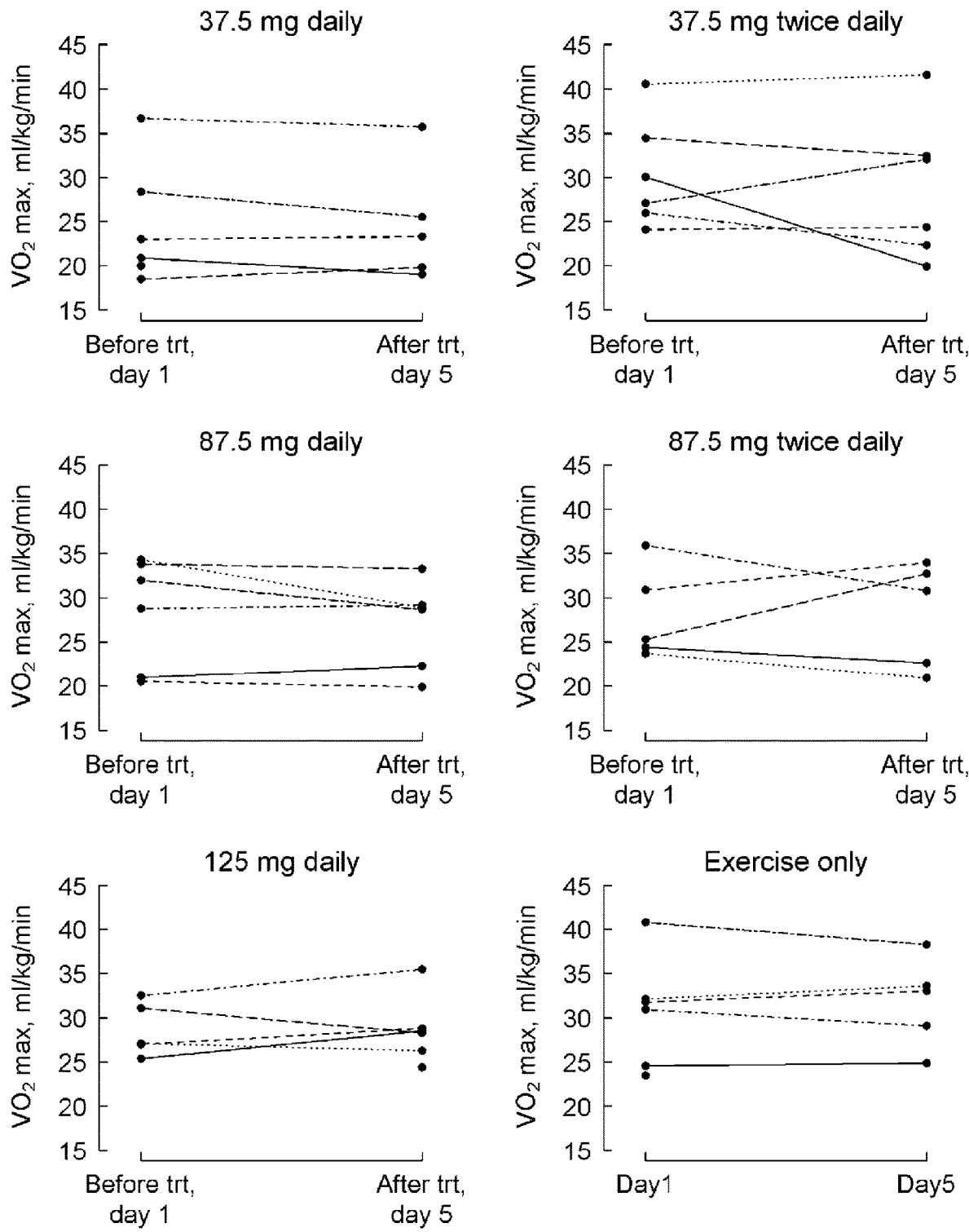
FIG. 3 shows peak VO2 at the maximum effort at baseline (day 1) and at the last visit (post-medication, day 5) by treatment group, where a positive change indicates an improvement.

FIGS. 2 and 3 present the findings for change scores in a visual way (with a positive change indicating an improvement). FIG. 2 displays individual change score for each subject with paired measurements (circles) and two lines with mean and median values. The plots don't suggest that change scores increase with the dose. FIG. 3 displays maximal VO2 values before and after the treatment for each subject and in each cohort.

As expected, baseline and follow-up measurements are strongly correlated, with the correlation coefficient>0.8.

An additional outcome, VO2 at anaerobic threshold, was also measured. Similar analyses were performed for this outcome. Results are presented in Table 15 and FIGS. 4 and 5. Overall results are similar to those for maximal VO2.

TABLE 15

Peak VO2 at Anaerobic Threshold, ml/kg/min

| | N | All subjects | N | 37.5 mg daily | N | 37.5 mg twice daily | N | 87.5 mg daily | N | 87.5 mg twice daily | N | 125 mg daily | N | Exercise only | P-value |
|---|---|---|---|---|---|---|---|---|---|---|---|---|---|---|---|
| Baseline measurement | 36 | 18.6 ± 4.5 | 6 | 17.2 ± 5.0 | 6 | 18.0 ± 3.0 | 6 | 17.6 ± 5.3 | 6 | 18.3 ± 4.6 | 6 | 18.8 ± 1.8 | 6 | 21.7 ± 6.2 | 0.570 |
| Follow-up measurement | 34 | 18.2 ± 4.4 | 5 | 16.3 ± 2.0 | 6 | 18.1 ± 3.0 | 6 | 16.5 ± 4.8 | 6 | 16.5 ± 5.2 | 6 | 20.0 ± 3.2 | 5 | 22.4 ± 5.5 | 0.135 |
| Difference, FU – BL | 34 | −0.3 ± 2.6 | 5 | −0.5 ± 4.1 | 6 | 0.1 ± 1.0 | 6 | −1.1 ± 1.9 | 6 | −1.7 ± 2.1 | 6 | 1.2 ± 1.9 | 5 | 0.1 ± 3.8 | 0.469 |

P-values were calculated by ANOVA.

Figure 4:
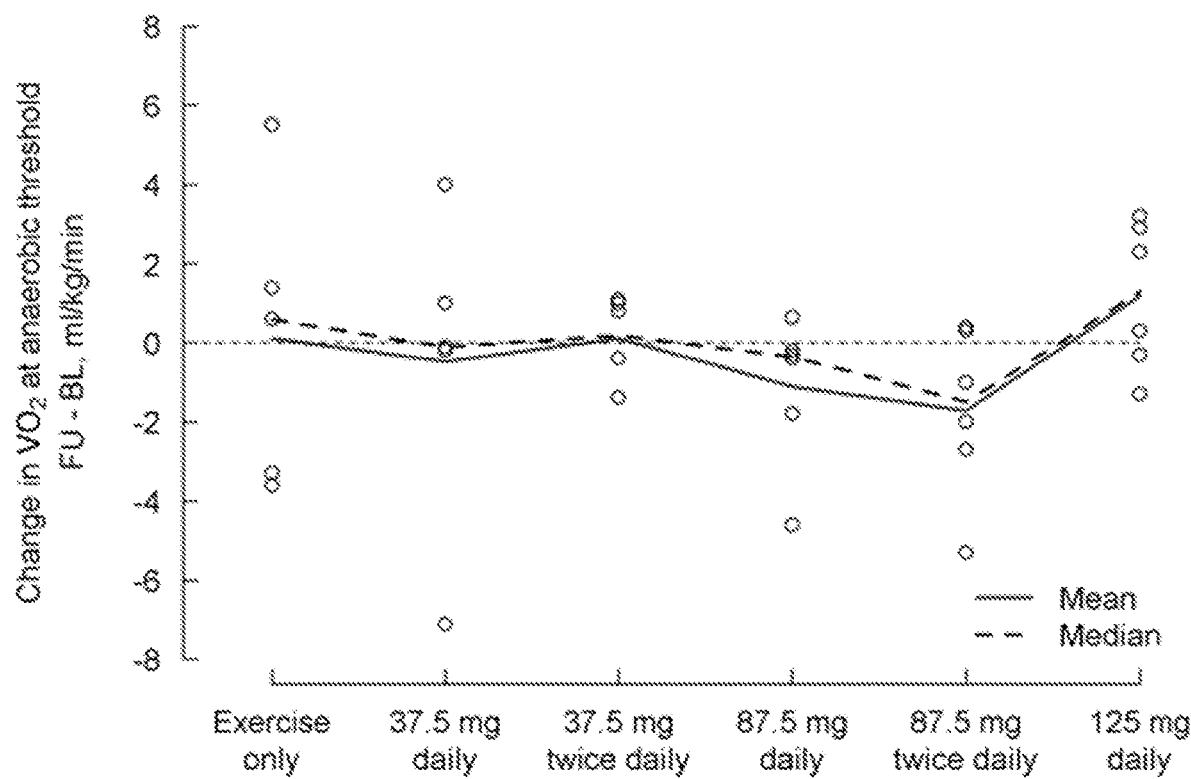
FIG. 4 shows change in VO2 (ml/kg/min) at anaerobic threshold from baseline (day 1) to the last visit (post-medication, day 5) by treatment group, where a positive change indicates an improvement.
Figure 5:
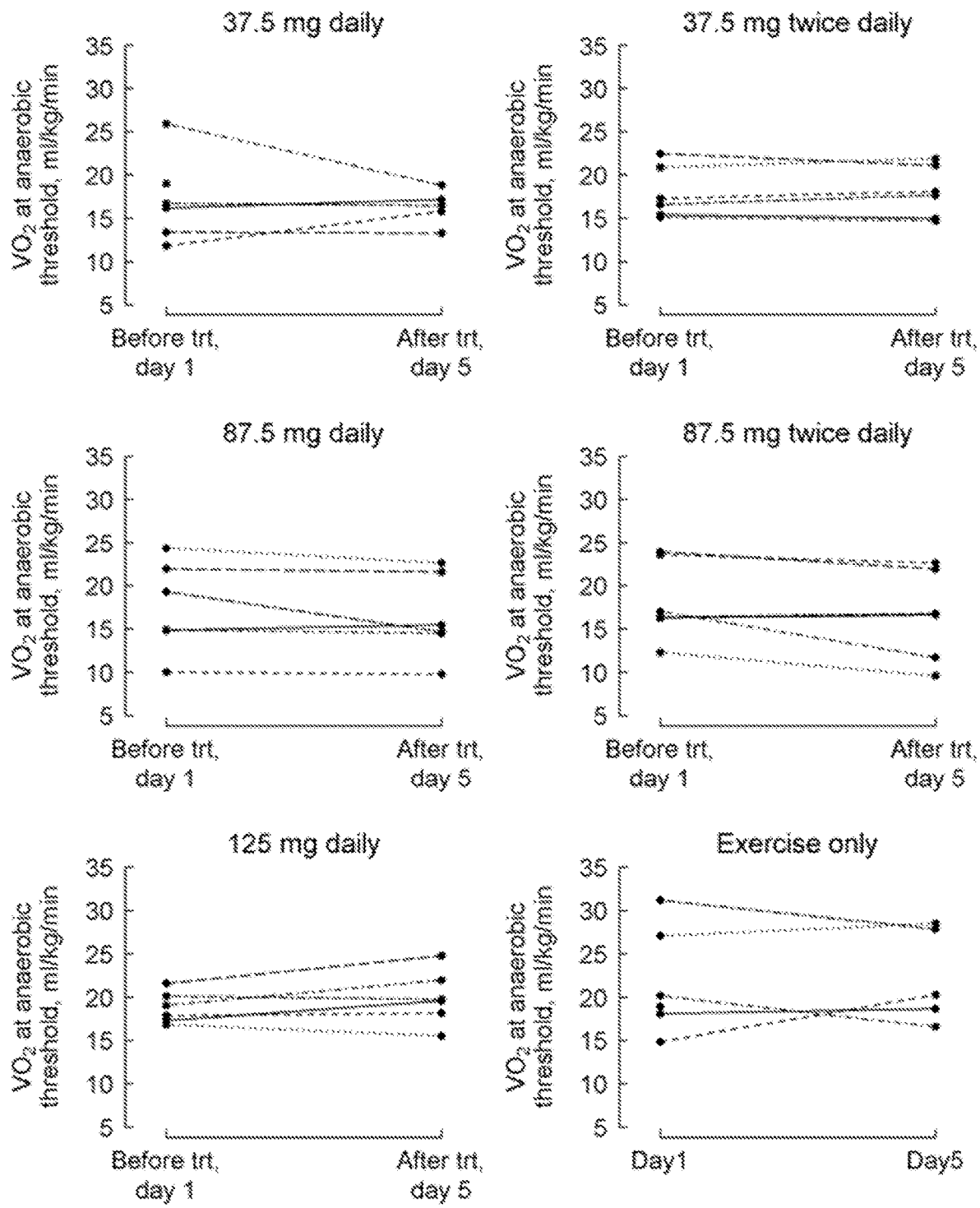
FIG. 5 shows peak VO2 at anaerobic threshold at baseline (day 1) and at the last visit (post-medication, day 5) by treatment group, where a positive change indicates an improvement.

Of note, both exercise outcomes (peak VO2 and VO2 at anaerobic threshold) are highly correlated (with the correlation coefficient at each visit above 0.7), which may explain similarities in the trend lines in FIGS. 2 and 4.

Example 4

Vascular Function Testing

The primary outcome of vascular function was determined according to an endothelial pulse amplitude tonometry (PAT) index as determined by the EndoPAT® device (Itamar Medical, Caesarea, Israel).

Table 16 summarizes the results for the key outcome from the vascular function testing—natural log of Reactive Hyperemia Index (lnRHI) by treatment group. Out of the 30 subjects enrolled in the treatment arms of the trial, 27 subjects had paired measurements with an acceptable quality (with QC score equal to 3 (the best) or 2). The structure of the table is similar to the one for exercise variables.

TABLE 16

Natural Log of Reactive Hyperemia Index

| | N | All subjects | N | 37.5 mg daily | N | 37.5 mg twice daily | N | 87.5 mg daily | N | 87.5 mg twice daily | N | 125 mg daily | P-value |
|---|---|---|---|---|---|---|---|---|---|---|---|---|---|
| Baseline measurement | 28 | 0.52 ± 0.28 | 6 | 0.48 ± 0.31 | 6 | 0.60 ± 0.30 | 6 | 0.41 ± 0.25 | 4 | 0.49 ± 0.12 | 6 | 0.63 ± 0.37 | 0.704 |
| Follow-up measurement | 28 | 0.49 ± 0.28 | 6 | 0.51 ± 0.26 | 6 | 0.53 ± 0.29 | 5 | 0.45 ± 0.31 | 5 | 0.40 ± 0.29 | 6 | 0.52 ± 0.34 | 0.945 |
| Difference, FU − BL | 27 | −0.02 ± 0.30 | 6 | 0.03 ± 0.47 | 6 | −0.07 ± 0.17 | 5 | 0.07 ± 0.22 | 4 | −0.03 ± 0.20 | 6 | −0.10 ± 0.38 | 0.902 |

Figure 6:
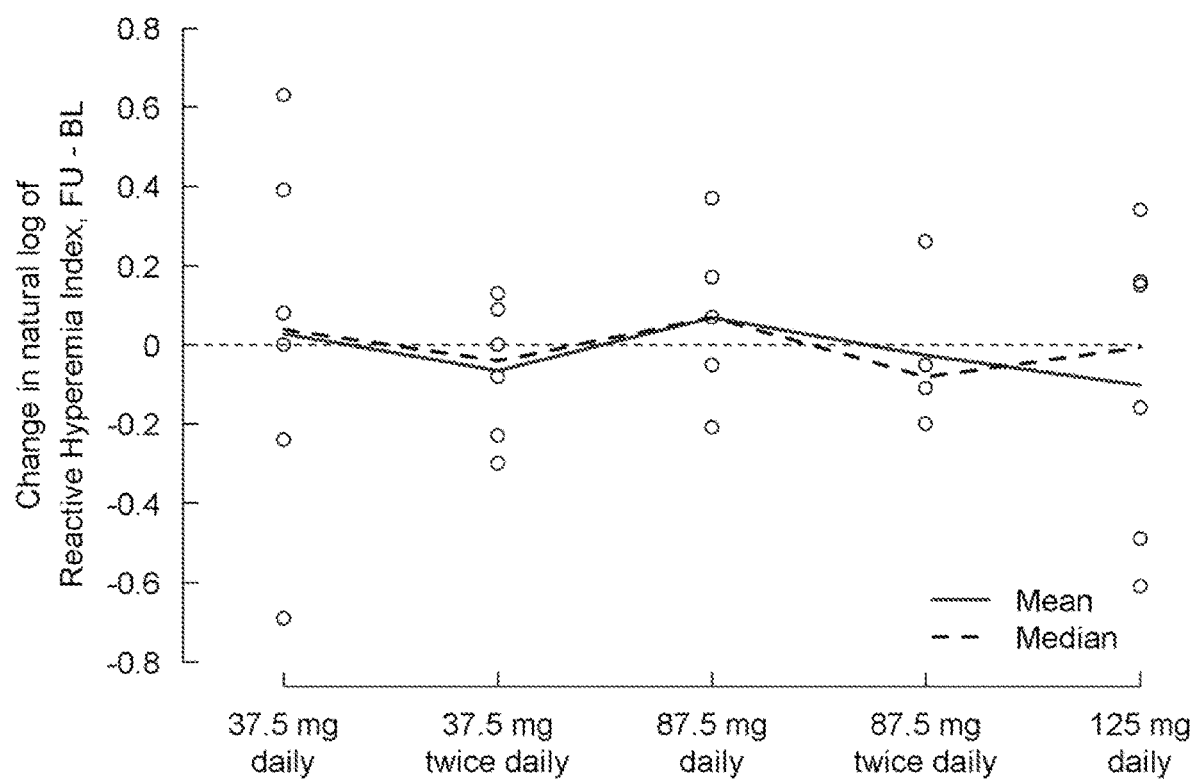
FIG. 6 shows change in natural log of Reactive Hyperemia Index from baseline (day 1) to the last visit (post-medication, day 5) by treatment group. A positive change indicates an improvement.
Figure 7:
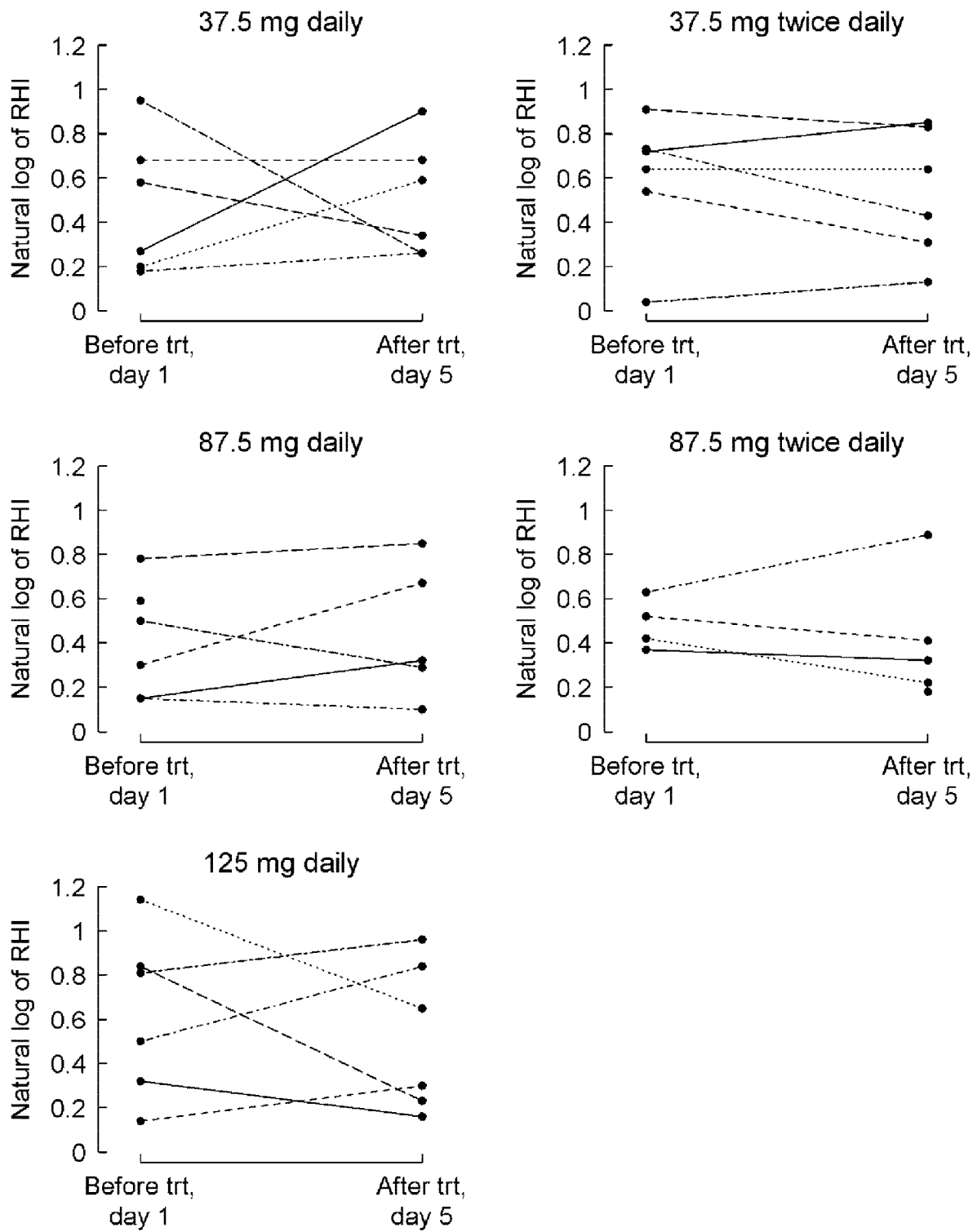
FIG. 7 shows natural log of Reactive Hyperemia Index (RHI) at baseline (day 1) and at the last visit (post-medication, day 5) by treatment group. A positive change indicates an improvement.

FIGS. 6 and 7 present the findings for change scores in a visual way (with a positive change indicating an improvement). FIG. 6 displays the individual change score for each subject with paired measurements (circles) and two lines with mean and median values. The plots do not suggest that change scores increase with the dose. FIG. 7 displays lnRHI values before and after the treatment for each subject and in each cohort.

Baseline and follow-up measurements are moderately correlated, with an overall correlation coefficient of 0.4.

Of note, both mean baseline and follow-up measurements are close to the cut-off value of 0.51 suggested by the EndoPAT documentation as a threshold between the normal (defined as lnRHI>0.51) and abnormal (lnRHI≤0.51) values. Analysis of the data indicates that some patients showed as much as a 9.75% improvement in this measure.

Table 17 reports change scores only for secondary EndoPAT outcomes (RHI, Framingham RHI etc; top panel) and other EndoPAT indices. In all cases a positive change suggests a possible improvement.

TABLE 17

Secondary and Other EndoPAT Outcomes, FU − BL

| | N | All subjects | N | 37.5 mg daily | N | 37.5 mg twice daily | N | 87.5 mg daily | N | 87.5 mg twice daily | N | 125 mg daily | P-value |
|---|---|---|---|---|---|---|---|---|---|---|---|---|---|
| Secondary EndoPAT outcomes | | | | | | | | | | | | | |
| Reactive Hyperemia Index | 27 | −0.04 ± 0.56 | 6 | 0.03 ± 0.84 | 6 | −0.12 ± 0.30 | 5 | 0.12 ± 0.34 | 4 | 0.01 ± 0.38 | 6 | −0.21 ± 0.78 | 0.895 |
| Framingham RHI | 27 | −0.06 ± 0.39 | 6 | −0.00 ± 0.58 | 6 | −0.17 ± 0.19 | 5 | 0.04 ± 0.36 | 4 | 0.00 ± 0.20 | 6 | −0.13 ± 0.51 | 0.901 |
| AUC2max_oc: Area under the curve to Max-Occlusion/Control | 27 | 0.51 ± 2.91 | 6 | −0.93 ± 4.37 | 6 | −1.19 ± 1.84 | 5 | 3.03 ± 2.49 | 4 | 0.16 ± 1.08 | 6 | 1.80 ± 1.18 | 0.058 |
| Avg2Max_oc: average up to max-Occlusion/Control | 27 | −0.16 ± 0.79 | 6 | −0.35 ± 1.01 | 6 | −0.33 ± 0.26 | 5 | 0.17 ± 0.43 | 4 | 0.24 ± 0.23 | 6 | −0.32 ± 1.28 | 0.626 |

TABLE 17-continued

Secondary and Other EndoPAT Outcomes, FU − BL

| | N | All subjects | N | 37.5 mg daily | N | 37.5 mg twice daily | N | 87.5 mg daily | N | 87.5 mg twice daily | N | 125 mg daily | P-value |
|---|---|---|---|---|---|---|---|---|---|---|---|---|---|
| | | | | | | Other EndoPAT indices | | | | | | | |
| AUC2max_o: Area under the curve to Max-Occlusion (ratio to baseline) | 27 | −0.26 ± 2.75 | 6 | −0.23 ± 2.74 | 6 | 0.09 ± 1.45 | 5 | −1.26 ± 4.89 | 4 | −0.51 ± 1.64 | 6 | 0.37 ± 2.71 | 0.910 |
| AUCall_o: Area under the curve all-Occlusion (ratio to baseline) | 27 | 0.18 ± 3.54 | 6 | −0.01 ± 2.73 | 6 | −0.69 ± 2.17 | 5 | 1.66 ± 5.96 | 4 | 0.60 ± 2.95 | 6 | −0.28 ± 3.98 | 0.864 |
| AUCall_oc: Area under the curve all-Occlusion/Control | 27 | −0.60 ± 4.93 | 6 | −1.34 ± 6.42 | 6 | −1.19 ± 2.00 | 5 | 1.88 ± 3.25 | 4 | 0.17 ± 4.30 | 6 | −1.84 ± 7.21 | 0.772 |
| Avg2Max_o: average upto max-Occlusion** | 27 | 0.04 ± 0.51 | 6 | −0.12 ± 0.28 | 6 | 0.15 ± 0.19 | 5 | 0.10 ± 0.69 | 4 | 0.03 ± 0.36 | 6 | 0.07 ± 0.86 | 0.930 |
| Avgall_o: average all-Occlusion** | 27 | 0.02 ± 0.40 | 6 | 0.02 ± 0.27 | 6 | −0.08 ± 0.24 | 5 | 0.14 ± 0.67 | 4 | 0.09 ± 0.33 | 6 | −0.03 ± 0.49 | 0.927 |
| Avgall_oc: average all - Occlusion/Control | 27 | −0.06 ± 0.54 | 6 | −0.10 ± 0.66 | 6 | −0.13 ± 0.22 | 5 | 0.16 ± 0.36 | 4 | 0.05 ± 0.45 | 6 | −0.20 ± 0.84 | 0.848 |

P-values were calculated by ANOVA.
**ratio to baseline

Example 5

Echocardiographic Assessment of Ventricular Performance

The primary outcome of ventricular performance with assessed using echocardiographic methods and measured according to a myocardial performance Index (MPI). The MPI is a ventricular geometry-independent measure of combined systolic and diastolic ventricular performance (Charles S. Kleinman et al, 2008—Health and Fitness). It is obtained by indexing the sum of isovolumetric contraction and relaxation time to ejection time.

Table 18 summarizes results for the key outcome from the Echocardiographic Assessment of Ventricular Performance—Blood Pool MPI. Out of the 30 subjects enrolled in the treatment arms of the trial, 27 subjects had paired measurements. The structure of the table is similar to the one for exercise variables. Analysis of the data indicates that some patients showed as much as a 21.5% improvement in this measure.

TABLE 18

Blood Pool MPI

| | N | All subjects | N | 37.5 mg daily | N | 37.5 mg twice daily | N |
|---|---|---|---|---|---|---|---|
| Baseline measurement | 29 | 0.581 ± 0.197 | 6 | 0.537 ± 0.304 | 6 | 0.496 ± 0.150 | 6 |
| Follow-up measurement | 28 | 0.517 ± 0.165 | 5 | 0.504 ± 0.187 | 6 | 0.494 ± 0.087 | 6 |
| Difference, FU − BL | 27 | −0.059 ± 0.134 | 5 | −0.052 ± 0.166 | 6 | −0.003 ± 0.102 | 6 |

| | 87.5 mg daily | N | 87.5 mg twice daily | N | 125 mg daily | P-value |
|---|---|---|---|---|---|---|
| Baseline measurement | 0.588 ± 0.158 | 5 | 0.548 ± 0.136 | 6 | 0.728 ± 0.155 | 0.305 |
| Follow-up measurement | 0.512 ± 0.163 | 6 | 0.410 ± 0.078 | 5 | 0.696 ± 0.202 | 0.058 |
| Difference, FU − BL | −0.076 ± 0.144 | 5 | −0.118 ± 0.090 | 5 | −0.054 ± 0.180 | 0.744 |

Figure 8:
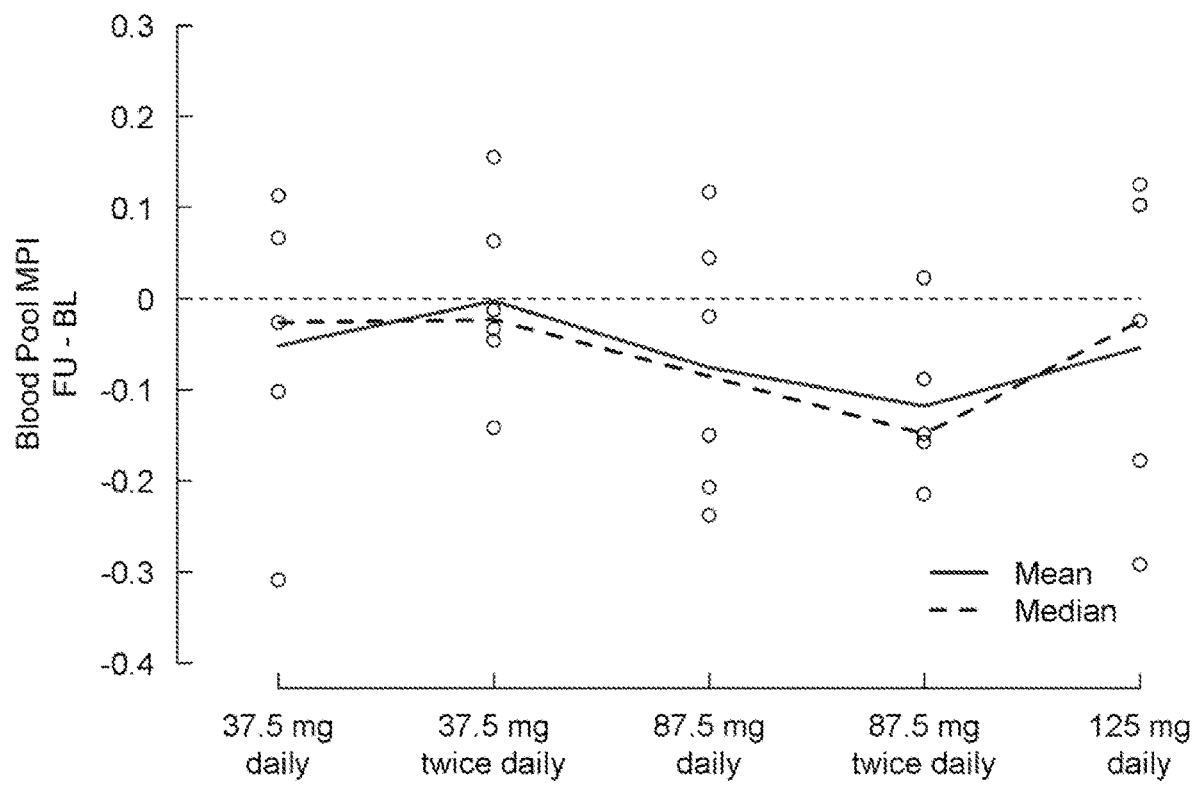
FIG. 8 shows change in blood pool MPI from baseline (day 1) to the last visit (post-medication, day 5) by treatment group. A negative change indicates an improvement.
Figure 9:
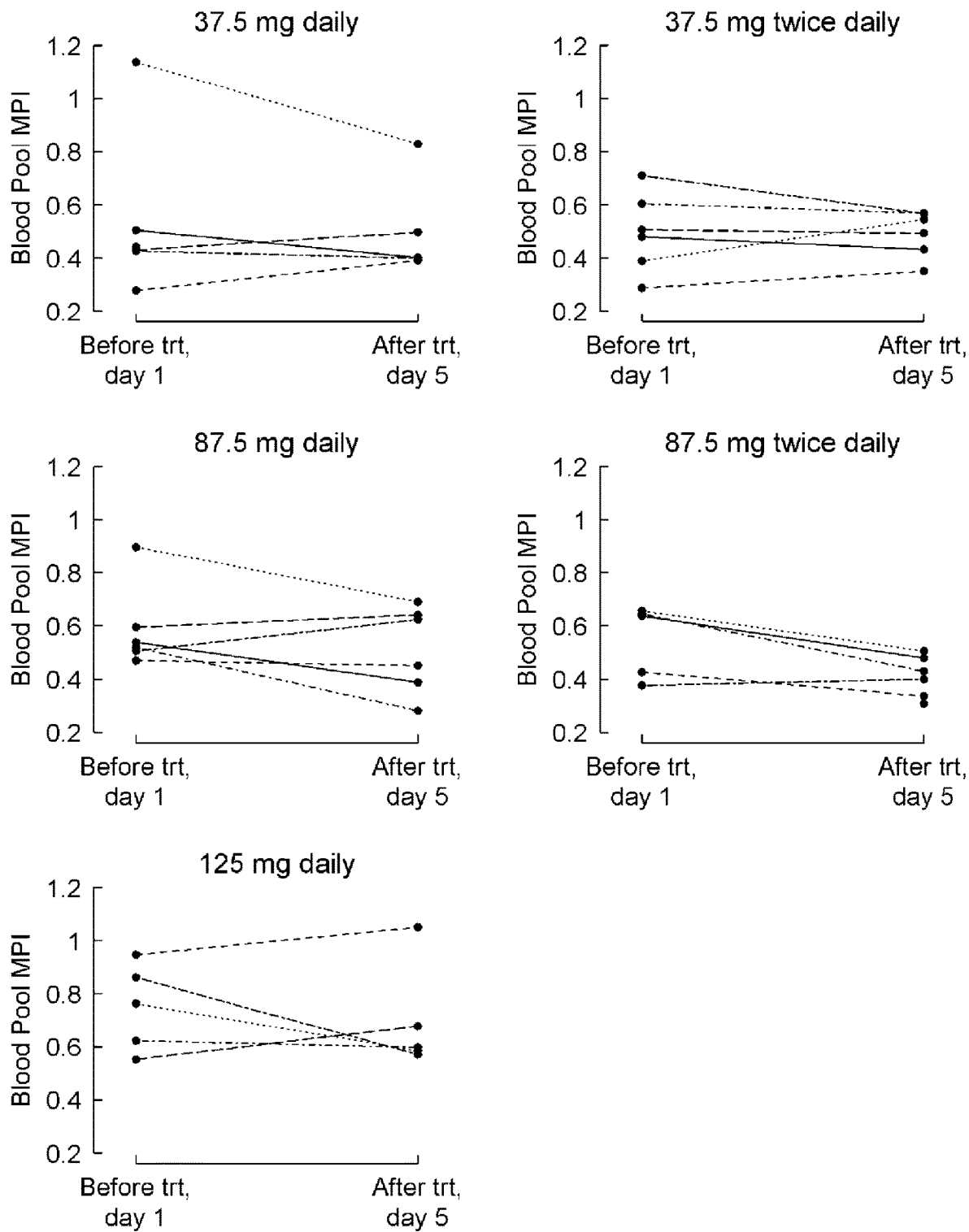
FIG. 9 shows blood pool MPI at baseline (day 1) and at the last visit (post-medication, day 5) by treatment group. A negative change indicates an improvement.
Figure 10:
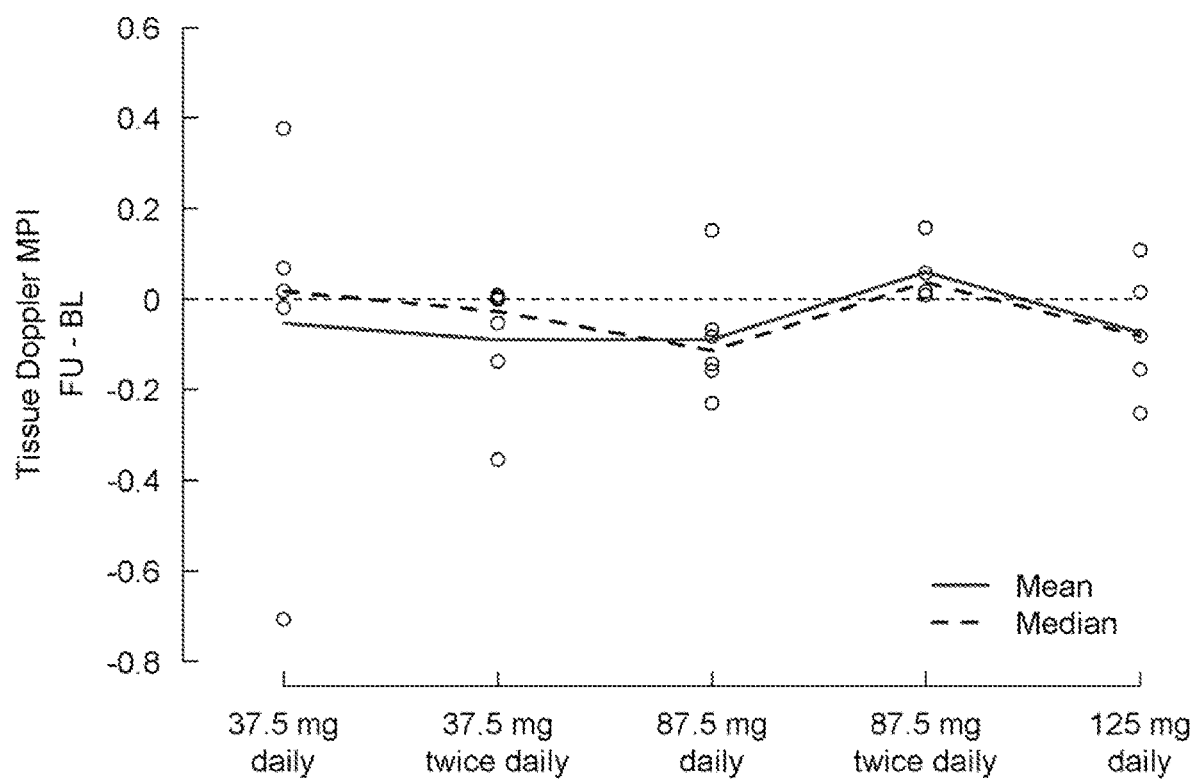
FIG. 10 shows change in tissue Doppler MPI from baseline (day 1) to the last visit (post-medication, day 5) by treatment group. A negative change indicates an improvement.
Figure 11:
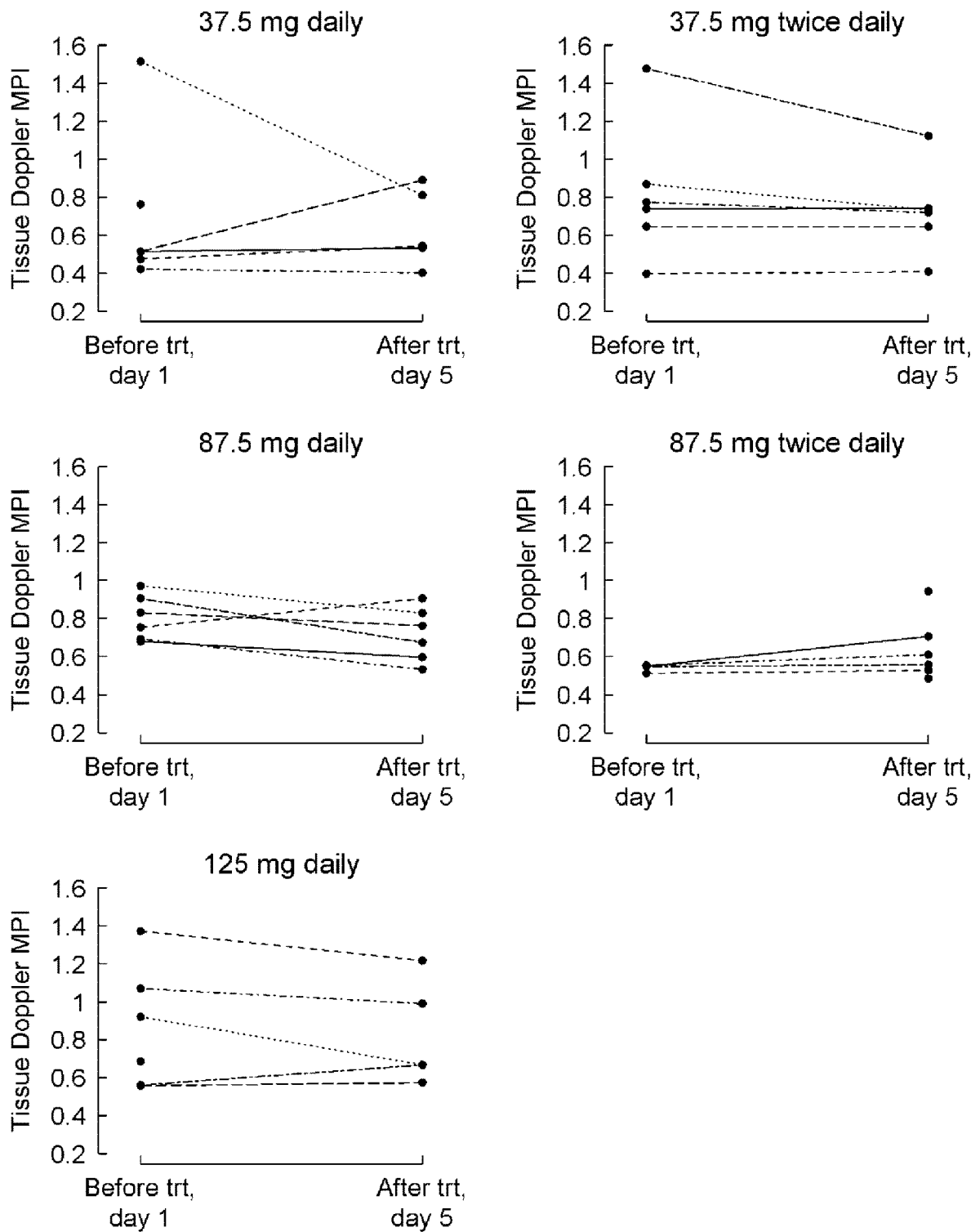
FIG. 11 shows tissue Doppler MPI at baseline (day 1) and at the last visit (post-medication, day 5) by treatment group. A negative change indicates an improvement.
Figure 12:
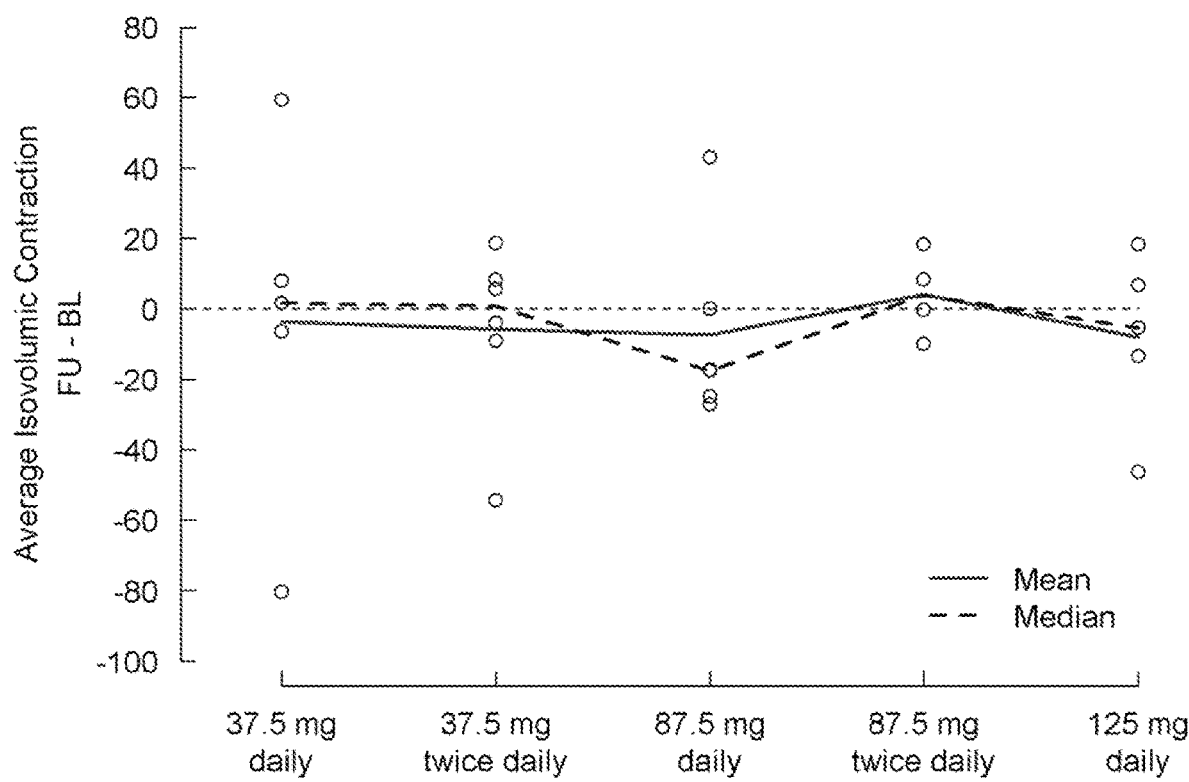
FIG. 12 shows change in average isovolumic contraction from baseline (day 1) to the last visit (post-medication, day 5) by treatment group. A negative change indicates an improvement.
Figure 13:
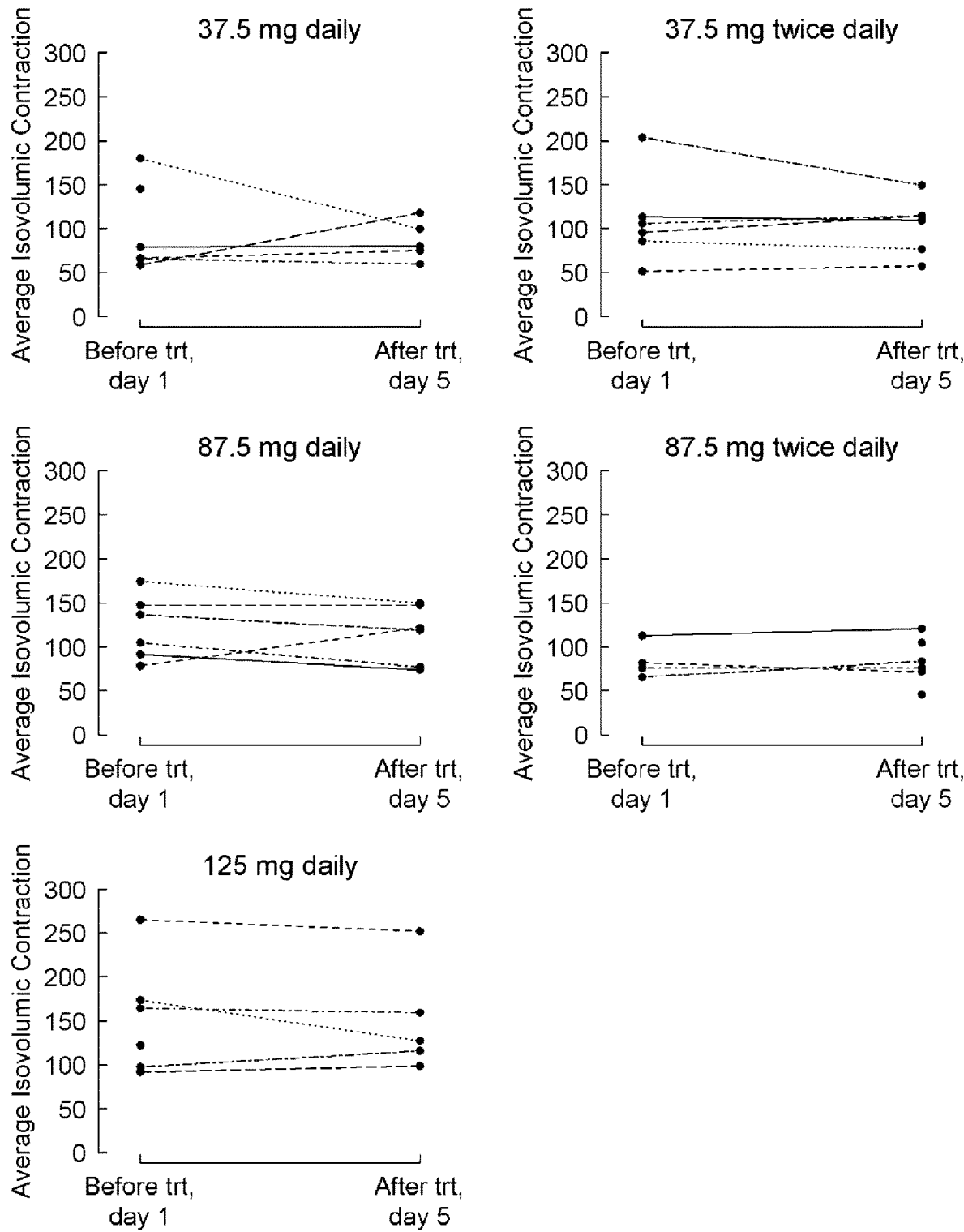
FIG. 13 shows average isovolumic contraction at baseline (day 1) and at the last visit (post-medication, day 5) by treatment group. A negative change indicates an improvement.
Figure 14:
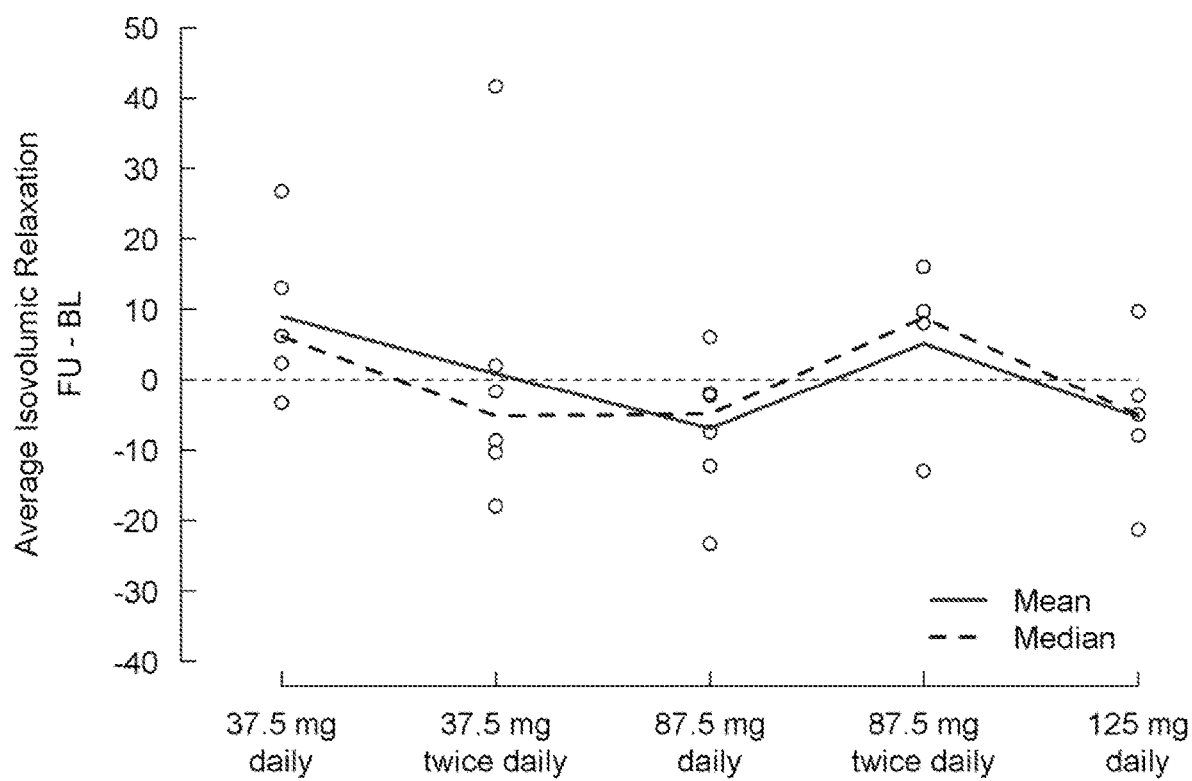
FIG. 14 shows change in average isovolumic relaxation from baseline (day 1) to the last visit (post-medication, day 5) by treatment group. A negative change indicates an improvement.
Figure 15:
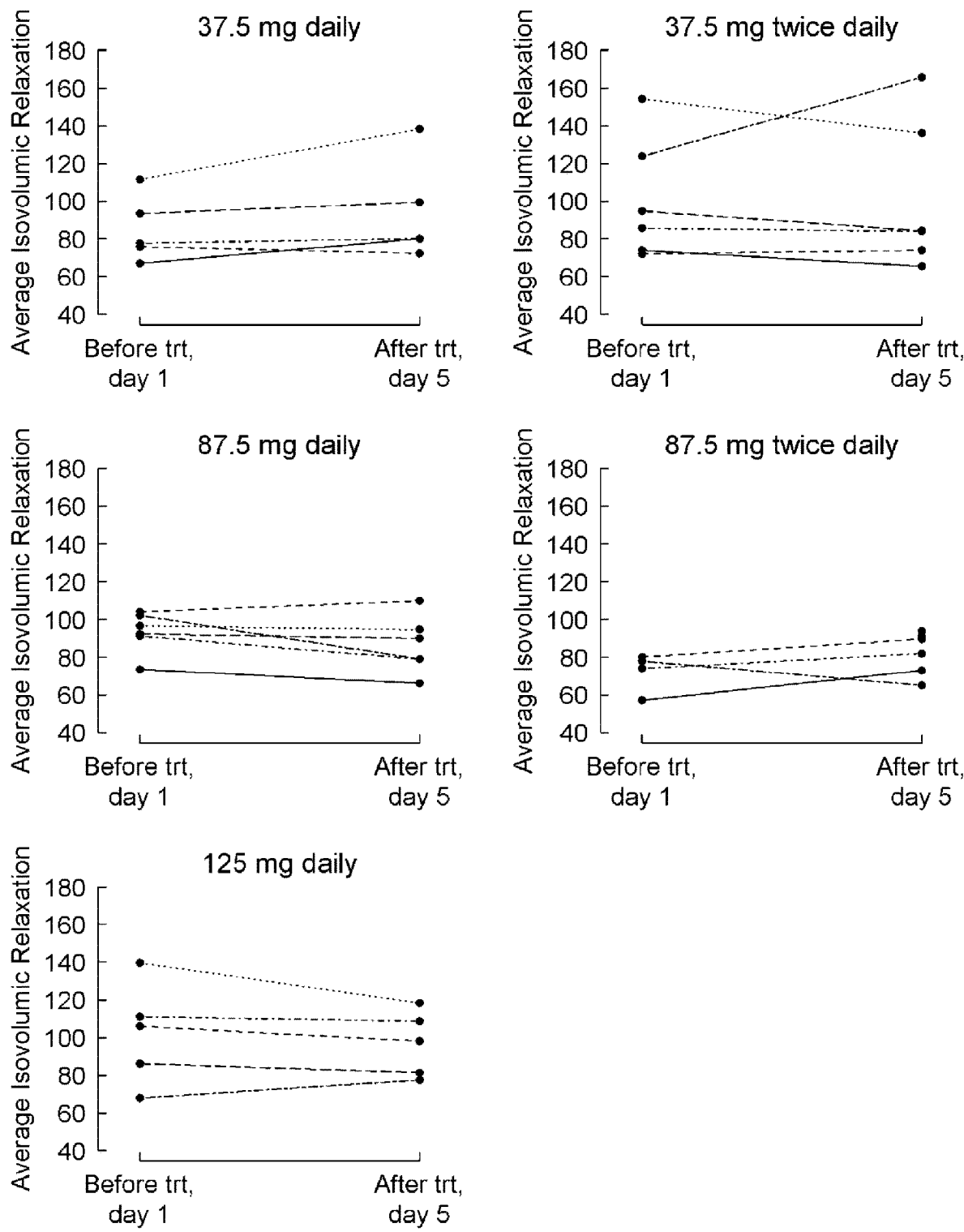
FIG. 15 shows average isovolumic relaxation at baseline (day 1) and at the last visit (post-medication, day 5) by treatment group. A negative change indicates an improvement.

FIGS. 8 and 9 present the findings for change scores in a visual way (with a negative change indicating an improvement). FIG. 8 displays individual change score for each subject with paired measurements (circles) and two lines with mean and median values. The plots don't suggest that change scores increase with the dose. FIG. 9 displays blood pool MPI index values before and after the treatment for each subject and in each cohort.

Baseline and follow-up measurements are strongly correlated, with the overall correlation coefficient of 0.7 (last 2 lines). Of note, both mean baseline and follow-up measurements are in the elevated area (>0.4).

Tables 19-21 and FIGS. 9-15 report similar results for three other versions of MPI: Tissue Doppler MPI, and Average Isovolumetric Contraction and Relaxation.

Additionally, because positive outcomes were seen during the short duration of the studies described in Examples 1-5, administering udenafil or a pharmaceutically acceptable salt thereof to a Fontan patient for a longer period of time could produce even more beneficial pharmacodynamic outcomes.

Example 6

Pharmacokinetic Testing

NONMEM version 7.2, R, PDxPOP® 5, Xpose, and Phoenix WinNonlin was used for the pharmacokinetic analysis.

Figure 16:
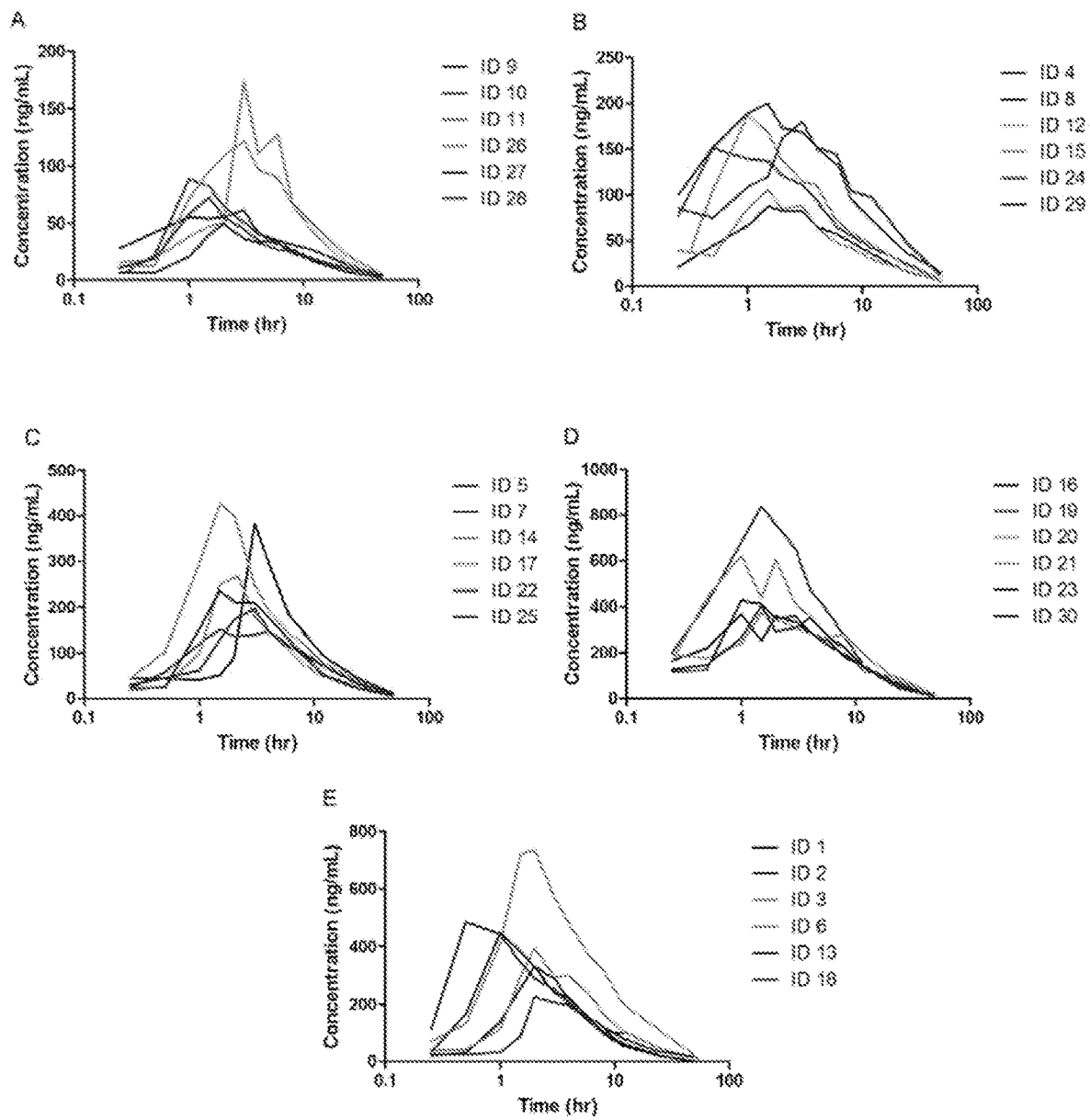
FIG. 16 shows individual concentration time curves stratified by dosing regimens of (A) 37.5 mg q24 h, (B) 37.5 mg q12 h, (C) 87.5 mg q24 h, (D) 87.5 mg q12 h, and (E) 125 mg q24 h.

Pharmacokinetic analysis was performed on Fontan patients receiving udenafil. FIG. 16 show the results of data

TABLE 19

Tissue Doppler MPI

|  | N | All subjects | N | 37.5 mg daily | N | 37.5 mg twice daily | N |
|---|---|---|---|---|---|---|---|
| Baseline measurement | 28 | 0.760 ± 0.299 | 6 | 0.701 ± 0.417 | 6 | 0.818 ± 0.361 | 6 |
| Follow-up measurement | 28 | 0.707 ± 0.201 | 5 | 0.637 ± 0.206 | 6 | 0.729 ± 0.230 | 6 |
| Difference, FU − BL | 26 | −0.056 ± 0.198 | 5 | −0.052 ± 0.398 | 6 | −0.089 ± 0.142 | 6 |

|  | 87.5 mg daily | N | 87.5 mg twice daily | N | 125 mg daily | P-value |
|---|---|---|---|---|---|---|
| Baseline measurement | 0.804 ± 0.118 | 4 | 0.540 ± 0.019 | 6 | 0.861 ± 0.323 | 0.517 |
| Follow-up measurement | 0.716 ± 0.142 | 6 | 0.638 ± 0.168 | 5 | 0.822 ± 0.271 | 0.579 |
| Difference, FU − BL | −0.089 ± 0.131 | 4 | 0.060 ± 0.068 | 5 | −0.074 ± 0.141 | 0.813 |

TABLE 20

Average Isovolumic Contraction

|  | N | All subjects | N | 37.5 mg daily | N | 37.5 mg twice daily | N | 87.5 mg daily | N | 87.5 mg twice daily | N | 125 mg daily | P-value |
|---|---|---|---|---|---|---|---|---|---|---|---|---|---|
| Baseline measurement | 28 | 115.6 ± 50.5 | 6 | 99.2 ± 50.7 | 6 | 109.4 ± 51.1 | 6 | 122.4 ± 36.7 | 4 | 84.1 ± 20.3 | 6 | 152.4 ± 64.4 | 0.236 |
| Follow-up measurement | 28 | 107.1 ± 41.3 | 5 | 86.4 ± 22.7 | 6 | 103.6 ± 32.4 | 6 | 115.0 ± 32.9 | 6 | 83.8 ± 26.4 | 5 | 150.5 ± 60.5 | 0.047 |
| Difference, FU − BL | 26 | −4.6 ± 28.3 | 5 | −3.5 ± 50.0 | 6 | −5.8 ± 25.7 | 6 | −7.4 ± 26.5 | 4 | 4.1 ± 12.1 | 5 | −8.0 ± 24.6 | 0.977 |

TABLE 21

Average Isovolumetric Relaxation

|  | N | All subjects | N | 37.5 mg daily | N | 37.5 mg twice daily | N | 87.5 mg daily | N | 87.5 mg twice daily | N | 125 mg daily | P-value |
|---|---|---|---|---|---|---|---|---|---|---|---|---|---|
| Baseline measurement | 28 | 91.2 ± 22.2 | 6 | 83.8 ± 16.1 | 6 | 100.8 ± 32.3 | 6 | 93.4 ± 11.0 | 4 | 72.3 ± 10.5 | 6 | 99.5 ± 25.0 | 0.236 |
| Follow-up measurement | 28 | 92.0 ± 23.8 | 5 | 94.0 ± 26.7 | 6 | 101.6 ± 40.0 | 6 | 86.4 ± 15.3 | 6 | 82.4 ± 11.4 | 5 | 96.8 ± 17.4 | 0.674 |
| Difference, FU − BL | 26 | 0.1 ± 14.4 | 5 | 9.0 ± 11.5 | 6 | 0.8 ± 21.2 | 6 | −6.9 ± 10.1 | 4 | 5.2 ± 12.6 | 5 | −5.4 ± 11.1 | 0.354 |

Figure 17:
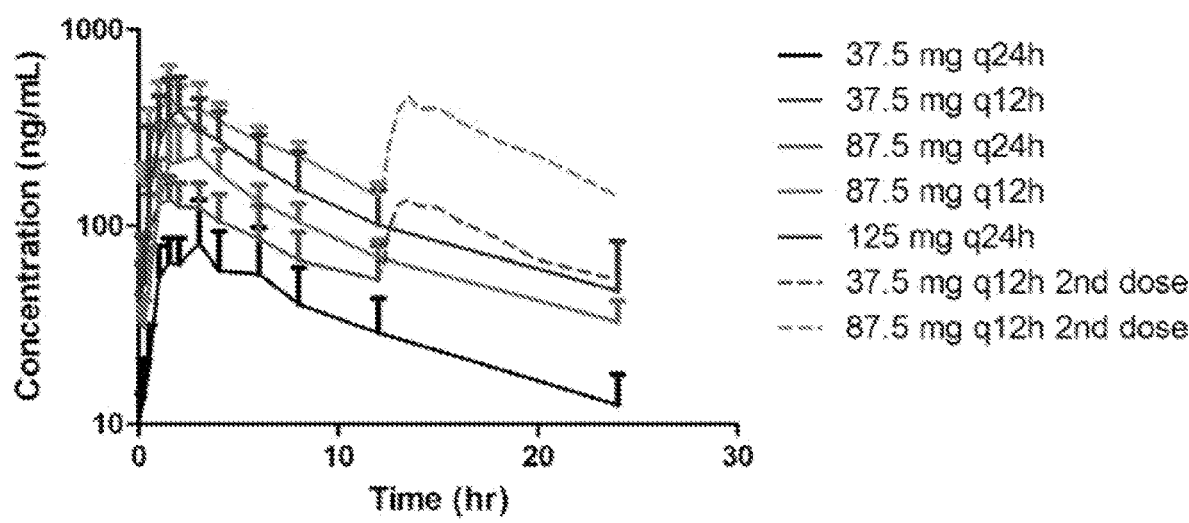
FIG. 17 shows concentration time concentration profiles of udenafil in study subjects. The solid line represents the observed data, the dash line stands for the predicted data for the second dose of the day for 12 hour regimens. Data are represented as mean+/−standard deviation.

For these three additional versions of MPI, a negative change also suggests a possible improvement and the overall conclusions are similar to those for Blood Pool MPI.

evaluation for individual subjects by dosing cohort, and FIG. 17 shows the concentration profiles of udenafil in the study subjects. Plasma concentrations were determined at various time points and non-compartmental analysis was performed in patients and stratified by dosing regimens.

Figure 18:
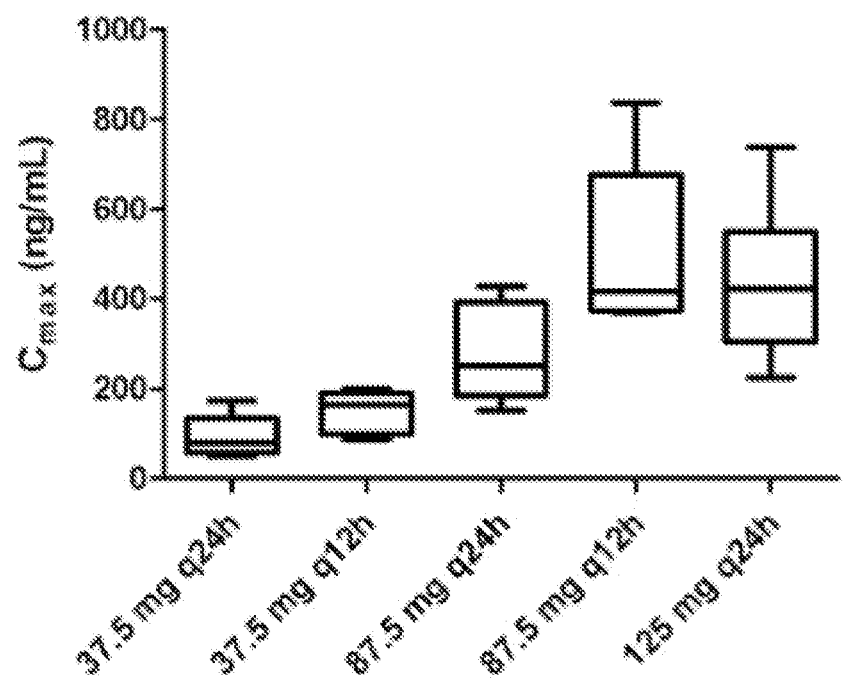
FIG. 18 shows a comparison of Cmax among various dosing regimens. The box and whisker plot showed 10-90 percentile and range of observations with middle line representing median value of a dosing regimen. Significant difference: 37.5 mg q24 h vs 87.5 mg q12 h, $p<0.001$; 37.5 mg q24 h vs 125 mg q24 h, $p<0.001$; 37.5 mg q12 h vs 87.5 mg q12 h, $p<0.001$; 37.5 mg q12 h vs 125 mg q24 h, $p<0.01$; 87.5 mg q24 h vs 87.5 mg q12 h, $p<0.05$.
Figure 19:
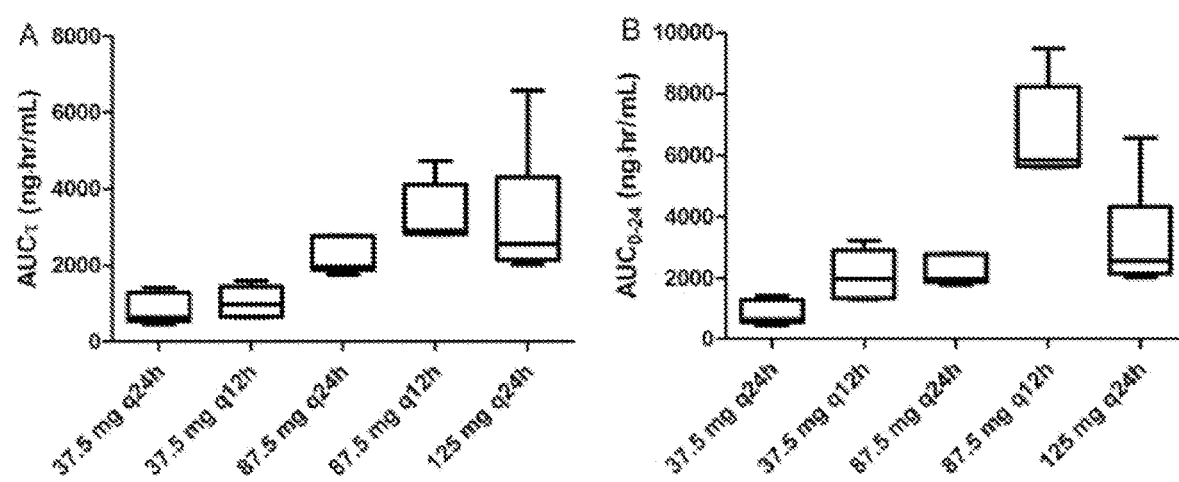
FIG. 19 shows a comparison of (A) AUCτ and (B) AUC0-24 among various dosing regimens. The box and whisker plot showed 10-90 percentile and range of observations with middle line representing median value of a dosing regimen. Significant difference: A) 37.5 mg q24 h vs 87.5 mg q12 h, $p<0.001$; 37.5 mg q24 h vs 125 mg q24 h, $p<0.001$; 37.5 mg q12 h vs 87.5 mg q12 h, $p<0.01$; 37.5 mg q12 h vs 125 mg q24 h, $p<0.01$; B) 37.5 mg q24 h vs 87.5 mg q12 h, $p<0.001$; 37.5 mg q24 h vs 125 mg q24 h, $p<0.01$; 37.5 mg q12 h vs 87.5 mg q12 h, $p<0.001$; 87.5 mg q24 h vs 87.5 mg q12 h, $p<0.001$; 87.5 mg q12 h vs 125 mg q24 h, $p<0.001$.
Figure 20:
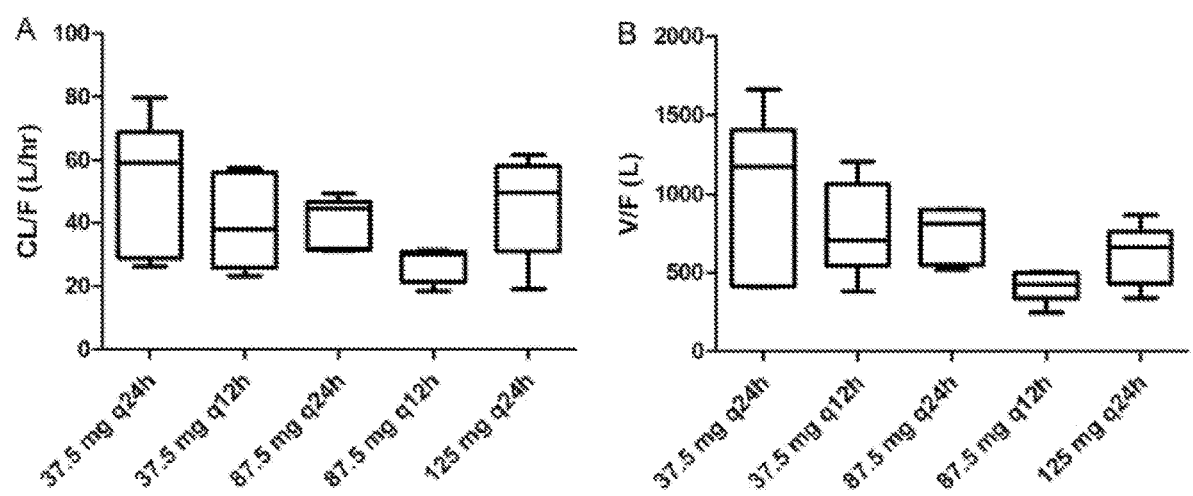
FIG. 20 shows a comparison of A) CL/F and B) V/F among various dosing regimens. The box and whisker plot showed 10-90 percentile and range of observations with middle line representing median value of a dosing regimen. Significant difference: A) 37.5 mg q24 h vs 87.5 mg q12 h, $p<0.05$; B) 37.5 mg q24 h vs 87.5 mg q12 h, $p<0.01$.
Figure 21:
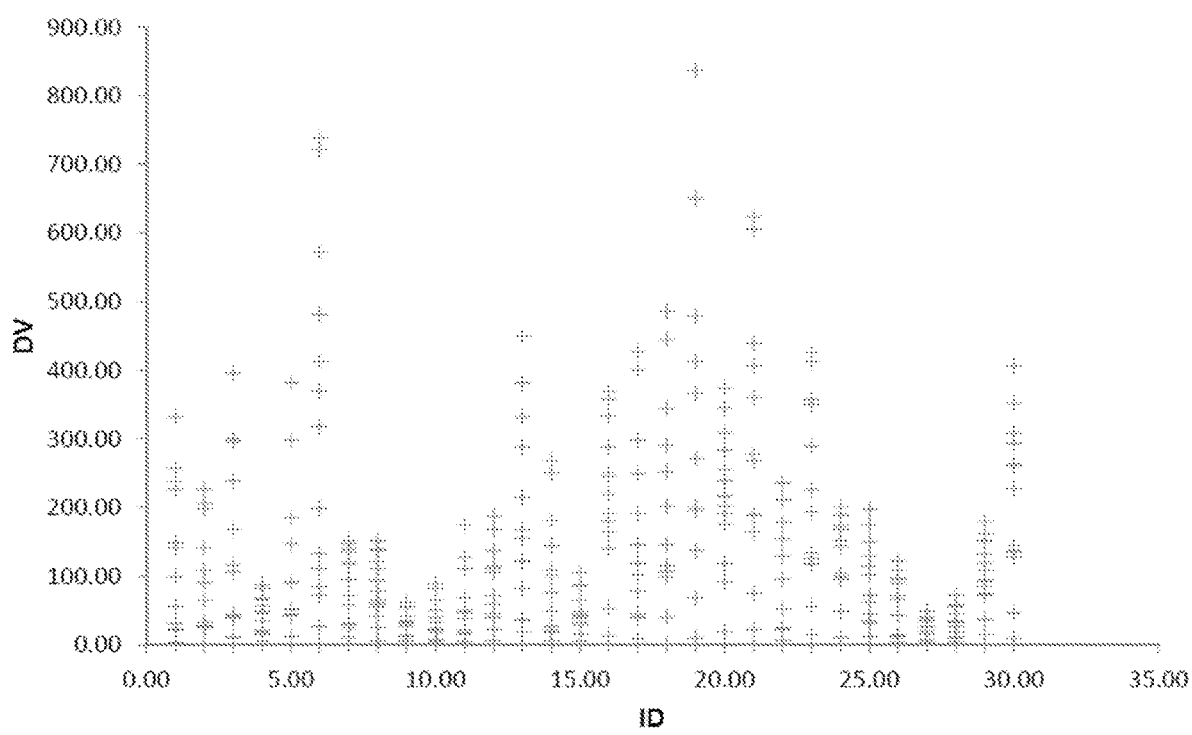
FIG. 21 shows DV (observed concentrations) versus subject ID.
Figure 22:
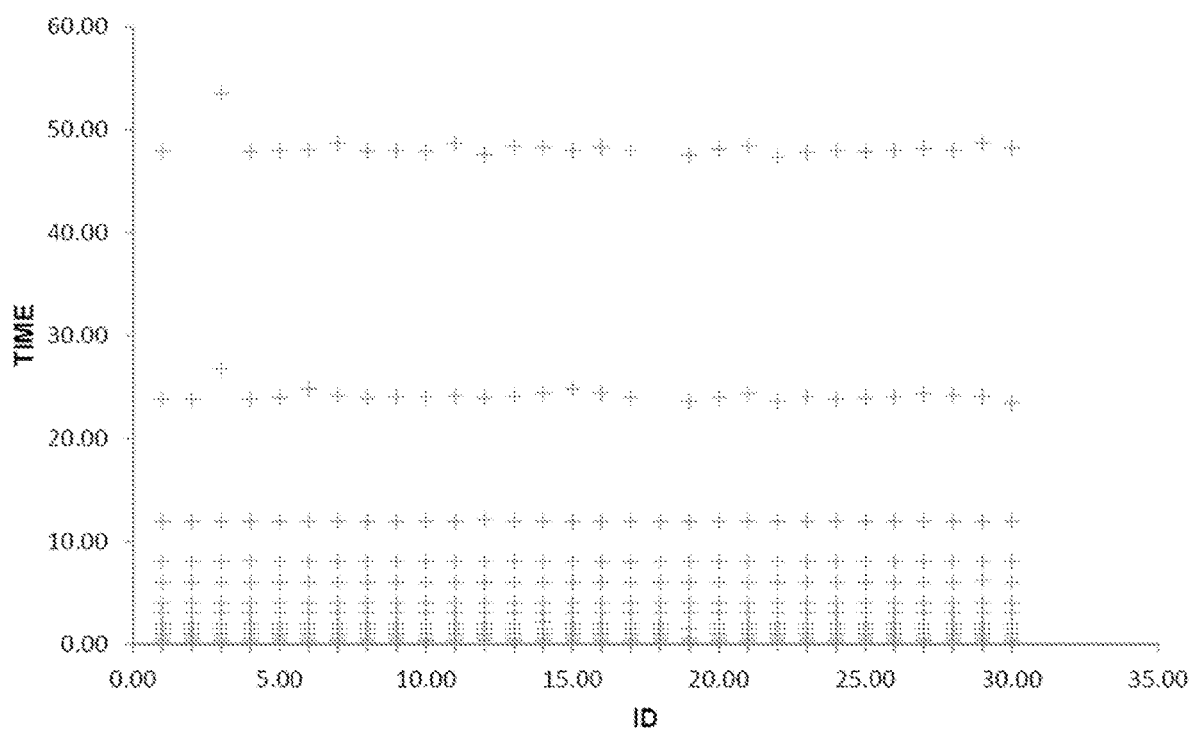
FIG. 22 shows time (hours) versus subject ID.
Figure 23:
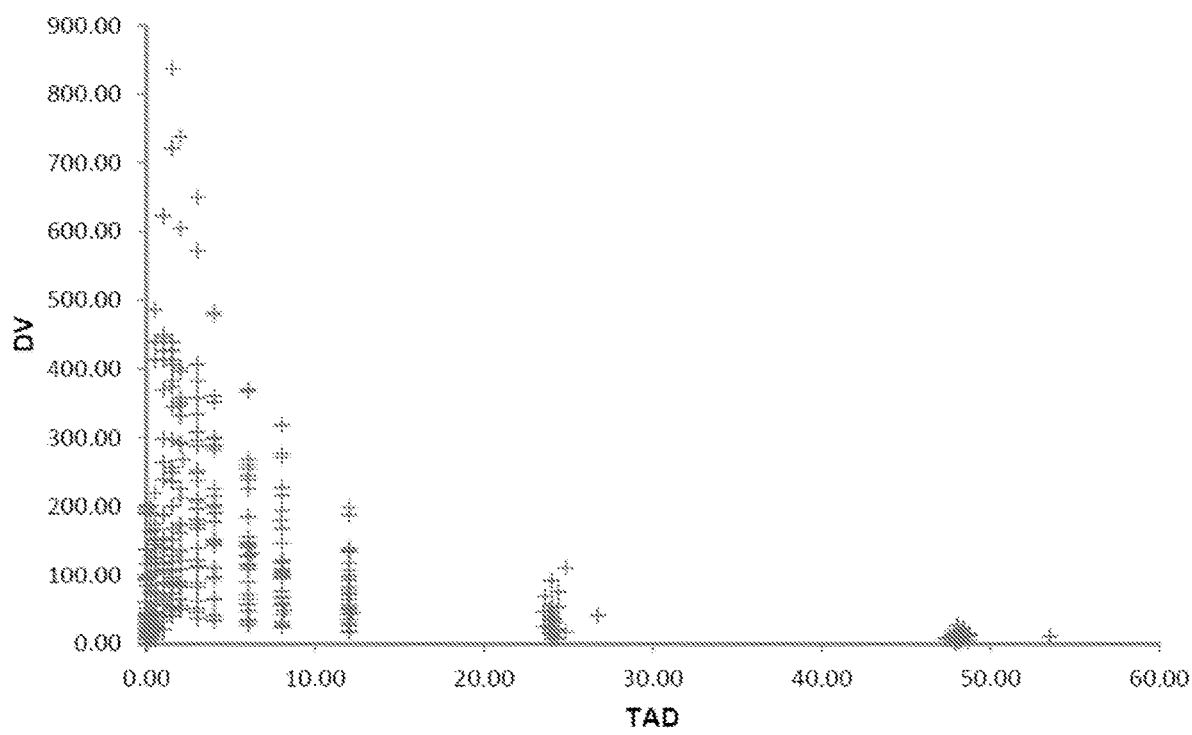
FIG. 23 shows DV (observed concentrations) versus time after dose (TAD).
Figure 24:
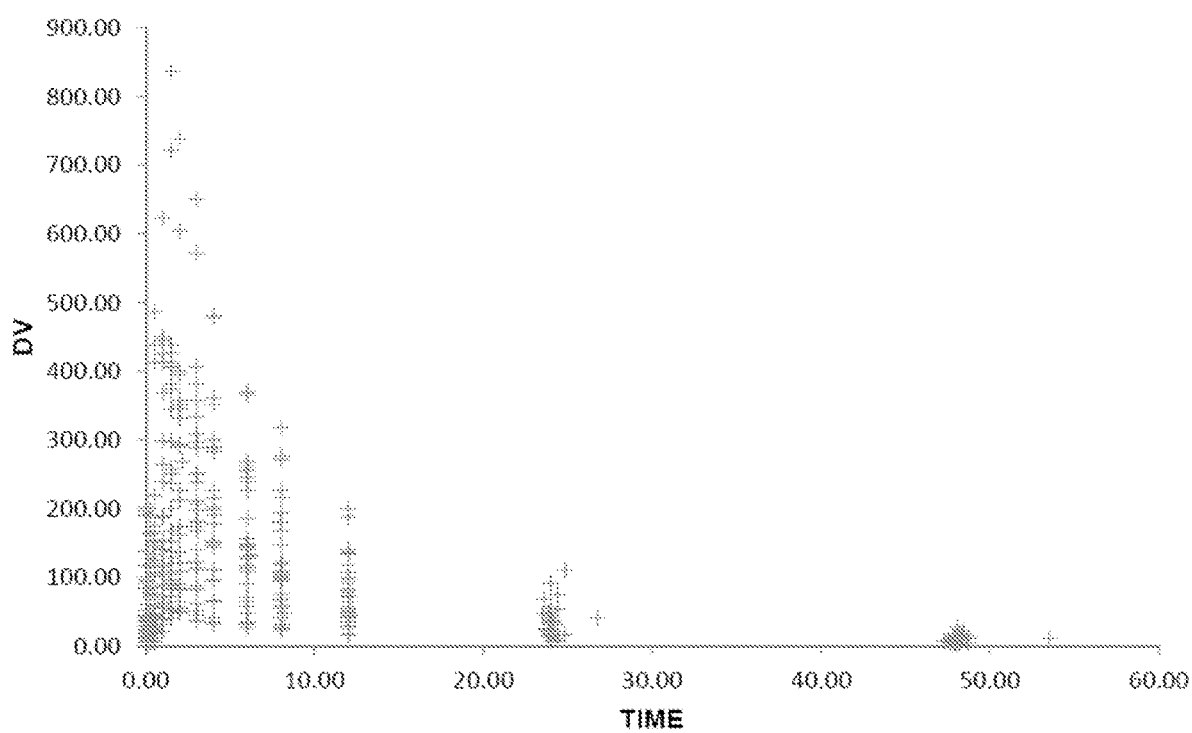
FIG. 24 shows DV (observed concentrations) versus time (hours).
Figure 25:
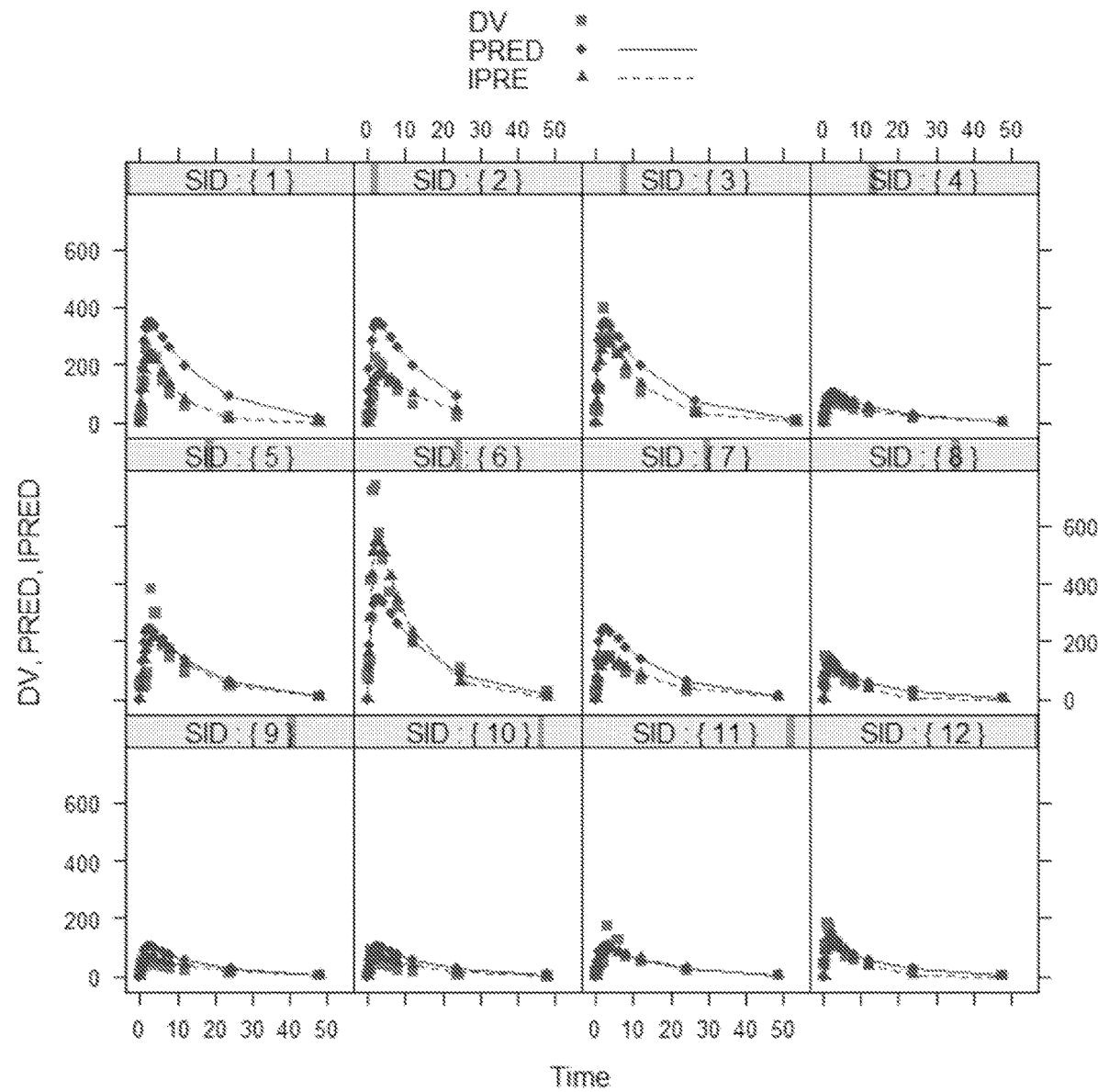
FIG. 25 shows individual visual plots (SID 1-12) with variation between observed concentration (DV) vs predicted concentration (PRED) and individual predicted (IPRED) error vs time (h).
Figure 26:
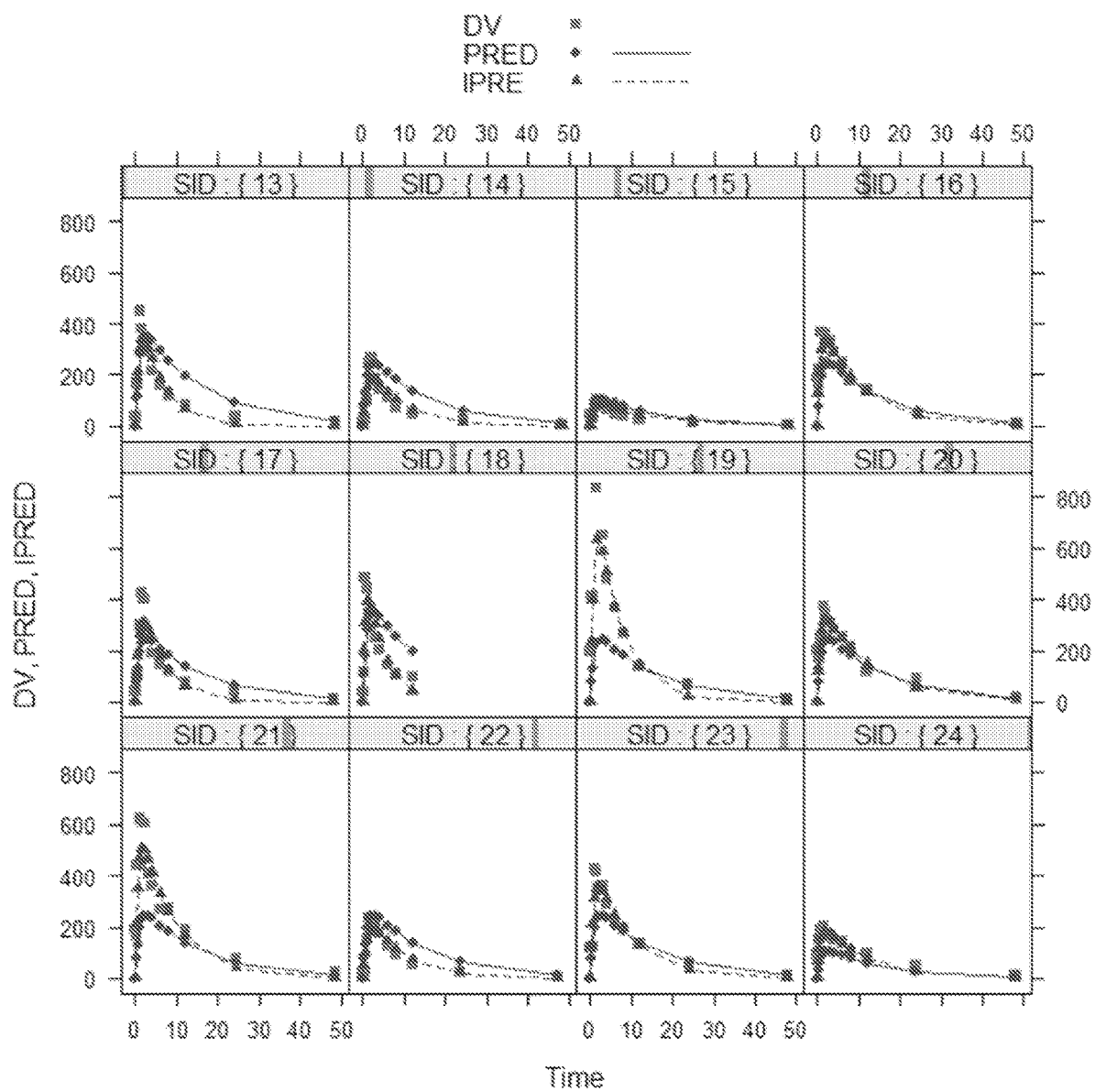
FIG. 26 shows individual visual plots (SID 13-24) with variation between observed concentration (DV) vs predicted concentration (PRED) and individual predicted (IPRED) error vs time (h).
Figure 27:
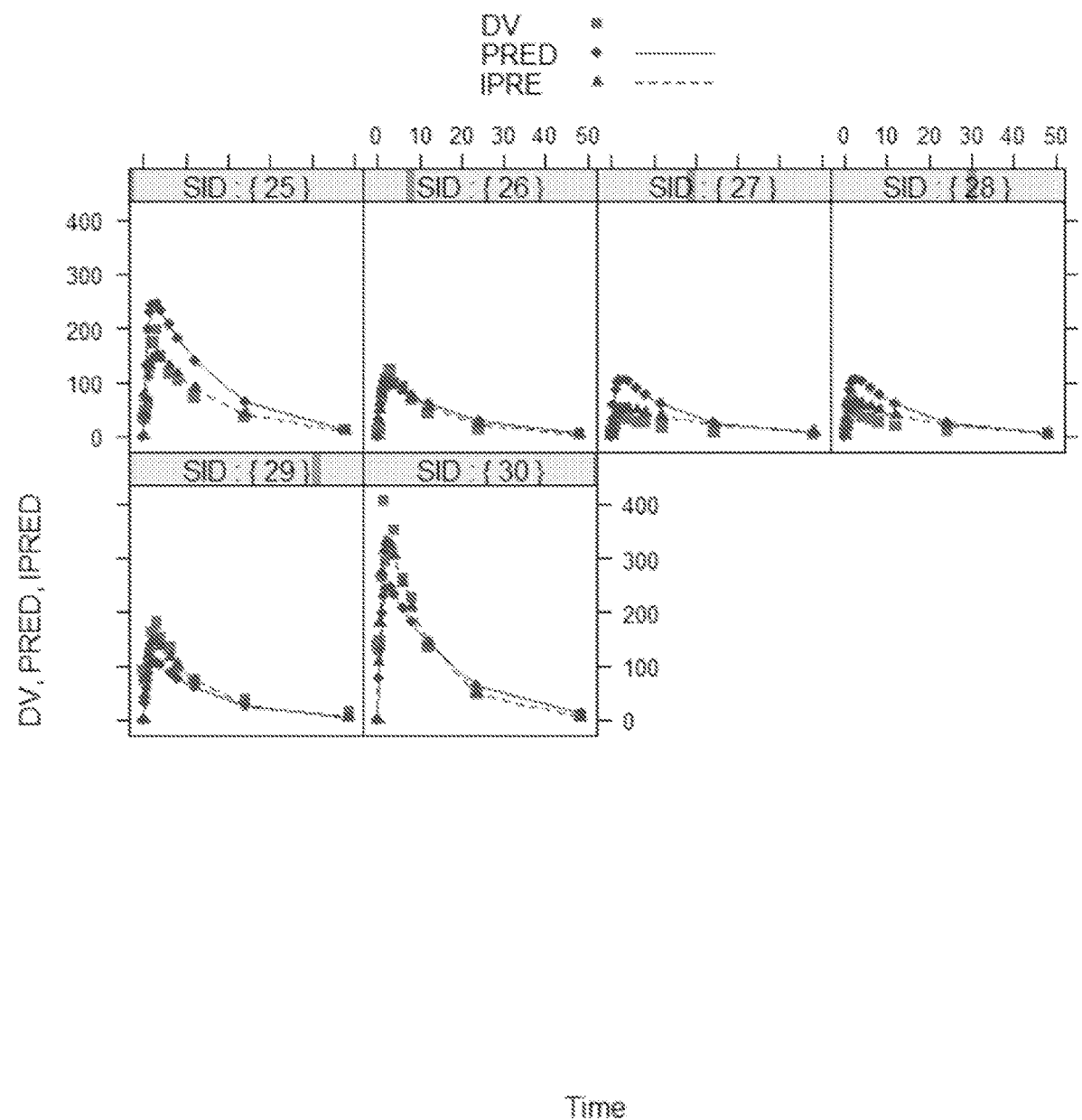
FIG. 27 shows individual visual plots (SID 25-30) with variation between observed concentration (DV) vs predicted concentration (PRED) and individual predicted (IPRED) error vs time (h).

FIGS. 18-20 demonstrate various comparisons among the dosing cohorts. Based on the non-compartment analysis, $C_{max}$ was significantly increased in 87.5 mg q12 h cohort and 125 mg q24 h cohort compared to the 37.5 mg q12 h or q24 h cohorts (FIG. 18).

The 87.5 mg q12 h cohort exhibited increased $C_{max}$ compared to its q24 h counterpart (FIG. 18). $AUC_\tau$ was significantly increased in 87.5 mg q12 h cohort and 125 mg q24 h cohort compared to the 37.5 mg q12 h or q24 h cohorts (FIG. 19). $AUC_{0-24}$ was significantly increased in 125 mg q24 h cohort compared to the 37.5 mg q24 h cohorts. The 87.5 mg q12 h cohort showed increased highest $AUC_{0-24}$ among all the regimens tested (FIG. 19). No significant difference was observed in CL/F or V/F among dosing regimens, expect the significant differences between 37.5 mg q24 h and 87.5 mg q12 h (FIG. 20). There was no statistically significant difference in $k_e$, $T_{1/2}$, or $T_{max}$ among all 5 tested dosing regimens.

Population PK Model Development

The population PK analysis was performed using a non-linear mixed effects modeling approach. This approach estimates the typical value of parameters and their variances. It was assumed subjects were at steady state (SS): at a time (t) after dose (D) given at time tD after repeated administration of dose D given at interval τ (t≥$t_D$) as PK samples/udenafil concentrations were taken on study day 6.

As only the drug administration at Day 6 was supplied, it is expected that the subjects have taken the drug at regular intervals at home; due to this a steady state flag will be tested to account for the doses which are not available. As stated, it is assumed steady state has been reached by Day 6, as previous studies of udenafil have stated that during multiple dosing, steady state is reached in 5 days, with apparently little additional accumulation occurring after dosing for 7 days. If there were missed doses during the study period prior to the PK sampling, this can affect the ability to determine whether steady state could be assumed or not for the PK profile. If two or more additional drug administration dates and times were available prior to the visit where the PK samples were taken, then a much better dosing profile could be used for analysis.

Structural Model

One- and two-compartment models were explored (based on literature and available data). The equation for the Input model for the drug described oral absorption. For the one-compartment model, the following equation may apply to the model:

$$\frac{dA}{dt} = \text{Input} - (k10 * A)$$

And considering that CL=k10*V, the following equation may also apply:

$$\frac{dC}{dt} = \frac{\text{Input} - (CL * C)}{V}$$

The two-compartment model can be described by the following differential equation:

$$\frac{dX1}{dt} = ka \cdot Xg + k21 \cdot X2 - (k12 + kel) \cdot X1$$

Drug Amount in the body after oral administration may be described by the following differential equation:

$$Cp = A \cdot e^{-\alpha \cdot t} + B \cdot e^{-\beta \cdot t} + C \cdot e^{-ka \cdot t}$$

The robustness of the final model was assessed in PDx-POP® 5 by bootstrap re-sampling (n=1000). Values obtained with the bootstrap (based on all runs with successful minimization) were compared to the parameter estimates from the final model. To evaluate the accuracy of the model predictions, normalized prediction distribution errors (NPDE) was performed.

Certain a priori information was used in guiding the development of the models.

One- and two-compartment models with oral absorption input were evaluated using initial estimates obtained from the literature as described above, and were explored to determine the potential structure of the model. The models were evaluated during the model building process by using objective function value, level of statistical significance, goodness of fit plots, and standard error.

The only covariate available for analysis was current body weight. Weight was tested as a fixed effect on typical values for clearance and volume of distribution (e.g., weight has a "fixed effect" on clearance). Median weight in the dataset was 65.3 kg.

The "typical value" for clearance is predicted per 70 kg patient using weight (WT) in the data set. The estimated THETA(1) and THETA(2) for subjects of known WT can be directly compared with CL and V values in subjects of "standard" weight, e.g. WTs=70 kg.

Concern is sometimes expressed that scaling parameter values estimated in children in terms of an adult size standard of 70 kg may bias the estimates, or affect the precision of estimation. There is no basis for this concern. This can be seen by inspection of the allometric scaled covariate model which may be re-arranged and is simply a constant that is determined by whatever weight is chosen for standardization. The precision of a parameter estimate will not be changed by multiplying the parameter value by an ad hoc constant. The criteria for covariate equation selection for weight in the model was statistical significance.

FIGS. 21-29 show the results of the pharmacokinetic data analysis.

Figure 30:
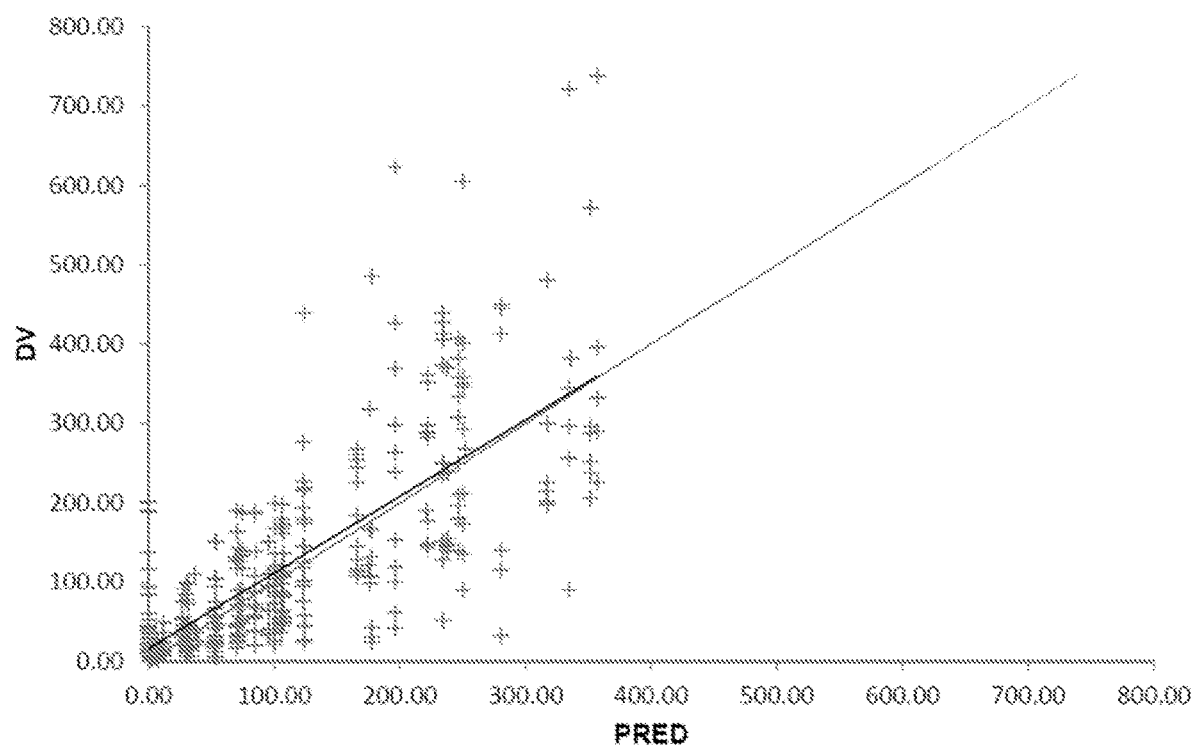
FIG. 30 shows a goodness of fit plot of observed data versus predicted data (DV vs. PRED).
Figure 31:
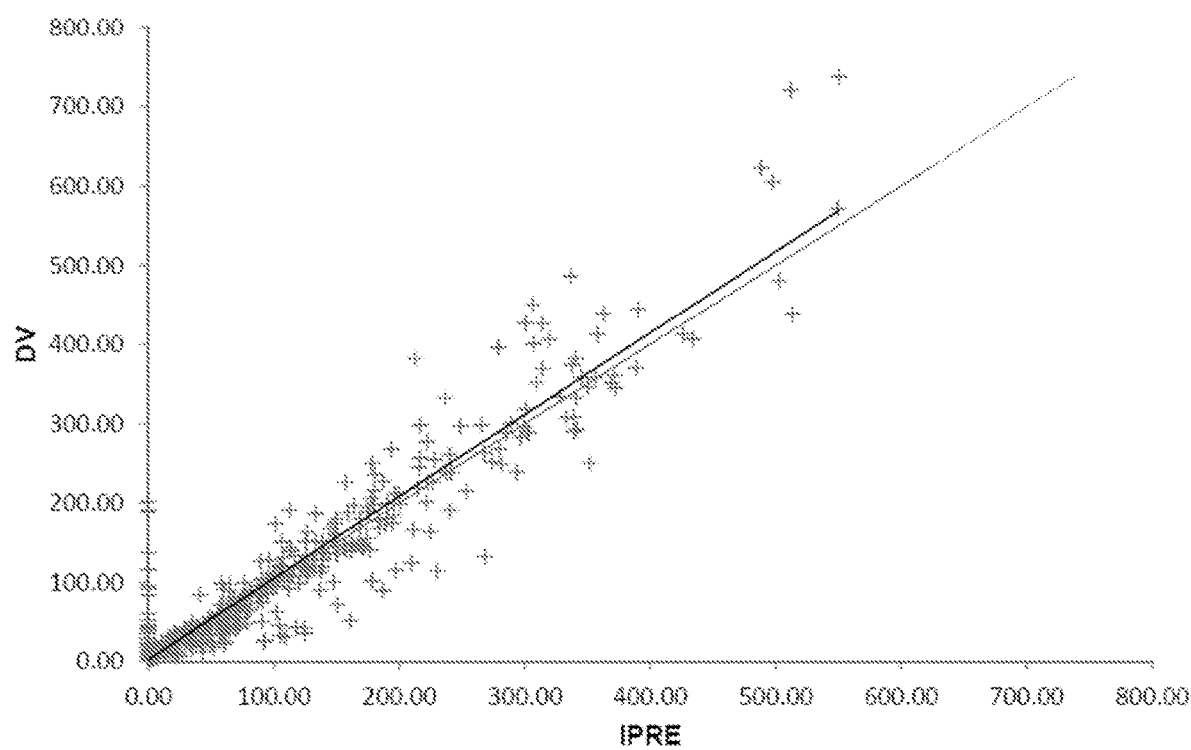
FIG. 31 shows a goodness of fit plot of observed data versus individual predicted data (DV vs. IPRED).

During the model building process, a number of residual error models were evaluated. Proportional and exponential error models were unable to run, these terminated every time. Additive error models were able to run, but the GOF plots showed a poor fit for one-compartment models with a better fit in the two compartment model. The choice was made to use a combined error model for the base model, despite the high CV % in the residual variability, as this model gave good estimates for other parameters, 95% CIs and showed a good fit on visual inspection of GOF plots (FIGS. 30-31). It may be possible to control for the high CV % if all of the doses from days 1-5 were included from each subject in the dataset before the day 6 dose, around which the sampling occurred. It is not be necessary to do this as the model fit is good as presently described, but this may further reduce the % CVs.

Figure 32:
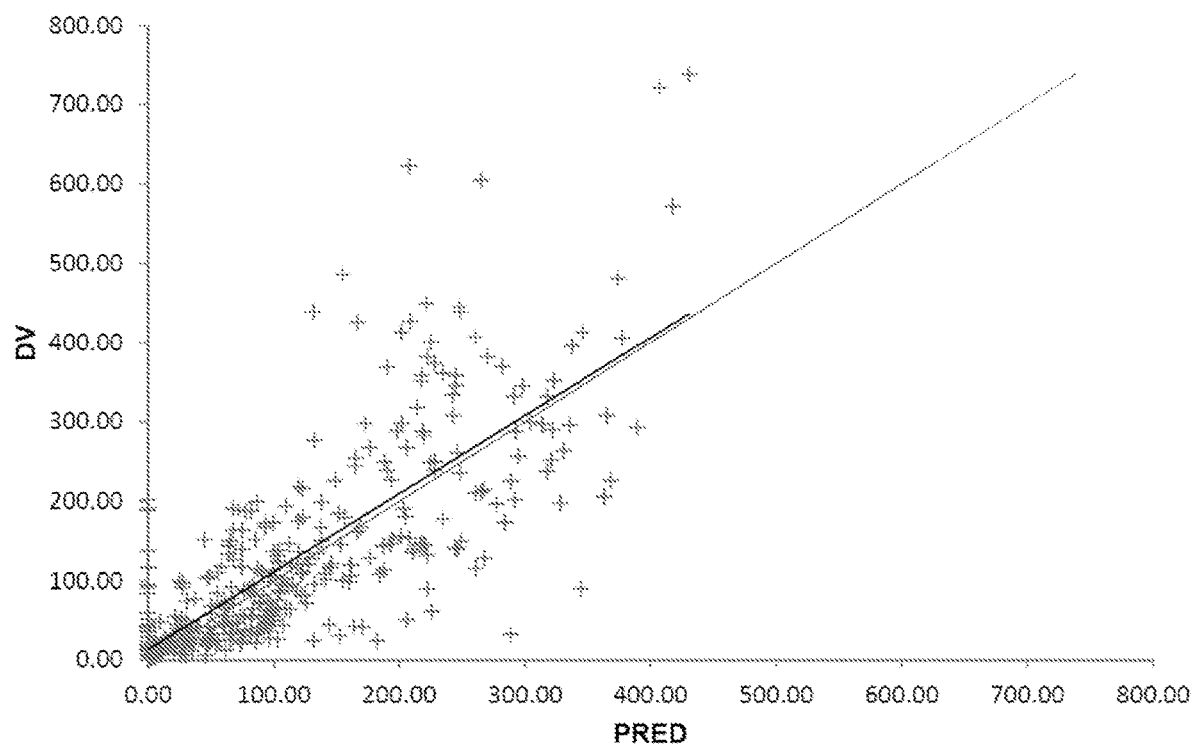
FIG. 32 shows a goodness of fit plot of observed data versus predicted data (DV vs. PRED) of the final model.
Figure 33:
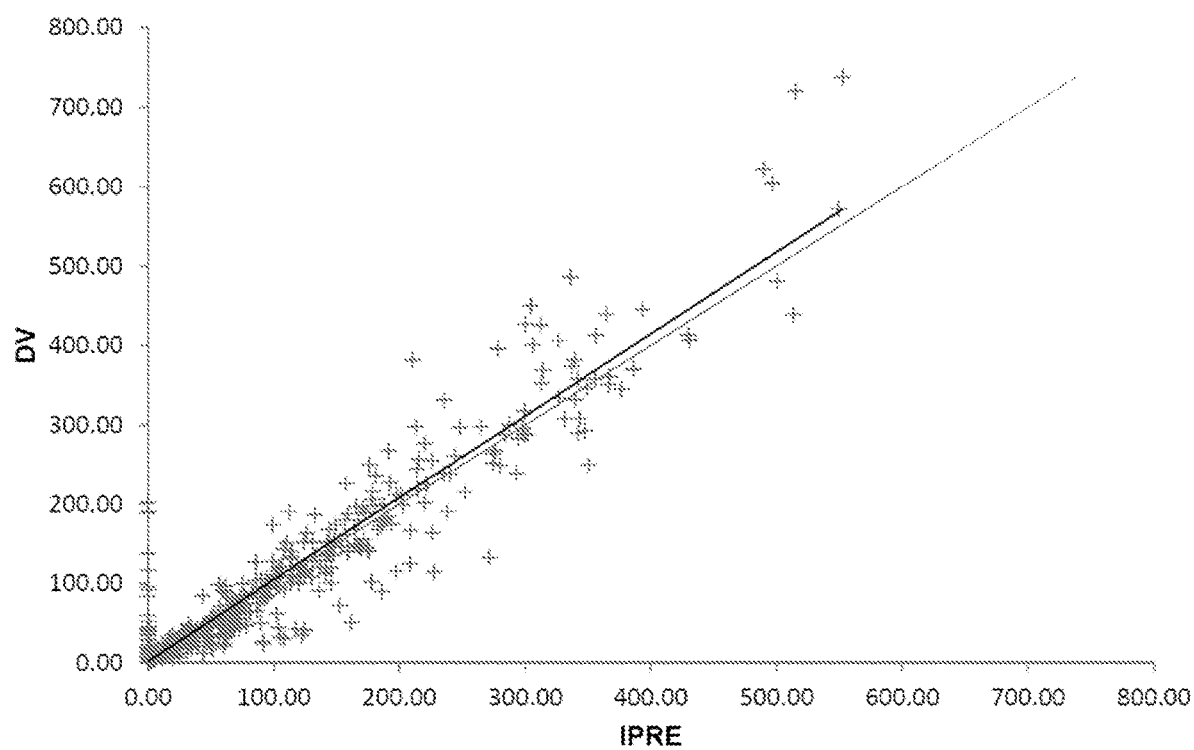
FIG. 33 shows a goodness of fit plot of observed data versus individual predicted data (DV vs. IPRED) of the final model.

After comparing observed data and predicted data, a final model was produced. GOF plots for the final model are found in FIGS. 32 and 33.

Bootstrap re-sampling was undertaken to compare the parameter estimates from the final model with those determined following 1000 bootstrap runs. In addition: visual predictive checks (plot comparing 95% prediction interval with observed data) and normalized prediction distribution errors (NPDE) techniques were applied for final model evaluation. Additionally a visual predictive check was performed.

Udenafil pharmacokinetics were well described by a two-compartment model with combined additive and proportional error. Apparent clearance (CL/F) were scaled using current body weight standardized to adult weight, 70 kg. Absorption rate constant was estimated as 0.28 h−1 (95% CI 0.16-0.39), apparent clearance (CL/F/70 kg) 36 L/h (95% CI 28.5-43.1), central volume of distribution (V2/F) 74 L (95% CI 36.2-112), inter-compartmental clearance (Q/F) 21.1 L (95% CI 10.4-31.8) and peripheral volume of distribution (V3/F) 181 L (95% CI 141-221). The final model was evaluated by bootstrap re-sampling, normalized prediction distribution errors, and visual predictive check techniques. These techniques demonstrated a good fit of the final covariate model to the data.

A two-compartment model with absorption rate constant successfully described the pharmacokinetics of udenafil in adolescents with single ventricle physiology after Fontan palliation. There was a statistically significantly influence on apparent clearance (CL/F) when subject body weight was standardized to adult weight, 70 kg included in the final model, CL/F L/hr/70 kg.

Example 7

Phase III Study of Udenafil in Fontan Patients

A Phase III study of udenafil in Fontan patients will determine the safety of udenafil (87.5 mg, twice daily) in an adolescent population with single ventrile congenital heart disease palliated with the Fontan procedure. The study will also evaluate the pharmacodynamics profile of udenafil over a period of time ranging from at least six months and up to one year. Pharmacodynamic outcomes will include exercise capacity, echocardiographic measures of ventricular function, endothelial function, and serum biomarkers, as well as measures of functional health status/quality of life. It is expected that udenafil (87.5 mg, twice daily) will be safe, and effective for improving exercise capacity and other endpoints of cardiovascular health, as well as improving quality of life.

Methodology—Randomized, double-blind, placebo-controlled clinical trial of a six month to one-year treatment with an 87.5 mg/twice a day dose in 300 subjects between 12 and 19 years of age who have had the Fontan surgery before 5 years of age.

Inclusion Criteria for the study include:
Males or females age 12-19.
Fontan surgery before 5 years of age.
Exclusion Criteria for the study include:
Height<132 cm.
Hospitalization for acute decompensated heart failure within the last 12 months.
Current intravenous inotropic drugs.
Undergoing evaluation for heart transplantation or listed for transplantation.
Diagnosis of protein losing enteropathy, plastic bronchitis, liver cirrhosis.
Known Fontan baffle obstruction, branch pulmonary artery stenosis, or pulmonary vein stenosis resulting in a mean gradient of >4 mm Hg between the regions proximal and distal to the obstruction as measured by either catheterization or echocardiography.
Single lung physiology.
Severe ventricular dysfunction assessed qualitatively by clinical echocardiography within 6 months prior to enrollment.
Severe valvar regurgitation, ventricular outflow obstruction, or aortic arch obstruction assessed by clinical echocardiography within 6 months prior to enrollment.
Significant renal, hepatic, gastrointestinal or biliary disorders that could impair absorption, metabolism or excretion of orally administered medications.
Inability to complete exercise testing at baseline screening.
History of PDE-5 inhibitor use within 3 months before study onset.
Use of any other drug to treat pulmonary hypertension within 3 months before study onset.
Known intolerance to oral udenafil.
Frequent use of medications or other substances that inhibit or induce CYP3A4.
Current use of alpha-blockers or nitrates.
Ongoing or planned participation in another research protocol that would either prevent successful completion of planned study testing or invalidate its results.
Noncardiac medical, psychiatric, and/or social disorder that would prevent successful completion of planned study testing or would invalidate its results.
Cardiac care, ongoing or planned, at a non-study center that would impede study completion.
For females: Pregnancy at the time of screening, pregnancy planned before study completion, or refusal to use an acceptable method of contraception for study duration.
Unable to abstain or limit intake of grapefruit juice during the duration of the trial.
Refusal to provide written informed consent/assent.
In the opinion of the primary care physician, the subject is likely to be non-compliant with the study protocol.

The study will include baseline measures of the proposed pharmacodynamics (PD) endpoints as well as quality of life surveys. For example, EndoPAT vascular assessment will be completed as the first PD test following consent. This must be performed in a fasting (from midnight until after the test), non-caffeinated state. After the vascular assessment, subjects will have a targeted echocardiogram to assess ventricular function. A short break will be given, either after the vascular assessment or after the echocardiogram, and a light snack will be provided. Safety labs will be performed following the vascular assessment, echocardiogram, and break. These will include collection of blood to evaluate serum creatinine and liver enzyme (aspartate transaminase and alanine transaminase) levels for all participants, and a urine pregnancy test for female participants. If the pregnancy test is positive all further testing will be stopped, the patient will not be enrolled into the trial and the result will be conveyed to the subject and/or guardians by the site-principal investigator in accordance with local IRB procedures. After the safety labs, an exercise test will be administered using a braked cycle ergometer following a ramp protocol previously published in the PHN Fontan Cross-Sectional Study. After exercise testing, subjects will have completed the baseline testing. Additionally, The Peds QL, cardiac specific Peds QL, and PCQLI will be administered during the baseline testing visit.

A study coordinator will call each subject weekly for four weeks and then monthly thereafter to collect adverse events and answer questions related to the study.

At the end of the study, subjects will arrive in a fasting, non-caffeinated state, and first undergo vascular function assessment including repeating the baseline tests as well as the quality of life surveys. Follow up with subjects may occur at 30 and 90 days following end-of-study testing to record any additional adverse events possibly or probably related to the study drug that may have occurred in the 90 days following completion of the study protocol.

It is expected that udenafil (87.5 mg bid) in adolescents with Fontan physiology over a 6-12 month period will be safe and well tolerated, with few, if any, serious adverse events related to udenafil. The severity of adverse events is determined according to the Common Terminology Criteria for Adverse Events (CTCAE) Version 4.0 MedDRA 12.1 (http://ctep.cancer.gov). Likewise, the effect of udenafil on pharmacodynamic outcomes including exercise capacity, echocardiographic measures of ventricular function, endothelial function, and biomarkers associated with heart failure is expected to improve over the course of treatment. The outcomes to be measured to determine the efficacy of udenafil in this patient population will include:
  Exercise: Change in maximal oxygen consumption from baseline to end-of-study testing measured using a standardized exercise test;
  Echo: Change in myocardial performance index as measured by pulse wave Doppler echocardiography from baseline to end-of-study testing;
  Endothelial Function: Change in log-transformed Reactive Hyperemia Index derived from the EndoPAT® device; and
  Biomarkers: Change in serum BNP level from baseline to end-of-study.
As well as:
  Exercise: Submaximal measures of exercise capacity will be collected and evaluated.
  Echo: Measure of systolic and diastolic function will be collected from a targeted echocardiogram.

The study may also look at outcomes related to ventricular cavity size, eccentricity, and mass; systolic function as estimated using mean dP/dt during isovolumetric contraction (dP/dtic) and peak systolic annular velocity (S') on tissue Doppler; tissue Doppler based estimates of diastolic function and MPI; and qualitative and quantitative estimate of AV valve insufficiency.

It is also expected that functional health status will improve following administration of udenafil. The change in functional health status from baseline to the end of the study may be measured by the full scale Peds QL, Peds QL physical functioning score, Peds QL psychosocial functioning score, Peds QL cardiac-specific module quality of life score, and/or the pediatric cardiac quality of life inventory (PCQLI) score.

Furthermore, genetic material may be collected during the study to identify genetic determinants of response to udenafil after the Fontan procedure in persons with single-ventricle lesions. This will provide an indication of whether specific sub-populations of patients will have a more positive response to udenafil than others. For instance, the response to udenafil may be influenced by variants related to the vascular response to udenafil. Variants in the endothelial nitric oxide synthase gene have been reported to influence the response to sildenafil in patients with erectile dysfunction, although this has not been studied for udenafil. Variation in genes that regulate the vascular, inotropic and chronotropic response to exercise may influence the exercise capacity of patients after the Fontan procedure as well as the response to udenafil. DNA will be stored to perform future genotyping studies to analyze the genetic contribution to the response to udenafil.

Additional covariate measures will include, but may not be limited to, age, gender, race/ethnicity, height/weight, ventricular morphology, resting oxygen saturation, baseline pharmacodynamics test results, and current medication use. Observance of these variables will allow for the identification of associations between a variety of clinical factors and both safety and PD outcomes.

Data collection will include recording demographic information including age, gender, race, ethnicity, cardiac anatomy, date of Fontan procedure, presence of a fenestration, degree of atrioventricular valve regurgitation, grade of ventricular function, concomitant medications, and significant co-morbidities. Safety data will reviewed with each subject at each study visit and during telephone encounters. These events will be recorded and graded by severity and relationship to the study drug based upon established criteria. Two additional telephone encounters will take place 30 days and 90 days following end-of-study testing to assess for any adverse events possibly or probably related to the study drug in the period following the completion of study procedures.

Other data collection will include:
  Exercise stress test—Data from the braked cycle ergometry exercise stress tests will be collected according to protocol established in the PHN Fontan Cross-Sectional Study3.
  Assessment of ventricular performance—Each study echocardiogram will be stored in a de-identified manner and sent to a core laboratory, which will perform the data analysis and submit the measurements to the PHN Data Coordinating Center (DCC).
  Vascular function testing—De-identified data from Endo-PAT® testing will be collected according to a standardized protocol. These data will be sent to a vascular core lab, which will perform the analysis and submit the measurements to the PHN DCC.
  Biomarkers—Serum for measurement of BNP level will be sent to a core clinical lab. Results will be sent directly to the PHN DCC.
  Quality of life survey—Results of the Quality of life surveys will be submitted to the PHN DCC.
  Samples for the biorepository—Samples collected for the biorepository will be shipped directly to the biorepository for future analysis.

Subjects will be treated with other medications at the discretion of their physicians. At the study visits, current medications will be recorded on the study forms. If a subject begins open-label use of any other PDE-5 inhibitor at any time during the study, withdrawal from the study drug is required.

When an individual subject completes the study, the subject's primary cardiologist will be notified, and the study drug will be stopped; there is no need to wean subjects off of the study drugs. The decision of whether to continue the use of an off label PDE-5 inhibitor for individual subjects will be decided by the subjects and their primary cardiologist.

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of treating a patient born with functional single ventricle congenital heart disease who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:
  orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity,
  wherein the patient is a human,
  wherein the patient has undergone Fontan surgery,
  wherein the human patient is between about 12 years old and about 18 years old,
  wherein the effective dose of udenafil, or a pharmaceutically acceptable salt thereof, is about 87.5 mg, and
  wherein the treatment regimen comprises orally administering the oral dosage form to the human adolescent twice daily.

2. The method of claim 1, wherein the oral dosage form is a tablet.

3. The method of claim 1, wherein the oral dosage form is a solid or semi-solid oral dosage form selected from a group of solid or semi-solid oral dosage forms consisting of a tablet, a capsule, a gel, a liquid dispersion, a pill, a powder and a suspension.

4. A method of treating a patient born with functional single ventricle congenital heart disease who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:
  orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity,
  wherein the patient is a human,
  wherein the patient has undergone Fontan surgery,
  wherein the human patient is between about 12 years old and about 18 years old, and
  wherein the total daily dose of udenafil, or a pharmaceutically acceptable salt thereof, is from about 125 mg to about 175 mg.

5. The method of claim 4, wherein the oral dosage form is a tablet.

6. The method of claim 4, wherein the oral dosage form is a solid or semi-solid oral dosage form selected from a group of solid or semi-solid oral dosage forms consisting of a tablet, a capsule, a gel, a liquid dispersion, a pill, a powder and a suspension.

7. A method of treating a patient born with a congenital heart defect who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:
  orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity,
  wherein the patient is a human,
  wherein the patient has undergone Fontan surgery,
  wherein the human patient is between about 12 years old and about 18 years old,
  wherein the effective dose of udenafil, or a pharmaceutically acceptable salt thereof, is about 87.5 mg, and
  wherein the treatment regimen comprises orally administering the oral dosage form to the human adolescent twice daily.

8. The method of claim 7, wherein the oral dosage form is a tablet.

9. The method of claim 7, wherein the oral dosage form is a solid or semi-solid oral dosage form selected from a group of solid or semi-solid oral dosage forms consisting of a tablet, a capsule, a gel, a liquid dispersion, a pill, a powder and a suspension.

10. A method of treating a patient born with a congenital heart defect who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:
  orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity,
  wherein the patient is a human,
  wherein the patient has undergone Fontan surgery,
  wherein the human patient is between about 12 years old and about 18 years old, and wherein the total daily dose of udenafil, or a pharmaceutically acceptable salt thereof, is from about 125 mg to about 175 mg.

11. The method of claim 10, wherein the oral dosage form is a tablet.

12. The method of claim 10, wherein the oral dosage form is a solid or semi-solid oral dosage form selected from a group of solid or semi-solid oral dosage forms consisting of a tablet, a capsule, a gel, a liquid dispersion, a pill, a powder and a suspension.

13. A method of treating a patient who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:

orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity, wherein the patient is a human, wherein the patient has undergone Fontan surgery, wherein the human patient is between about 12 years old and about 18 years old, wherein the effective dose of udenafil, or a pharmaceutically acceptable salt thereof, is about 87.5 mg, and wherein the treatment regimen comprises orally administering the oral dosage form to the human adolescent twice daily.

14. The method of claim 13, wherein the oral dosage form is a tablet.

15. The method of claim 13, wherein the oral dosage form is a solid or semi-solid oral dosage form selected from a group of solid or semi-solid oral dosage forms consisting of a tablet, a capsule, a gel, a liquid dispersion, a pill, a powder and a suspension.

16. The method of claim 13, wherein the patient is born with a single functional ventricle.

17. The method of claim 13, wherein the patient is born with a congenital heart defect.

18. A method of treating a patient who has undergone Fontan palliation for improving the patient's exercise capacity or for increasing the likelihood of improving the patient's exercise capacity, whose exercise capacity is adversely affected due to a decline in the patient's heart function after Fontan palliation, wherein the patient is in need of treatment to improve the patient's exercise capacity or to increase the likelihood of improving the patient's exercise capacity, wherein exercise capacity is determined by maximum oxygen uptake at maximum exercise output ($VO_2$ measurement), said method comprising:

orally administering to the patient in accordance with a treatment regimen an oral dosage form comprising an effective dose of udenafil, or a pharmaceutically acceptable salt thereof, to improve the patient's $VO_2$ measurement or to increase the likelihood of improving the patient's $VO_2$ measurement for improving the patient's exercise capacity or for increasing the likelihood of improving the patient's exercise capacity, wherein the patient is a human, wherein the patient has undergone Fontan surgery, wherein the human patient is between about 12 years old and about 18 years old, and wherein the total daily dose of udenafil, or a pharmaceutically acceptable salt thereof, is from about 125 mg to about 175 mg.

19. The method of claim 18, wherein the oral dosage form is a tablet.

20. The method of claim 18, wherein the oral dosage form is a solid or semi-solid oral dosage form selected from a group of solid or semi-solid oral dosage forms consisting of a tablet, a capsule, a gel, a liquid dispersion, a pill, a powder and a suspension.

21. The method of claim 18, wherein the patient is born with a single functional ventricle.

22. The method of claim 18, wherein the patient is born with a congenital heart defect.

* * * * *